US007608699B2

(12) United States Patent
Muesing et al.

(10) Patent No.: US 7,608,699 B2
(45) Date of Patent: Oct. 27, 2009

(54) SYNTHETIC NUCLEAR LOCALIZATION SIGNAL DERIVED FROM LENTIVIRAL INTEGRASE AND METHODS OF USE THEREOF

(75) Inventors: Mark A. Muesing, New York, NY (US); Tshaka J. Cunningham, New York, NY (US)

(73) Assignee: Rockefeller University, New York, NY (US)

( * ) Notice: Subject to any disclaimer, the term of this patent is extended or adjusted under 35 U.S.C. 154(b) by 0 days.

(21) Appl. No.: 11/023,996

(22) Filed: Dec. 29, 2004

(65) Prior Publication Data

US 2006/0134651 A1 Jun. 22, 2006

Related U.S. Application Data

(60) Provisional application No. 60/532,563, filed on Dec. 29, 2003.

(51) Int. Cl.
*C07H 21/02* (2006.01)
*C07H 21/04* (2006.01)

(52) U.S. Cl. .................... 536/23.1; 536/23.7; 536/23.72

(58) Field of Classification Search ................. 536/23.1
See application file for complete search history.

(56) References Cited

U.S. PATENT DOCUMENTS

| | | | | |
|---|---|---|---|---|
| 5,013,830 | A | 5/1991 | Ohtsuka et al. | |
| 5,149,797 | A | 9/1992 | Pederson et al. | |
| 5,220,007 | A | 6/1993 | Pederson et al. | |
| 5,256,775 | A | 10/1993 | Froehler | |
| 5,279,833 | A | 1/1994 | Rose | |
| 5,366,878 | A | 11/1994 | Pederson et al. | |
| 5,403,711 | A | 4/1995 | Walder et al. | |
| 5,491,133 | A | 2/1996 | Walder et al. | |
| 5,565,350 | A | 10/1996 | Kmiec | |
| 5,623,065 | A | 4/1997 | Cook et al. | |
| 5,652,355 | A | 7/1997 | Metelev et al. | |
| 5,652,356 | A | 7/1997 | Agrawal | |
| 5,700,922 | A | 12/1997 | Cook | |
| 2003/0158131 | A1 * | 8/2003 | Aldovini | 514/44 |
| 2007/0203325 | A1 | 8/2007 | Yao et al. | 530/300 |

FOREIGN PATENT DOCUMENTS

| | | |
|---|---|---|
| WO | WO 91/06309 | 5/1991 |
| WO | WO 93/24640 | 12/1993 |
| WO | WO 96/18372 | 6/1996 |
| WO | WO 0068436 A1 * | 11/2000 |

OTHER PUBLICATIONS

Totsugawa et al. Lentiviral transfer of the LacZ gene into human endothelial cells and human bone marrow mesenchymal stem cells. Cell Transplantation 2002, vol. 11, No. 5, p. 481-488.*

Score result: sequence alignment page between SEQ ID No. 138 and SEQ ID No. 1 of WO 200068436A1.*

Puras Lutzke et al. Characterization of the minimal DNA-binding domain of the HIV integrase protein. Nucleic Acids Research 1994, vol. 22, No. 20, pp. 4125-4131.*

Bukrinsky, M. I., et al 1993. "A nuclear localization signal within HIV-1 matrix protein that governs infection of non-dividing cells." Nature 365:666-669.

Bukrinsky, M. I., et al 1993. "Association of integrase, matrix, and reverse transcriptase antigens of human immunodeficiency virus type 1 with viral nucleic acids following acute infection." Proc Natl Acad Sci U S A 90:6125-9.

Butler, S. L., et al 2001. "A quantitative assay for HIV DNA integration in vivo." Nat Med 7:631-4.

Cannon, P. M., et al 1996. "Conserved sequences in the carboxyl terminus of integrase that are essential for human immunodeficiency virus type 1 replication." J Virol 70:651-7.

Charneau, P., et al 1994. "HIV-1 reverse transcription. A termination step at the center of the genome." J Mol Biol 241:651-62.

Cherepanov, P., et al 2003. "HIV-1 integrase forms stable tetramers and associates with LEDGF/p75 protein in human cells." J Biol Chem 278:372-81.

Depienne, C., et al 2001. "Characterization of the nuclear import pathway for HIV-1 integrase." J Biol Chem 276:18102-7.

Depienne, C., et al 2000. "Cellular distribution and karyophilic properties of matrix, integrase, and Vpr proteins from the human and simian immunodeficiency viruses." Exp Cell Res 260:387-95.

Dvorin, J. D., et al 2002. "Reassessment of the Roles of Integrase and the Central DNA Flap in Human Immunodeficiency Virus Type 1 Nuclear Import." J Virol 76:12087-12096.

Eijkelenboom, A. P., et al 1995. "The DNA-binding domain of HIV-1 integrase has an SH3-like fold." Nat Struct Biol 2:807-10.

Eijkelenboom, A. P., et al 1999. "Refined solution structure of the C-terminal DNA-binding domain of human immunovirus-1 integrase. Proteins." 36:556-64.

Engelman, A., et al 1993. "Identification of discrete functional domains of HIV-1 integrase and their organization within an active multimeric complex." EMBO J 12:3269-75.

Farnet, C. M., et al 1991. "Determination of viral proteins present in the human immunodeficiency virus type 1 preintegration complex." J Virol 65:1910-5.

Fouchier, R. A., et al 1998. "Interaction of the human immunodeficiency virus type 1 Vpr protein with the nuclear pore complex." J. Virol. 72:6004-6013.

Limon, A., et al 2002. "Nuclear Localization of Human Immunodeficiency Virus Type 1 Preintegration Complexes (PICs): V165A and R166A Are Pleiotropic Integrase Mutants Primarily Defective for Integration, Not PIC Nuclear Import." J Virol 76:10598-607.

(Continued)

*Primary Examiner*—Larry R Helms
*Assistant Examiner*—Louise Humphrey
(74) *Attorney, Agent, or Firm*—Medlen & Carroll, LLP

(57) ABSTRACT

The present invention provides novel peptides, nucleic acids, vectors, compounds, compositions and methods for regulating nuclear import. The present invention also relates to a lentiviral NLS, and methods of use thereof for inhibiting HIV pathogenesis and disease progression, and for gene delivery methods.

1 Claim, 31 Drawing Sheets

OTHER PUBLICATIONS

Limon, A., et al 2002. "Wild-type levels of nuclear localization and human immunodeficiency virus type 1 replication in the absence of the central DNA flap." J Virol 76:12078-86.

Maertens, G., et al 2003. "LEDGF/p75 is essential for nuclear and chromosomal targeting of HIV-1 integrase in human cells." J Biol Chem 278:33528-39.

Miller, M. D., et al1994. "The human immunodeficiency virus-1 nef gene product: a positive factor for viral infection and replication in primary lymphocytes and macrophages." J Exp Med 179:101-13.

Mulder, L. C., et al 2002. "Interaction of HIV-1 integrase with DNA repair protein hRad18." J Biol Chem 277:27489-93.

Mulder, L. C., et al 2000. "Degradation of HIV-1 integrase by the N-end rule pathway." J Biol Chem 275:29749-53.

Nilsen, B. M., et al 1996. "Monoclonal antibodies against human immunodeficiency virus type 1 integrase: epitope mapping and differential effects on integrase activities in vitro." J Virol 70:1580-7.

Wiskerchen, M., et al 1995. "Human immunodeficiency virus type 1 integrase: effects of mutations on viral ability to integrate, direct viral gene expression from unintegrated viral DNA templates, and sustain viral propagation in primary cells." J. Virol. 69:376-386.

Wiskerchen, M., et al 1995. "Identification and characterization of a temperature-sensitive mutant of human immunodeficiency virus type 1 by alanine scanning mutagenesis of the integrase gene." J Virol 69:597-601.

Wu, X., et al 1999. "Human immunodeficiency virus type 1 integrase protein promotes reverse transcription through specific interactions with the nucleoprotein reverse transcription complex." J Virol 73:2126-35.

Wu, X., etla 1997. "Functional RT and IN incorporated into HIV-1 particles independently of the Gag/Pol precursor protein." EMBO J 16:5113-22.

Zennou, V., et al 2000. "HIV-1 genome nuclear import is mediated by a central DNA flap." Cell 101:173-85.

* cited by examiner

Native Nucleotide Sequence: Integrase Coding Region tttttagatggaatagataaggcccaagatgaacatgagaaatatcacagtaattggagagcaatggctagtgattttaacctgccacctgtagtagcaaaagaaatagtagccagctgtgataaatgtcagctaaaag
gagaagccatgcatggacaagtagactgtagtccaggaatatggcaactagattgtacacatttagaaggaaaaaagttatcctggtagcagttcatgtagccagtggatatatagaagcagaagttattccagcagaaa
cagggcaggaaacagcatattttcttttaaaattagcaggaagatggccagtaaaaacaatacatacagacaatggcagcaatttcaccagtgctacggttaaggccgcctgttggtgggcgggaatcaagcagga
atttggaattccctacaatccccaaagtcaaggagtagtagaatctatgaataaagaattaaagaaaattataggacaggacaggtaagagatcaggctgaacatcttaagacagcagtacaaatggcagtattcatccacaatt
ttaaaagaaaaggggggattggggggtacagtgcaggggaaagaatagtagacataatagcaacagacatacaaactaaagaattacaaaaacaaattacaaaaattcaaaattttcgggtttattacagggacagc
agaaatccactttggaaaggaccagcaaagctcctctggaaaggtgaaggggcagtagtaatacaagataatagtgacataaaagtagtgccaagaagaaaagcaaagatcattagggattatggaaaacagatg
gcaggtgatgattgtgtggcaagtagacaggatgaggattag (SEQ ID NO: 2)

Amino Acid sequence of the Native Integrase Protein:

FLDGIDKAQDEHEKYHSNWRAMASDFNLPPVVAKEIVASCDKCQLKGEAMHGQVDCSPGIWQLDCTHLEGKVILVAVHVASG
YIEAEVIPAETGQETAYFLLKLAGRWPVKTIHTDNGSNFTSATVKAACWWAGIKQEFGIPYNPQSQGVVESMNKELKKIIGQVRD
QAEHLKTAVQMAVFIHNFKRKGGIGGYSAGERIVDIIATDIQTKELQKQITKIQNFRVYYRDSRNPLWKGPAKLLWKGEGAVVIQ
DNSDIKVVPRRKAKIIRDYGKQMAGDDCVASRQDED (SEQ ID NO: 3).

*FIG. 1F/1*

Table 1: Mutations in Integrase coding region, and their corresponding amino acid substitutions:

| Nucleotide sequence | Resulting IN Mutation | SEQ ID NO: |
|---|---|---|
| gcaatggctagtgCttttaacctgccacct | D25A | 4 |
| atatggcaactagCttgtacacatttagaa | D64A | 5 |
| catggacaagtagCctgtagtccaggaat | D55A | 6 |
| ctggtagcagttGCtgtagccagtggatat | H78A | 7 |
| acaatacatacagCcaatggcagcaatttc | D116A | 8 |
| agtgctacggttGCggccgcctgttggtgg | K127A | 9 |
| tgggcgggaatcGCgcaggaatttggaatt | K136A | 10 |
| caaggagtagtagCatctatgaataaagaa | E152A | 11 |
| gaatctatgaatGCagaattaaagaaaatt | K156A | 12 |
| aataaagaattaGCgaaaattataggacag | K159A | 13 |
| aaagaattaaagGCaattataggacaggta | K160A | 14 |
| attataggacaggCaagagatcaggctgaa | *V165A | 15 |
| ataggacaggtaGCagatcaggctgaacat | *R166A | 16 |
| gcagtattcatcGCcaattttaaaagaaa a | H183A | 17 |
| atccacaattttGCaagaaaagggggatt | K186A | 18 |
| atccacaattttCaaagaaaagggggatt | *K186Q | 19 |
| cacaattttaaaGCaaaagggggattggg | R187A | 20 |
| gacatacaaactGCagaattacaaaaacaa | K211A | 21 |
| atacaaactaaagCattacaaaaacaaatt | E212A | 22 |
| aaagaattacaaGCacaaattacaaaaatt | K215A | 23 |
| aaacaaattacaGCaattcaaaattttcgg | K219A | 24 |
| attcaaaattttGCggtttattacagggac | R224A | 25 |
| cgggtttattacGCggacagcagaaatcca | R228A | 26 |
| aagctcctctggGCaggtgaagggggcagta | K244A | 27 |
| aatccactttggGCaggaccagcaaagctc | K236A | 28 |
| aaaggaccagcaGCgctcctctggaaaggt | K240A | 29 |
| aaagtagtgccaGCaagaaaagcaaagatc | R262A | 30 |
| gtagtgccaagaGCaaaagcaaagatcatt | R263A | 31 |
| gtgccaagaagaGCagcaaagatcattagg | K264A | 32 |
| agaagaaaagcaGCgatcattagggattat | K266A | 33 |
| gcaaagatcattGCggattatggaaaacag | R269A | 34 |
| cctgtagtagcaGCagCaatagtagccagc | K34A /E35A | 35 |

FIG. 1F/1.1

| Nucleotide sequence | Resulting IN Mutation | SEQ ID NO: |
|---|---|---|
| gtagccagctgtgCtGCatgtcagctaaaa | D41A/K42A | 36 |
| aaatgtcagctaGCaggagCagccatgcat | K46A/E48A | 37 |
| ctagattgtacaGCtttagCaggaaaagtt | H67A/E69A | 38 |
| tgtacacatttagCaggaGCagttatcctg | E69A/K71A | 39 |
| agtggatatatagCagcagCagttattcca | E85A/E87A | 40 |
| tattttcttttaGCatta gcaggaGCatgg | K103A/R107A | 41 |
| agatggccagtaGCaacaataGCtacagac | R107A/K111A | 42 |
| agatggccagtaGCaacaataGCtacagac | K111A/H114A | 43 |
| gaatctatgaatGCagaattaGCgaaaatt | K156A/K159A | 44 |
| gaatctatgaatGCagaattaGCgGCaatt | K156A/K159A/K16A | 45 |
| gaatctatgaatGCagaattaaagGCaatt | K1 56A/K160A | 46 |
| aataaagaattaGCgGCaattataggacag | K159A/K160A | 47 |
| attataggacaggCaGCagatcaggctgaa | *V165A/R166A | 48 |
| ataggacaggtaGCagCtcaggctgaacat | R166A/D167A | 49 |
| agagatcaggctgCaGCtcttaagacagca | E170A/H171A | 50 |
| gatcaggctgaaGCtcttGCgacagcagta | H171A/K173A | 51 |
| atccacaattttGCaGCaaaagggggggatt | K186A/R187A | 52 |
| atccacaattttGCaagaGCaggggggatt | K186A/K188A | 53 |
| atccacaattttGCaGCaGCaggggggatt | K186A/R187A/K188A | 54 |
| atccacaattttaaaGCaGCaggggggatt | R187A/K188A | 55 |
| tacagtgcaggggCaGCaatagtagacata | E198A/R199A | 56 |
| agtgcaggggaaGCaatagtagCcataata | R199A/D202A | 57 |
| actaaagaattacTaaaacTaattacaaaa | *Q214L/Q216L | 58 |
| attcaaaattttGCggtttattacGCggac | R224A/R228A | 59 |
| gtttattacagggCcagcGCaaatccactt | D229A/R231A | 60 |
| aatccactttggGCaggaccagcaGCgctc | K236A/K240A | 61 |
| gtagtaatacaagCtaatag tgCcataaaa | D253A/D256A | 62 |
| caagataatagtgCcataGCagtagtgcca | D256A/K258A | 63 |
| aaagtagtgccaGCaGCaaaagcaGCgatc | R262A/R263A/K266A | 64 |
| gtagtgccaagaGCaGCagcaaagatcatt | R263A/K264A | 65 |
| gcaaagatcattGCggCttatggaaaaca | R269A/D270A | 66 |

FIG. 1F/1.2

TABLE 2. Subcellular Localization of IN Mutants in the Context of Fusion to EGFP.

| IN Mutated Protein: | Nuclear Localization | Partial Change in Position | Nuclear Exclusion | SEQ ID NO: |
|---|---|---|---|---|
| D25A | + | | | 67 |
| D64A | + | | | 68 |
| D55A | + | | | 69 |
| H78A | + | | | 70 |
| D116A | + | | | 71 |
| K127A | + | | | 72 |
| K136A | + | | | 73 |
| E152A | + | | | 74 |
| K156A | + | | | 75 |
| K159A | + | | | 76 |
| K160A | + | | | 77 |
| *V165A | + | | | 78 |
| *R166A | + | | | 79 |
| H183A | + | | | 80 |
| K186A | + | | | 81 |
| *K186Q | + | | | 82 |
| R187A | + | | | 83 |
| K211A | + | | | 84 |
| E212A | + | | | 85 |
| K215A | + | | | 86 |
| K219A | + | | | 87 |
| R224A | + | | | 88 |
| R228A | + | | | 89 |
| K244A | + | | | 90 |
| K236A | | + | | 91 |
| K240A | | + | | 92 |
| R262A | | + | | 93 |
| R263A | + | | | 94 |
| K264A | + | | | 95 |
| K266A | | + | | 96 |
| R269A | + | | | 97 |
| K34A/E35A | + | | | 98 |
| D41A/K42A | + | | | 99 |

*FIG. 1F/2.1*

| IN Mutated Protein: | Nuclear Localization | Partial Change in Position | Nuclear Exclusion | SEQ ID NO: |
|---|---|---|---|---|
| K46A/E48A | + | | | 100 |
| H67A/E69A | + | | | 101 |
| E69A/K71A | + | | | 102 |
| E85A/E87A | + | | | 103 |
| K103A/R107A | + | | | 104 |
| R107A/K111A | + | | | 105 |
| K111A/H114A | + | | | 106 |
| K156A/K159A | + | | | 107 |
| K156A/K159A/R166A | + | | | 108 |
| K156A/K160A | + | | | 109 |
| K159A/K160A | + | | | 110 |
| *V165A/R166A | + | | | 111 |
| R166A/D167A | + | | | 112 |
| E170A/H171A | + | | | 113 |
| H171A/K173A | + | | | 114 |
| K186A/R187A | + | | | 115 |
| K186A/K188A | + | | | 116 |
| K186A/R187A/K188A | | + | | 117 |
| R187A/K188A | + | | | 118 |
| E198A/R199A | + | | | 119 |
| R199A/D202A | + | | | 120 |
| *Q214L/Q216L | + | | | 121 |
| R224A/R228A | + | | | 122 |
| D229A/R231A | + | | | 123 |
| K236A/K240A | | | + | 124 |
| D253A/D256A | + | | | 125 |
| D256A/K258A | + | | | 126 |
| R262A/R263A/K266A | | | + | 127 |
| R263A/K264A | + | | | 128 |
| R269A/D270A | + | | | 129 |

The EGFP-IN fusion construct containing the indicated charged-cluster-to alanine mutation(s) was transfected into 293 and 293T cells and its subcellular localization determined by DAPI counter-staining and deconvolution microscopy. Amino acid residues that are preceded with an asterisk denote those mutations that have been reported to cause nuclear exclusion in other ex-perimental systems.

*FIG.1F*/2.2

*Conservation of the SH3/NLS in Primate Lentiviruses (HIV-1, HIV-2, SIV) - A Survey of 540 Sequences*

```
        1**1**1**1**1**1**1**1        2**2**2**2**2**2**22**2**2**2**2**2**2
I  Q  N  F  R  V  Y  Y  R  D  S  R  N  P  L  W  K  G  P A  K  L  L  W  K  G
h  o  o  @  ^  @  @  a  b  ac s  b  ^  ^  ^  @  b  @  @ s  ^  br h  @  b  @

        3**3**3**3**3**3        4**4 4**4**4      X**X**X      5**5**5**5**5
E  G  A  V  V  I  Q  D  N  S  D  I K  V  V  P  R  R  K  A  K  I  I  R  D
@  @  @  br br br o  ^  o  ^  o  br^  ^  br @  @  b  b  s  @  @  br b  ^
```

1*-5* beta pleated sheet stabilized by hydrophobic interactions:
X* the only alpha helix in SH3 region
a = aromatic (tyr, phe or trp)
ac = acidic (asp or glu)
b = basic (lys, arg or his)
br = branched chain (leu, val or ile)
h = hydrophobic (tyr, phe, trp, ile, leu, met, val or pro)
o = polar (all except tyr, phe, trp, ile, leu, val, met, gly or ala)
p = pro or ser
s = small (gly, ala, cys or asn)
^ = conserved but replacements observed in more than one amino acid grouping
@ = absolutely conserved (0 or 1 occurrence in 550 sequences)

FIG. 2

*Frequency of Substitution (IN 220-270)*

| 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|
| I | Q | N | F | R | V | Y | Y | R | D | S | R | N | P | L | W | K | G | P |
| 18 | 8 | 35 | 1 | 11 | 1 | 2 | 20 | 3 | 1 | 48 | 4 | 35 | 3 | * | 1 | 3 | 1 | 1 |

| 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|
| A | K | L | L | W | K | G | E | G | A | V | V | I | Q | D | N | S | D | I |
| 0 | 11 | 2 | 3 | 0 | 1 | 0 | 1 | 1 | 0 | 2 | 2 | 8 | 1 | 4 | 17 | 40 | * | 3 |

| 39 | 40 | 41 | 42 | 43 | 44 | 45 | 46 | 47 | 48 | 49 | 50 | 51 |
|---|---|---|---|---|---|---|---|---|---|---|---|---|
| K | V | V | P | R | R | K | A | K | I | I | R | D |
| 2 | 6 | 9 | 0 | 1 | 2 | 4 | * | 1 | 1 | 8 | 85 | 10 |

- >100 substitutions

*FIG. 3*

Compilation of IN NLS (520 sequences from all clades of HIV)
Conservation of Amino Acid Sequence Reference Sequence and Substitutions (residues critical to NLS activity in bold)

Amino Acid: IQNFRVYYRDSRNPLWKGPAKLLWKGEGAVVIQDNSDIKVVPRRKAKIIRD

```
Amino Acid: IQNFRVYYRDSRNPLWKGPAKLLWKGEGAVVIQDNSDIKVVPRRKAKIIRD
Position:   1   5    10   15   20   25   30   35   40   45   50

            LRKSQAHFKGNKDSPRRR  QPF R DR LLLRHKNEVRII SKRVQVLKH
             HH W CHG GGE I     EVI      IAV EDGGMEA    E   VGN
             NT         G S       P           SK             G
              I           V                                  E
                          M
                          F
```

FIG. 5

NLS ACTIVITY

| | |
|---|---|
| 212-288 | + |
| 220-288 | + |
| 230-288 | − |
| 240-288 | − |
| 250-288 | − |
| 260-288 | − |
| 270-288 | − |

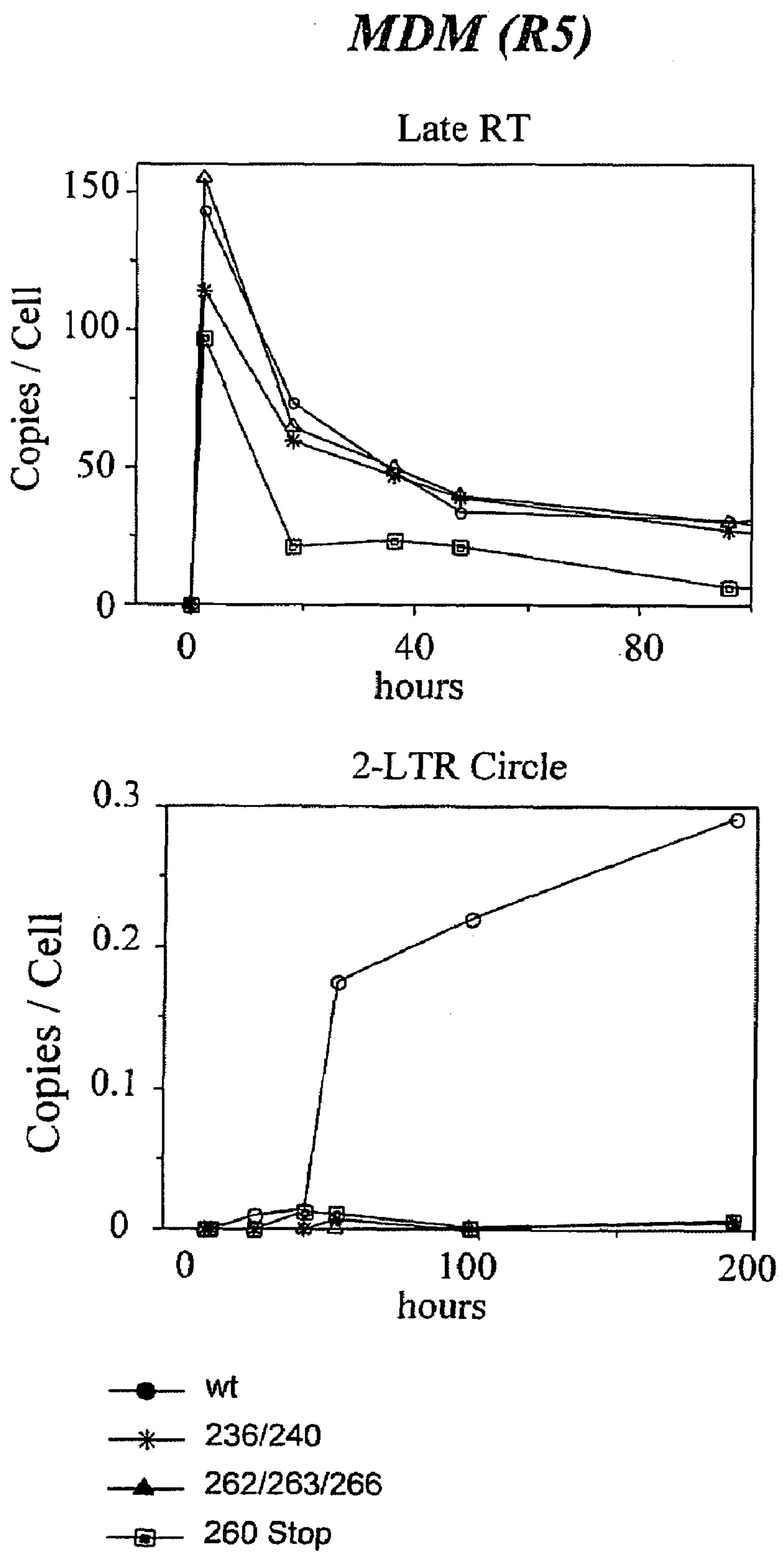
FIG. 10A/1

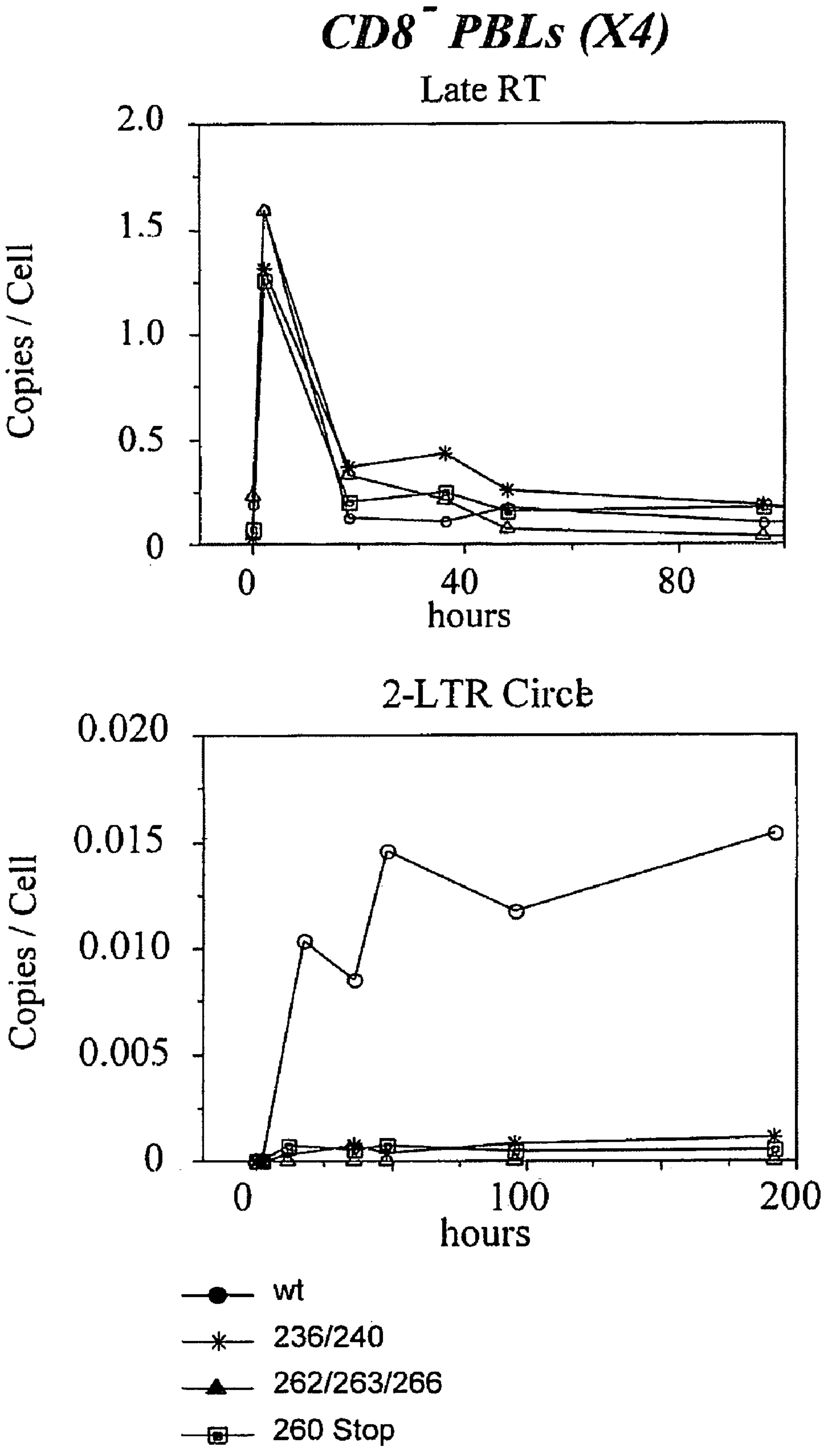
FIG.10A/2

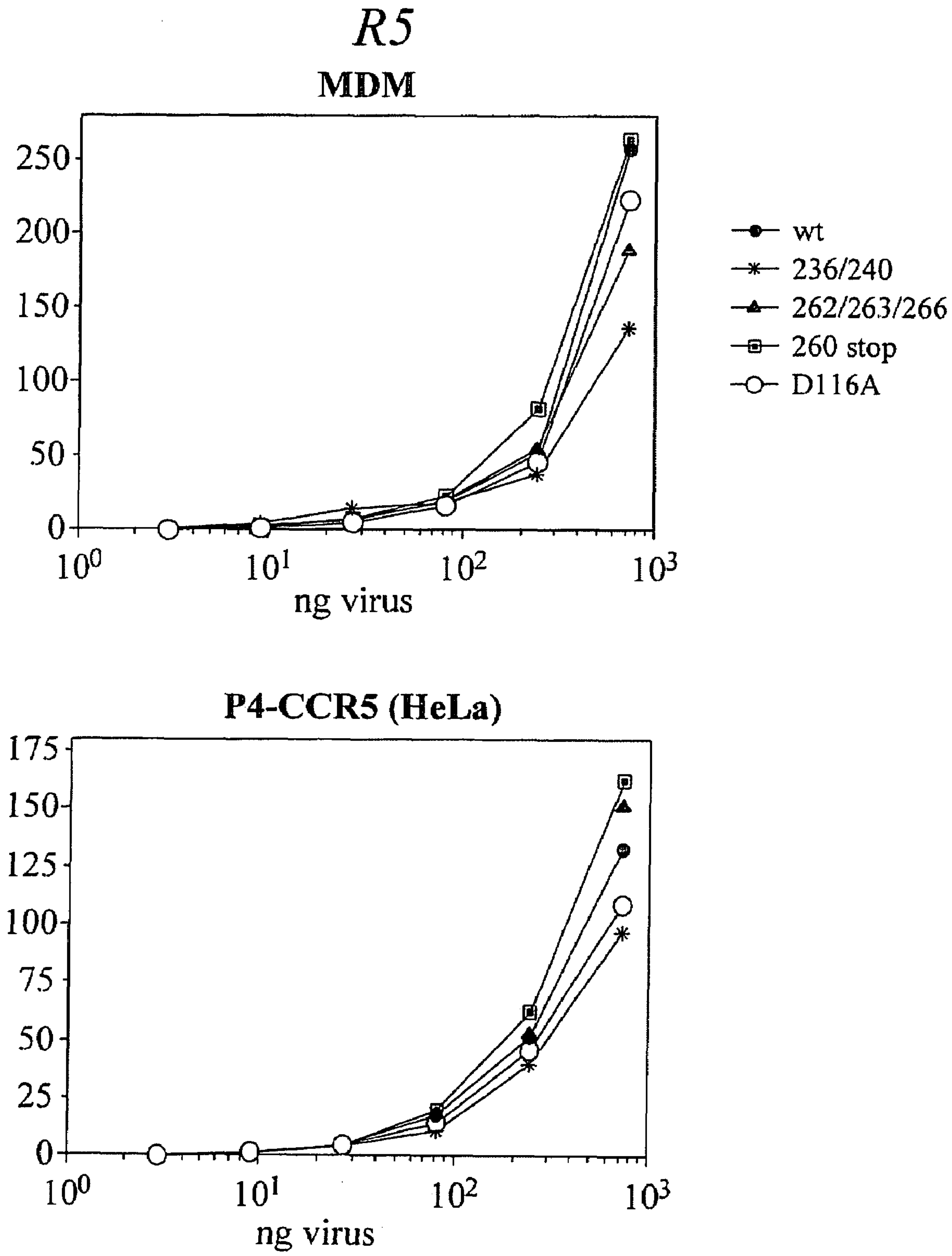
*FIG.10C/1*

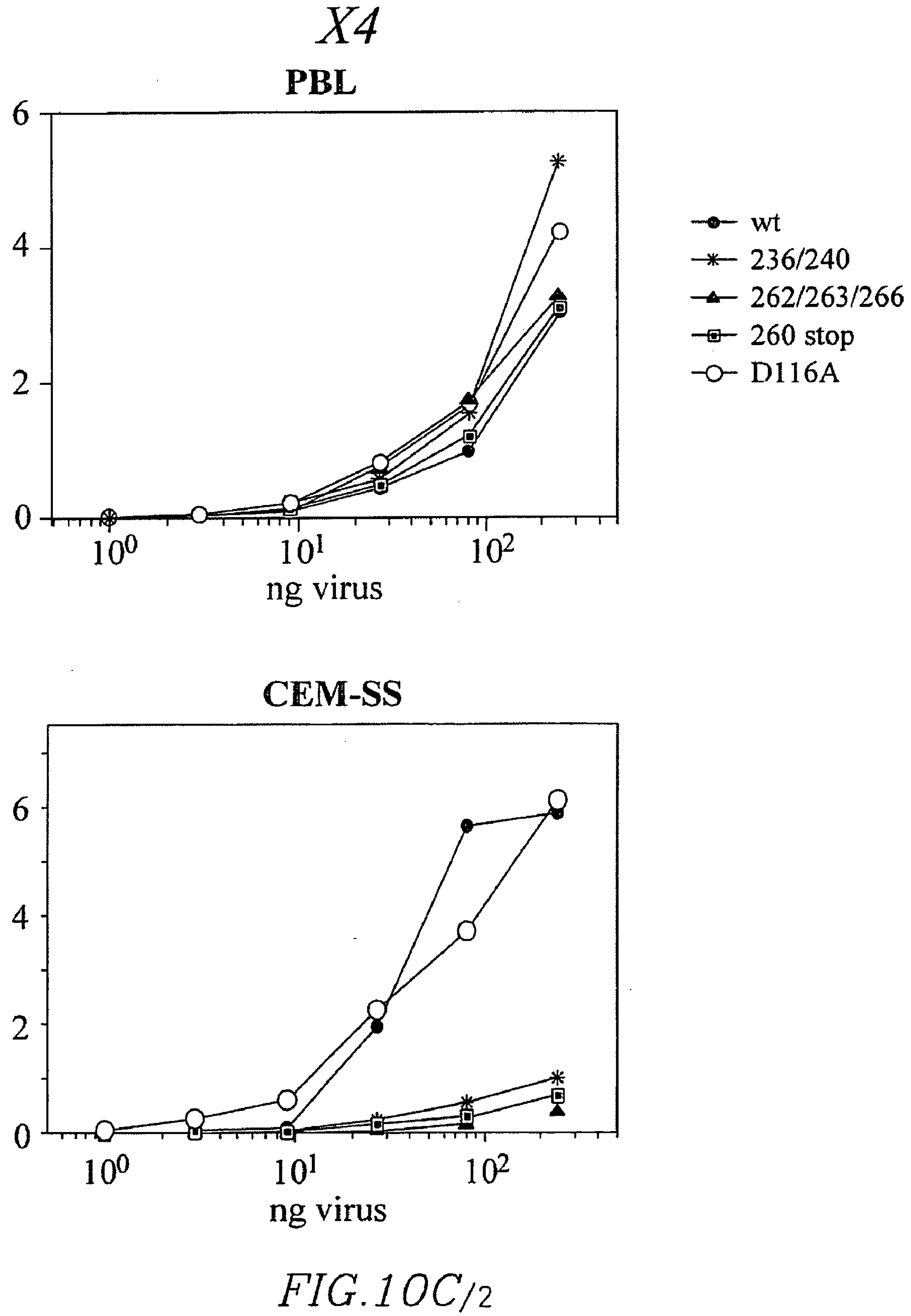
*FIG.10C/2*

| Region | Percent Transduced | |
|---|---|---|
| | Uninf | Infected |
| R3 | 0.27 | 2.52 |
| R4 | 0.1 | 0.66 |
| R5 | 0.0 | 0.11 |

53 56
TNTERPDTPTNTPN 60 63
TPTNTPNAPGRKSW (Class 2R)

200 203
ELKFHPRDPNLLLS (Class 1K)

```
        53  56
    TNTER P DT P TNTPN

        60  63
    TPTNT P NA P G R KSW (Class 2R)

        200  203
    EL K FH P RD P NLLLS (Class 1K)
```

SYNTHETIC NUCLEAR LOCALIZATION SIGNAL DERIVED FROM LENTIVIRAL INTEGRASE AND METHODS OF USE THEREOF

CROSS-REFERENCE TO RELATED APPLICATIONS

This Application claims the benefit of U.S. Provisional Application No. 60/532,563, filed Dec. 29, 2003, which is hereby incorporated in its entirety.

STATEMENT AS TO FEDERALLY SPONSORED RESEARCH

This invention was conducted with U.S. Government support under National Institutes of Health grant No. NIH (1R01 AI-47054) and an allocation from the Columbia-Rockefeller Center for AIDS Research (CR-CFAR) (funded by the National Institutes of Health (NIH)), CFAR (P30 AI42848). The government has certain rights in the invention.

FIELD OF THE INVENTION

This invention provides compounds and methods for modulating nuclear import. The present invention provides HIV-1 integrase-derived molecules that stimulate, accelerate, inhibit or abrogate nuclear import. The present invention also provides a peptide comprising a C-terminal Nuclear Localization Signal sequence of an HIV-1 integrase protein, or a fragment thereof, functioning in modulating nuclear import and methods utilizing same.

BACKGROUND OF THE INVENTION

After fusion and entry, the Human Immunodeficiency Virus (HIV-1) must navigate its genome through the cytosol and into the nucleus of its target cells, where integration into the host's chromosomal DNA subsequently occurs. Following the completion of reverse transcription, the genome of HIV-1 is contained in a large nucleoprotein complex operationally defined as the viral preintegration complex, or PIC. This assembly of viral RNA and/or DNA, and viral and cellular proteins is capable of traversing the cytoplasm, entering the nucleus, and targeting host chromatin. There, the viral integrase protein (IN), assisted by the action of host enzymes, catalyzes the insertion of viral DNA into that of the host and subsequent repair of the chromosomal interruptions created by the integration event itself The PIC, and the reverse transcription complexes that precede it in the viral life cycle likely constitute a series of structural and functional intermediates with changing composition. In fact, a variety of nucleoprotein complexes having discrete sedimentation velocities have been isolated from the cytoplasm and nucleus of HIV infected cells, at specific times post-infection. Not surprisingly, attempts to characterize in biochemical fashion the viral and cellular protein components of PICs have yielded disparate results. Integrase is consistently found as a constituent of the PIC, as would be expected for a viral protein that performs obligate catalyses on the viral DNA substrate in both the cytoplasm and nucleus. Other PIC-associated viral proteins include matrix (MA), Vpr, and, less frequently reported, nucleocapsid (NC), capsid (CA), and reverse transcriptase (RT).

A facilitating role in the nuclear import of the viral genome has been attributed to a number of PIC components, including MA, Vpr, IN, and the viral DNA itself Nevertheless, assignment and definition of the relative importance of each remains controversial. While some studies have implicated MA as a mediator of infection in non-dividing, others have shown that such an infection proceeds efficiently in the absence of either karyophilic determinants within MA or the majority of the MA protein. The ability of Vpr to interact with the nuclear pore complex has been well documented, and varying degrees of block to viral replication have been observed in its absence. Yet viruses lacking both Vpr and the karyophilic determinants of MA can still efficiently infect non-dividing cells. More recently, a facilitating role in PIC nuclear import has been attributed the central DNA flap—a discontinuity of the plus-strand of the HIV genome consisting of a short region of overlapping DNA and acting apparently in cis. Viruses lacking the central flap efficiently complete reverse transcription, but exhibit decreased nuclear import of viral DNA. Conversely, reconstitution of central DNA flap synthesis in lentiviral vectors that normally lack the structure increases their ability to transduce a variety of cell and tissue types in vitro and in vivo. However, recent experiments suggest that flap-deficient viruses can exhibit near wild-type levels of nuclear uptake under a variety of experimental conditions.

The final PIC component with reported karyophilic activity to date is integrase. Although an initial study characterized the intracellular localization of an IN-β-galactosidase fusion protein as cytoplasmic, further work using both transient transfection and in vitro nuclear import assays has shown that IN localizes predominantly to the nucleus. One study has reported that the mutations K186Q and Q214L/Q216L prevent the import of isolated IN or of other PIC-associated proteins (and presumably of the PIC itself) in assays performed in vitro, however, others have observed wild-type accumulation of nuclear forms of viral DNA in the presence of these mutations. In a more recent study, a peptide spanning amino acids 161-173 of IN was reported to act as a transferable NLS. Mutations at residues V165 and R166 abrogated the nuclear localization of an IN-pyruvate kinase fusion protein and, in the context of infection, impaired the accumulation of viral DNA in the nuclei of both dividing and non-dividing cells. Again, the interpretation of these results has been challenged and/or reassessed. Thus the precise mechanism of nuclear entry, as well as the identity of the cellular factors and viral determinants that are essential for it, remains elusive.

SUMMARY OF THE INVENTION

The invention provides, in one embodiment, a lentiviral nuclear localization signal, comprising an amino acid sequence corresponding to the formula: $R_5(R_6)_2FrVYR_1R_3R_2R_8R_3nplWR_3GPR_8kR_4R_5WR_3GEGA(R_4)_3R_6dR_6sR_6R_4kvR_4PR(R_3)_2R_8KIR_4R_3d$ wherein R1=an aromatic amino acid, R2=an acidic amino acid, R3=a basic amino acid, R4=a branched chain amino acid, R5=a hydrophobic amino acid, R6=a polar amino acid, R7=a proline or serine amino acid residue and R8=a small amino acid residue, lower case letters=the preferred amino acid residue, however substitutions with amino acid residues from disparate groups are possible as well.

In another embodiment, the lentiviral nuclear localization signal comprises an amino acid sequence corresponding to, or at least 75% homologous to SEQ ID NO: 139, 141, 147 or 149. In another embodiment, the lentiviral nuclear localization signal is encoded by a nucleic acid sequence at least 75% homologous to SEQ ID NO: 130, 132, 138 or 148. In another embodiment, the lentiviral nuclear localization signal comprises an amino acid sequence wherein amino acids at positions 3-10, 13-26, 29-34, 37-41 or 47-51, or a combination thereof, assume a β-pleated sheet conformation. In another embodiment, the β-pleated sheet conformation is stabilized by hydrophobic interactions among the amino acid residues of the sequence. In another embodiment, the amino acids at positions 43-45 assume an α-helical conformation. In another embodiment, the nuclear localization signal assumes a structure comprising SH3-like folds. In another embodiment, the nuclear localization signal comprises an amino acid sequence with hydrophobic amino acids at positions 1, 4, 6, 8, 16, 19, 29, 32, 41, 46, 48 or 49, or any combination thereof. In another embodiment, the hydrophobic amino acid residues are involved in maintaining an SH3 structure in the protein. In another embodiment, the nuclear localization signal comprises an amino acid sequence with amino acids at position 22, 23, 24, 29, 31, 38 or 40, or a combination thereof being involved in maintaining an SH3: SH3 dimer interface.

In another embodiment, this invention provides a recombinant protein comprising a lentiviral nuclear localization signal, comprising an amino acid sequence corresponding to the formula: $R_5(R_6)_2$ FrVY$R_1R_3R_2R_8R_3$npl$R_3$GP$R_8$k$R_4R_5$W$R_3$GEGA$(R_4)_3$ $R_6$d$R_6$s$R_6R_4$kv$R_4$PR$(R_3)_2R_8$KI$R_4R_3$d wherein R1=an aromatic amino acid, R2=an acidic amino acid, R3=a basic amino acid, R4=a branched chain amino acid, R5=a hydrophobic amino acid, R6=a polar amino acid, R7=a proline or serine amino acid residue and R8=a small amino acid residue, lower case letters=the preferred amino acid residue, however substutions with amino acid residues from disparate groups are possible as well.

In another embodiment, the lentiviral nuclear localization signal comprises an amino acid sequence corresponding to, or at least 75% homologous to SEQ ID NO: 139, 141, 147 or 149. In another embodiment, the lentiviral nuclear localization signal is encoded by a nucleic acid sequence at least 75% homologous to SEQ ID NO: 130, 132, 138 or 148. In another embodiment, the lentiviral nuclear localization signal comprises an amino acid sequence wherein amino acids at positions 3-10, 13-26, 29-34, 37-41 or 47-51, or a combination thereof, assume a β-pleated sheet conformation. In another embodiment, the β-pleated sheet conformation is stabilized by hydrophobic interactions among the amino acid residues of the sequence In another embodiment, the amino acids at positions 43-45, assume an α-helical conformation. In another embodiment, the nuclear localization signal assumes a structure comprising SH3-like folds. In another embodiment, the nuclear localization signal comprises an amino acid sequence with hydrophobic amino acids at positions 1, 4, 6, 8, 16, 19, 29, 32, 41, 46, 48 or 49, or any combination thereof In another embodiment, the hydrophobic amino acid residues are involved in maintaining an SH3 structure in the protein. In another embodiment, the nuclear localization signal comprises an amino acid sequence with amino acids at position 22, 23, 24, 29, 31, 38 or 40, or a combination thereof being involved in maintaining an SH3: SH3 dimer interface.

In another embodiment, this invention provides a mutated lentiviral nuclear localization signal. In one embodiment, the mutated lentiviral nuclear localization signal comprises an amino acid sequence at least 75% homologous to SEQ ID NO: 67-129, 139, 140, 141, 142, 143, 144, 145, 146 or 147. In another embodiment, the mutated lentiviral nuclear localization signal is encoded by a nucleic acid sequence at least 75% homologous to SEQ ID NO: 4-65, 130, 131, 132, 133, 134, 132, 136, 137, 138 or 146.

In another embodiment, this invention provides a recombinant protein comprising a mutated lentiviral nuclear localization signal. In one embodiment, the recombinant protein comprises a mutated lentiviral nuclear localization signal with an amino acid sequence corresponding to or homologous to SEQ ID NO: 67-129, 139, 140, 141, 142, 143, 144, 145, 146 or 147. In another embodiment, the recombinant protein comprises a mutated lentiviral nuclear localization signal encoded by a nucleic acid sequence corresponding to or homologous to SEQ ID NO: 4-65, 130, 131, 132, 133, 134, 132, 136, 137, 138 or 146.

In another embodiment, this invention provides an isolated polynucleotide encoding for a lentiviral nuclear localization signal, comprising an amino acid sequence corresponding to the formula: $R_5(R_6)_2$ FrVY$R_1R_3R_2R_8R_3$nplW$R_3$GP$R_8$k$R_4R_5$W$R_3$GEGA$(R_4)_3$ $R_6$dR6s$R_6R_4$kv$R_4$PR$(R_3)_2R_8K_1R_4R_3$d wherein R1=an aromatic amino acid, R2=an acidic amino acid, R3=a basic amino acid, R4=a branched chain amino acid, R5=a hydrophobic amino acid, R6=a polar amino acid, R7=a proline or serine amino acid residue and R8=a small amino acid residue, lower case letters=the preferred amino acid residue, however substutions with amino acid residues from disparate groups are possible as well.

In one embodiment, the isolated polynucleotide encodes for a lentiviral nuclear localization signal, comprising an amino acid sequence at least 75% homologous to SEQ ID NO: 139, 141, 147 or 149. In another embodiment, the isolated polynucleotide comprises a nucleic acid sequence at least 75% homologous to SEQ ID NO: 130, 132, 138 or 148.

In another embodiment, this invention provides an isolated polynucleotide encoding for a mutated lentiviral nuclear localization signal. In one embodiment, the isolated polynucleotide encodes for a lentiviral nuclear localization signal, comprising encoding for a mutated lentiviral nuclear localization signal, comprising an amino acid sequence homologous to SEQ ID NO: 67-129, 139, 140, 141, 142, 143, 144, 145, 146 or 147. In another embodiment, the isolated polynucleotide comprises a nucleic acid sequence homologous to SEQ ID NO: 4-65, 130, 131, 132, 133, 134, 132, 136, 137, 138 or 146.

In another embodiment, the invention provides a method of targeting an agent to the nucleus of a cell, comprising the steps of contacting a cell with a lentiviral nuclear localization signal, wherein said lentiviral nuclear localization signal is covalently attached to said agent and culturing said cell under conditions facilitating nuclear import, thereby targeting an agent to the nucleus of a cell.

In another embodiment, this invention provides a method of targeting a protein of interest to the nucleus of a cell, comprising the steps of contacting a cell with a vector, comprising a nucleic acid encoding a lentiviral nuclear localization signal, wherein said nucleic acid encoding a lentiviral nuclear localization signal is fused in frame to a nucleic acid encoding a protein of interest, thereby targeting a protein of interest to the nucleus of a cell.

In another embodiment, this invention provides a method of targeting a protein of interest to the nucleus of a cell, comprising the steps of contacting a cell with a viral particle, comprising a nucleic acid encoding a lentiviral nuclear localization signal, wherein said nucleic acid encoding a lentiviral nuclear localization signal is fused in frame to a nucleic acid encoding a protein of interest, thereby targeting a protein of interest to the nucleus of a cell.

In another embodiment, this invention provides a method of regulating gene expression in a cell, comprising the steps contacting a cell with a vector, comprising a nucleic acid encoding a lentiviral nuclear localization signal, wherein said nucleic acid encoding a lentiviral nuclear localization signal is fused in frame to a nucleic acid encoding an agent that regulates gene expression, under conditions favoring expression of said vector thereby regulating gene expression in a cell.

In another embodiment, this invention provides a method of enhancing expression of a lieterologous gene of interest in a cell, comprising the steps of contacting a cell with a vector comprising a nucleic acid encoding a lentiviral nuclear localization signal, wherein said nucleic acid encoding a lentiviral nuclear localization signal is fused in frame to a nucleic acid encoding a heterologous gene of interest, whereby expression of said lentiviral nuclear localization signal results in said heterologous gene of being imported into the cell nucleus, thereby enhancing expression of a heterologous gene of interest in a cell.

In another embodiment, this invention provides a method of stimulating or enhancing cell death, comprising contacting a cell with a complex comprising a lentiviral nuclear localization signal covalently attached to a cytotoxic agent, wherein following nuclear import of said complex said cytotoxic agent stimulates cell death, thereby stimulating or enhancing cell death.

In another embodiment, this invention provides a method of targeted cell death, comprising contacting a cell with a viral particle comprising a nucleic acid encoding a lentiviral nuclear localization signal, fused in frame to a nucleic acid encoding for a cytotoxic protein and a targeting moiety expressed on said viral particle surface wherein said targeting moiety directs said viral particle to a cell of interest, whereby said nucleic acid is expressed in the cytoplasm of said cell of interest, and following nuclear import of said lentiviral nuclear localization signal to said cytotoxic protein cell death is stimulated, thereby accomplishing targeted cell death.

In another embodiment, this invention provides a method of inhibiting or abrogating HIV proviral integration, comprising contacting an HIV infected cell with a vector or viral particle comprising at least one copy of a nucleic acid encoding an integrase wherein said integrase comprises a mutated lentiviral nuclear localization signal, whereby said mutated integrase competes for the HIV integrase present in said infected cell, preventing proviral nuclear entry, thereby inhibiting or abrogating proviral integration.

In another embodiment, this invention provides a method of inhibiting or abrogating HIV pathogenesis or disease progression, comprising contacting an HIV infected cell with a vector or viral particle comprising at least one copy of a nucleic acid encoding an integrase wherein said integrase comprises a mutated lentiviral nuclear localization signal, whereby said mutated integrase competes for the HIV integrase present in said infected cell, preventing proviral nuclear entry, thereby inhibiting or abrogating HIV pathogenesis or disease progression.

In another embodiment, this invention provides a method of inhibiting or abrogating HIV latency, comprising contacting an HIV infected cell with a vector or viral particle comprising at least one copy of a nucleic acid encoding an integrase wherein said integrase comprises a mutated lentiviral nuclear localization signal, whereby said mutated integrase competes for the HIV integrase present in said infected cell, thereby inhibiting or abrogating HIV latency.

In another embodiment, this invention provides a method of inhibiting or abrogating HIV pathogenesis or disease progression, comprising contacting an HIV infected cell with an inhibitor of a lentiviral nuclear localization signal, whereby said inhibitor prevents nuclear entry of HIV provirus, thereby inhibiting or abrogating HIV pathogenesis or disease progression.

In another embodiment, this invention provides a method of inhibiting or abrogating HIV latency, comprising contacting an HIV infected cell with an inhibitor of a lentiviral nuclear localization signal, whereby said inhibitor prevents nuclear entry of HIV integrase or derivatives thereof or of the HIV provirus, thereby inhibiting or abrogating HIV latency.

In another embodiment, this invention provides a method of inhibiting or abrogating HIV pathogenesis or disease progression, comprising contacting an HIV infected cell with an nucleic acid sequence complementary to a lentiviral nuclear localization signal, or a figment thereof, whereby said nucleic acid sequence inhibits expression or promotes degradation of an HIV integrase nuclear localization signal, preventing nuclear entry of HIV provirus, thereby inhibiting or abrogating HIV pathogenesis or disease progression.

In another embodiment, this invention provides a method of inhibiting or abrogating HIV latency, comprising contacting an HIV infected cell with a nucleic acid sequence complementary to a lentiviral nuclear localization signal, or a fragment thereof, whereby said nucleic acid sequence inhibits expression or promotes degradation of an HIV integrase nuclear localization signal, preventing nuclear entry of HIV integrase or derivatives thereof or of the HIV provirus, thereby inhibiting or abrogating HIV latency.

In another embodiment, this invention provides a method of screening for an agent that inhibits HIV nuclear import comprising contacting an HIV integrase protein with a candidate agent and determining HIV PIC nuclear import, wherein lack of HIV PIC nuclear import indicates that said candidate agent inhibits HIV nuclear import.

BRIEF DESCRIPTION OF THE DRAWINGS

FIG. 2 schematically depicts the results of a survey of 540 sequences demonstrating conservation of the SH3 domain and NLS in primate lentiviruses as compared to an exemplary amino acid sequence set forth as SEQ ID NO:147. Conservation of residues involved in beta-pleated sheet formation, are as indicated. The amino acid sequence corresponding to the formula is set forth as SEQ ID NO:150

FIG. 3 schematically depicts the frequency of substitution of specific amino acid residues in amino acids 220-270 of HIV integrase (SEQ ID NO:147), in 520 HIV independent proviral DNA sequences evaluated.

FIG. 5 indicates the amino acid substitutions at the indicated residues identified in the 520 HIV independent proviral DNA sequences evaluated as compared to an exemplary amino acid sequence set forth as SEQ ID NO:147.

DETAILED DESCRIPTION OF THE INVENTION

Figure 1A:
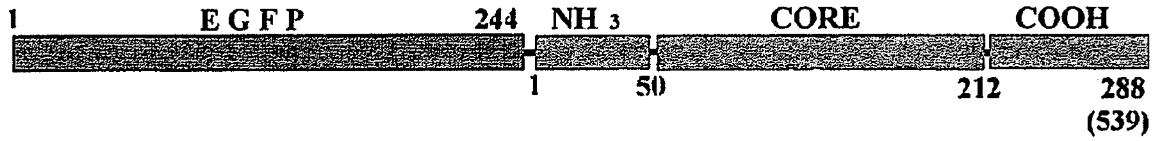
FIG. 1 demonstrates that mutations in the carboxyl-terminal domain of HIV-1 integrase abrogate its nuclear localization Carboxyl-terminal deletion mutants of EGFP-IN, with IN fused to the carboxyl-terminus of EGFP via a 7 amino acid linker (SGLRSMG set forth as SEQ ID NO:151) protein connecting the two. The 3-domain structure of IN is shown (A). Nucleocytoplasmic distribution of wild-type and IN carboxyl-terminal deletion mutants (B). 293 cells were transfected with the indicated EGFP-IN expression construct and the subcellular localization of the fusion protein visualized 24 hours later by deconvolution microscopy. Subcellular localization was confirmed by counterstaining nuclei with DAPI (not shown). Carboxyl-Terminal NLS mutations in the context of native integrase are shown by Northern blot analysis of wild-type and synthetic IN open reading frames (C). Twenty-four hours after transfection of 293T cells, total RNA was isolated and probed with the radiolabeled CTE fragment, a region of mRNA identical to both viral and codon-modified transcripts. Ethidium bromide stained gel before transfer (upper) and autoradiogram (lower), where Lane 1, mock transfected; lane 2, pcDNA3.1. (+) IN-VIR; and lane 3, pcDNA3.1 (+) IN-MOD. Comparative western blot analysis of IN produced from wild-type and synthetic open reading frames (D). Total cell lysates were probed with a monoclonal antibody directed to the central core domain of integiase (lane identity is the same as in C). Subcellular localization of native wild-type integrase and its NLS-mutants (E). 293T cells were transfected with the indicated expression construct. After transfection, cells were stained immunocytochemically and visualized by deconvolution microscopy. Native nucleotide sequences for the integrase coding region, the native amino acid sequence, and a listing of the mutants generated is schematically depicted (F).

This invention provides, in one embodiment, novel peptides, nucleic acids, compositions and methods for regulating nuclear import, and therapeutic applications arising from their utilization, in a myriad of pathologies unavailable in the state of the art to date. The invention also provides screening methods for identifying agents for regulating nuclear import. The following are meant to provide materials, methods, and examples for illustrative purposes as a means of practicing/executing the present invention, and are not intended to be limiting.

After the completion of reverse transcription, lentiviral genomes, and in particular, HIV-1 is contained in a large nucleoprotein complex operationally defined as the viral pre-integration complex (PIC). This assembly of viral RNA and/or DNA, and viral and cellular proteins traverses the cytoplasm, enters the nucleus, and targets host chromatin, where the viral integrase protein (IN), assisted by the action of host enzymes, catalyzes the insertion of viral DNA into that of the host. In the present invention, a region in the C-terminal domain of HIV integrase is demonstrated to be responsible for nuclear localization of the PIC (Example 1). The region comprises basic residues, which are highly conserved among various lentiviridae.

Lentiviral NLS:

The invention provides, in one embodiment, a lentiviral nuclear localization signal (NLS), comprising an amino acid sequence corresponding to the formula: $R_5(R_6)_2$ $FrVYR_1R_3R_2R_8R_3nplWR_3GPR_8kR_4R_5WR_3GEGA(R_4)_3$ $R_6dR_6sR_6R_4kvR_4PR(R_3)_2R_8KIR_4R_3d$ wherein R1=an aromatic amino acid, R2=an acidic amino acid, R3=a basic amino acid, R4=a branched chain amino acid, R5=a hydrophobic amino acid, R6=a polar amino acid, R7=a proline or serine amino acid residue and R8=a small amino acid residue, lower case letters=the preferred amino acid residue, however substutions with amino acid residues from disparate groups are possible as well. In one embodiment, the lentiviral nuclear localization signal, comprises an amino acid sequence at least 75% homologous to SEQ ID NO: 139, 147 or 149.

In another embodiment, the integrase nuclear localization signal will comprise at least two clusters of basic amino acid residues. The residues will, in one embodiment, be spaced at least 15, or, in another embodiment, at least 20, or in another embodiment, at least 25, or in another embodiment, at least 30, or in another embodiment, at least 35 or more resides apart. In another embodiment, the integrase nuclear localization signal comprising basic residues is in the context of an SH3-like, three-dimensional structural element.

In one embodiment, the lentiviral nuclear localization signal will comprise an overall SH3-like structure, and have the following residues conserved: K236, R262, R263, K266, and K240. In another embodiment, the amino acid sequence comprises hydrophobic amino acids at positions 1, 4, 6, 8, 16, 19, 29, 32, 41, 46, 48 or 49, or any combination thereof, which are involved in maintaining the SH3-like structure in the protein. In another embodiment, the amino acids at position 22, 23, 24, 29, 31, 38 or 40, or a combination thereof are involved in maintaining an SH3: SH3 dimer interface.

In another embodiment, the lentiviral nuclear localization signal will comprise a basic residue pattern, in the context of an SH3-like overall structure. In another embodiment, the amino acids at positions 3-10, 13-26, 29-34, 37-41 or 47-51 or a combination thereof, of the NLS, assume a β-pleated sheet conformation. In another embodiment, the β-pleated sheet conformation is stabilized by hydrophobic interactions among the amino acid residues of said sequence.

It is to be understood that any lentiviral nuclear localization signal, which exhibits homology to the sequences listed are considered as part of this invention.

In another embodiment, the nuclear localization signal may be derived from a retrovirus or lentivirus, such as for example, Moloney Leukemia Virus (MLV), Abelson murine leukemia virus, AKR (endogenous) murine leukemia virus, Avian carcinoma, Mill Hill virus 2, Avian leukosis virus—RSA, Avian myeloblastosis virus, Avian myelocytomatosis virus 29, Bovine syncytial virus, Caprine arthritis encephalitis virus, Chick syncytial virus, Equine infectious anemia virus, Feline leukemia virus, Feline syncytial virus, Finkel-Biskis-Jinkins murine sarcoma virus, Friend murine leukemia virus, Fujinami sarcoma virus, Gardner-Arnstein feline sarcoma virus, Gibbon ape leukemia virus, Guinea pig type C oncovirus, Hardy-Auckerman feline sarcoma virus, Harvey murine sarcoma virus, Human foamy virus, Human spumavirus, Human T-lymphotropic virus 1, Human T-lymphotropic virus 2, Jaagsiekte virus, Kirsten murine sarcoma virus, Langur virus, Mason-Pfizer monkey vikrus, Moloney murine sarcoma virus, Mouse mammary tumor virus, Ovine pulmonary adenocarcinoma virus, Porcine type C oncovirus, Reticuloendotheliosis virus, Rous sarcoma virus, Simian foamy virus, Simian sarcoma virus, Simian T-lymphotropic virus, Simian type D virus 1, Snyder-Theilen feline sarcoma virus, Squirrel monkey retrovirus, Trager duck spleen necrosis virus, UR2 sarcoma virus, Viper retrovirus, Visna/maedi virus, Woolly monkey sarcoma virus, and Y73 sarcoma virus human-, simian-, feline-, and bovine immunodeficiency viruses (HIV, SIV, FIV, BIV).

The term "homology", in one embodiment, when in reference to any protein or peptide of this invention, indicates a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology, Methods and computer programs for the alignment are well known in the art.

Protein and/or peptide homology for any amino acid sequence listed herein may be determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example.

In one embodiment, the term "protein", refers to any protein, peptide or amino acid sequence of this invention, which may include native peptides and amino acids (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminal, C terminal or peptide bond modification, including, but not limited to, backbone modifications, and residue modification, each of which represents an additional embodiment of the invention Methods for preparing peptidomimetic compounds are well known in the art and are specified, for example, in Quantitative Drug Design, C. A. Ramsden Gd., Chapter 17.2, F. Choplin Pergamon Press (1992).

It is to be understood that any amino acid sequence whether obtained naturally or synthetically, by any means, exhibiting sequence, structural, or functional homology to the peptides described herein are considered as part of this invention.

Methods for the detection of the proteins or peptides of this invention are well known in the art, and may comprise, for example, HPLC, Mass Spectroscopy, ELISA, RIA or Western blot analysis [see "Cell Biology: A Laboratory Handbook", Volumes I-III Cellis, J. E., ed. (1994); "Current Protocols in Immunology" Volumes I-III Coligan J. E., ed. (1994); Stites et al. (eds)].

Some of the methods rely upon antibody detection of lentiviral NLS, and as described further hereinbelow, may also be utilized for detection of mutated lentiviral NLSs. In one embodiment, affinity purified polyclonal antibody against recombinant proteins of this invention can be generated. Typically, a suitable subject, (e.g., rabbit, goat, mouse or other mammal) is immunized with an immunogenic preparation of the recombinant proteins of this invention. In another embodiment, an appropriate immunogenic preparation containing chemically synthesized lentiviral NLS is utilized. The preparation can further include an adjuvant, such as Freund's complete or incomplete adjuvant, or similar immunostimulatory agent. Immunization of a suitable subject with an immunogenic preparation induces a polyclonal antibody response, and monoclonal antibodies may also be prepared, by methods described extensively in the art.

Isolated Nucleic Acids/Expression Contstructs Encoding for a Lentiviral NLS:

In another embodiment, the lentiviral nuclear localization signal is encoded by a nucleic acid sequence at least 75% homologous to SEQ ID NO: 130, 138 or 148.

In one embodiment, the terms "homology", "homologue" or "homologous", in any instance, indicate that the sequence referred to, whether an amino acid sequence, or a nucleic acid sequence, exhibits at least 70% correspondence with the indicated sequence. In another embodiment, the amino acid sequence or nucleic acid sequence exhibits at least 72% correspondence with the indicated sequence. In another embodiment, the amino acid sequence or nucleic acid sequence exhibits at least 75% correspondence with the indicated sequence. In another embodiment, the amino acid sequence or nucleic acid sequence exhibits at least 77% correspondence with the indicated sequence In another embodiment, the amino acid sequence or nucleic acid sequence exhibits at least 80% correspondence with the indicated sequence. In another embodiment, the amino acid sequence or nucleic acid sequence exhibits at least 82% correspondence with the indicated sequence. In another embodiment, the amino acid sequence or nucleic acid sequence exhibits at least 85% correspondence with the indicated sequence. In another embodiment, the amino acid sequence or nucleic acid sequence exhibits at least 87% correspondence with the indicated sequence. In another embodiment, the amino acid sequence or nucleic acid sequence exhibits at least 90% correspondence with the indicated sequence. In another embodiment, the amino acid sequence or nucleic acid sequence exhibits at least 92% correspondence with the indicated sequence. In another embodiment, the amino acid sequence or nucleic acid sequence exhibits at least –95% or more correspondence with the indicated sequence. In another embodiment, the amino acid sequence or nucleic acid sequence exhibits 95% -100% correspondence to the indicated sequence. Similarly, as used herein, the reference to a correspondence to a particular sequence includes both direct correspondence, as well as homology to that sequence as herein defined.

In one embodiment, the term "homology", when in reference to any nucleic acid sequence indicates a percentage of nucleotides in a candidate sequence that are identical with the nucleotides of a corresponding native nucleic acid sequence.

Homology may be determined in the latter case by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

An additional means of determining homology is via determination of candidate sequence hybridization, methods of which are well described in the art (See, for example, "Nucleic Acid Hybridization" Hames, B. D., and Higgins S. J., Eds. (1985); Sambrook et al., 1989, Molecular Cloning, A Laboratory Manual, (Volumes 1-3) Cold Spring Harbor Press, N.Y.; and Ausubel et al., 1989, Current Protocols in Molecular Biology, Green Publishing Associates and Wiley Interscience, N.Y.). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5× Denhardt's solution, 10% dextran sulfate, and 20 μg/ml denatured, sheared salmon sperm DNA.

In another embodiment, this invention provides a vector comprising a nucleic acid encoding for the lentiviral nuclear localization signal of this invention. In one embodiment, the term "vector" refers to a nucleic acid construct containing a sequence of interest that has been subcloned within the vector. In one embodiment, the nucleic acid sequence encodes for a lentiviral nuclear localization signal or a functional fragment thereof.

To generate the vectors of the present invention, polynucleotides encoding a lentiviral nuclear localization signal arid other sequences of interest can be ligated into commercially available expression vector systems suitable for transducing/transforming eukaryotic or prokaryotic cells and for directing the expression of recombinant products within the transduced/transformed cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter genes.

According to another embodiment, nucleic acid vectors comprising the isolated nucleic acid sequences encoding for the protein of interest include a regulatory element, such as a promoter for regulating expression of the isolated nucleic acid. Such promoters are known to be cis-acting sequence elements required for transcription as they serve to bind DNA dependent RNA polymerase, which transcribes sequences present downstream thereof.

The vector may, in another embodiment, comprise an inducible promoter, or one that expresses the sequences of interest constitutively.

Nucleotide sequences which regulate expression of a gene product, which are in one embodiment, promoter and enhancer sequences, are selected, in another embodiment, based upon the type of cell in which the gene product is to be expressed, or in another embodiment, upon the desired level of expression of the gene product, in cells infected with the vectors of the invention. According to this aspect of the invention, the gene product corresponds to the heterologous protein, as described herein. Regulated expression of such a heterologous protein may thus be accomplished, in one embodiment.

For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements which are known in the art include upstream regions from the dystrophin gene (Klamut et al., (1989) Mol. Cell Biol. 9:2396), the creatine kinase gene (Buskin and Hausclika, (1989) Mol. Cell Biol. 9:2627) and the troponin gene (Mar and Ordahl, (1988) Proc. Natl. Acad. Sci. USA. 85:6404).

Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters). In another embodiment, a regulatory element, which can direct constitutive expression of a gene in a variety of different cell types, such as a viral regulatory element, can be used. Examples of viral promoters commonly used to drive gene expression include those derived from polyoma virus, Adenovirus 2, cytomegalovirus and Simian Virus 40, and retroviral LTRs.

In another embodiment, a regulatory element, which provides inducible expression of a gene linked thereto can be used. The use of an inducible regulatory element (e.g., an inducible promoeter) allows for modulation of the production of the gene product in the cell. In another embodiment, the inducible regulatory systems for use in eukaryotic cells include hormone-regulated elements (e.g., see Mader, S. and White, J. H. (1993) Proc. Natl. Acad. Sci. USA 90:5603-5607), synthetic ligand-regulated elements (see, e.g., Spencer, D. M. et al 1993) Science 262:1019-1024) and ionizing radiation-regulated elements (e.g., see Manome, Y. Et al. (1993) Biochemistry 32:10607-10613; Datta, R. et al. (1992) Proc. Natl. Acad. Sci. USA 89:1014-10153). Additional tissue-specific or inducible regulatory systems, may be developed for use in accordance with the invention.

A vector according to the present invention, may, in another embodiment further include an appropriate selectable marker. The vector may further include an origin of replication, and may be a shuttle vector, which can propagate both in prokaryotic, and in eukaryotic cells, or the vector may be constructed to facilitate its integration within the genome of an organism of choice. The vector, in other embodiments may be, for example, a plasmid, a bacmid, a phagemid, a cosmid, a phage, a virus or an artificial chromosome. In another embodiment, the vector is a viral particle comprising the nucleic acids of the present invention. In another embodiment, this invention provides liposomes comprising the nucleic acids and vectors of this invention. Methods for preparing such liposomes are well known in the art, and may be as described in, for example WO 96/18372; WO 93/24640; Mannino and Gould-Fogerite (1988) BioTechniques 6(7): 682-691; Rose U.S. Pat. No. 5,279,833; WO 91/06309; and Feigner et al. (1987) Proc. Natl. Acad. Sci. USA 84: 7413-7414).

In another embodiment, this invention provides cells comprising the nucleic acids and vectors of this invention. In one embodiment, the cells are prokaryotic, or in another embodiment, the cells are eukaryotic. Cells may be any cells capable of expressing the isolated nucleic acids and/or vectors of this invention, as will be known to one skilled in the art, with some examples as provided herein. In one embodiment, the cells are terminally differentiated, or, in another embodiment, non-dividing. In another embodiment, the cells are dividing.

In another embodiment, this invention provides compositions comprising the nucleic acids and vectors of this invention. The effective dose and method of administration of a particular composition formulation can vary based on the particular application. Dosage may vary as a function of the type of vector, for example, employed and the route of administration.

Routes of administration of the nucleic acids, vectors, recombinant proteins, liposomes, and compositions of the invention include, but are not limited to oral or local administration, such as by aerosol, intramuscularly or transdermally, and parenteral application. Compositions can be administered in a variety of unit dosage forms depending upon the method of administration. Suitable unit dosage forms, include, but are not limited to powders, tablets, pills, capsules, lozenges, suppositories, etc. Transdermal administration may be accomplished by application of a cream, rinse, gel, etc. capable of allowing the active compounds to penetrate the sldn. Parenteral routes of administration may include, but are not limited to, electrical or direct injection such as direct injection into a central venous line, intravenous, intramuscular, intraperitoneal, intradermal, or subcutaneous injection.

Nucleic acid sequences encoding for lentiviral nuclear localization signals may be utilized as described, in the present invention. As used herein, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotides. This term includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for nucleic acid target and increased stability in the presence of nucleases.

As will be appreciated by one skilled in the art, a fragment or derivative of a nucleic acid sequence or gene that encodes for a protein or peptide can still function in the same manner as the entire, wild type gene or sequence. Likewise, forms of nucleic acid sequences can have variations as compared to wild type sequences, nevertheless encoding the protein or peptide of interest, or fragments thereof, retaining wild type function exhibiting the same biological effect, despite these variations. Each of these represents a separate embodiment of this present invention.

The nucleic acids of this invention can be produced by any synthetic or recombinant process such as is well known in the art. Nucleic acids can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences.

DNA according to the invention can also be chemically synthesized by methods known in the art. For example, the DNA can be synthesized chemically from the four nucleotides in whole or in part by methods known in the art. Such methods include those described in Caruthers (1985). DNA can also be synthesized by preparing overlapping double-stranded oligonucleotides, filling in the gaps, and ligating the ends together (see, generally, Sambrook et al. (1989) and Glover et al. (1995)). DNA expressing functional homologues of the protein can be prepared from wild-type DNA by site-directed mutagenesis (see, for example, Zoller et al. (1982); Zoller (1983); and Zoller (1984); McPherson (1991)). The DNA obtained can be amplified by methods known in the art. One suitable method is the polymerase chain reaction (PCR) method described in Saiki et al. (1988), Mullis et al., U.S. Pat. No. 4,683,195, and Sambrook et al. (1989).

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. Variations in the DNA sequences, which are caused by point mutations or by induced modifications (including insertion, deletion, and substitution) to enhance the activity, half-life or production of the polypeptides encoded thereby, are also encompassed in the invention.

In another embodiment, this invention provides compositions or cells comprising the vectors of this invention. In another embodiment, this invention provides a viral particle, liposome, cell or composition comprising a nucleic acid encoding for the lentiviral nuclear localization signal of this invention.

Compositions of this invention may comprise lotions, ointments, gels, creams, suppositories, drops, liquids, sprays, powders or granules, suspensions or solutions in water or non-aqueous media, sachets, capsules or tablets. Thickeners, carriers, buffers, diluents, surface active agents, preservatives, flavorings, dispersing aids, emulsifiers or binders may also be included, all as well other suitable additives, all of which are well known in the art comprise agents that may be ingredients of the compositions of this invention.

Cells of this invention may be prokaryotic or eukaryotic, and may be utilized, in one embodiment, for scaled up growth of the vectors of this invention, or, in another embodiment, may be used as delivery vehicles. It is to be understood that any means of obtaining the nucleic acids of this invention, and its delivery are considered as part of this invention, and represent additional embodiments thereto.

In another embodiment, the isolated nucleic acids, vectors, viral particles, liposomes, cells and/or compositions of this invention my further comprise a second nucleic acid. In one embodiment, the second nucleic acid sequence encodes for a protein of interest. In one embodiment, the protein of interest is translated as a fusion protein with the lentiviral nuclear localization signal.

Therapeutic Protein Expression via the Use of a Lentiviral NLS:

In one embodiment, the protein of interest is therapeutic. In another embodiment, the therapeutic protein is a co-stimulatory molecule, cytokine or chemokine.

In one embodiment, the term "therapeutic" refers to the fact that expression of the heterologous protein, when expressed in a subject in need, provides a beneficial effect. In some cases, the protein is therapeutic in that it functions to replace a lack of expression or lack of appropriate expression of such a protein in a subject. Some examples include cases where the expression of the protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein.

In one embodiment, the therapeutic protein expressed may include cytokines, such as interferons or interleukins, or their receptors. Lack of expression of cytolcines has been implicated in susceptibility to diseases, and enhanced expression may lead to resistance to a number of infections. Expression patterns of cytokines may be altered to produce a beneficial effect, such as for example, a biasing of the immune response toward a Th1 type expression pattern, or a Th2 pattern in infection, or in autoimmune disease, wherein altered expression patterns may prove beneficial to the host.

In another embodiment, the therapeutic protein expressed may include an enzyme, such as one involved in glycogen storage or breakdown. In another embodiment, the therapeutic protein expressed may include a transporter, such as an ion transporter, for example CFTR, or a glucose transporter, or other transporters whose deficiency, or inappropriate expression results in a variety of diseases.

In another embodiment, the therapeutic protein expressed may include a receptor, such as one involved in signal transduction within a cell. Some examples include as above, cytokine receptors, leptin receptors, transferring receptors, etc., or any receptor wherein its lack of expression, or altered expression results in inappropriate or inadequate signal transduction in a cell.

In another embodiment, the therapeutic protein expressed may include a tumor suppressor gene, or a proapoptotic gene, whose expression alters progression of intracellular cancer-related events. For example, p53 may be expressed in cells that demonstrate early neoplastic events, thereby suppressing cancer progression.

In another embodiment, the therapeutic protein expressed may be selected from the group consisting of natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, omithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the α family, transforming growth factors of the β family, gastrins, secretins, cholecystokinins, somatostatins, serotonins, substance P and transcription factors.

In another embodiment, the therapeutic protein is an angiogenic factor, an angiogenesis inhibitor, an ionophore, an inhibitor of microtubules or a cell cycle inhibitor.

Immunogenic Protein Expression via the Use of Lentiviral NLS:

In another embodiment, the protein of interest is immunogenic. Immunogenic proteins are, in one embodiment, proteins stimulating a specific immune response that once initiated provides a beneficial outcome in a host. In one embodiment, the response results in eradication of a disease. In another embodiment, the response results in the halting of disease progression. In another embodiment, the response results in the prevention of infection. In another embodiment, the response results in amelioration of disease symptoms. In another embodiment, the response results in inhibition or abrogation of disease latency. It is to be understood that any positive and beneficial outcome due to stimulation of the immune response as a result of the introduction of a vector of this invention in a host is to be considered as part of this invention.

In another embodiment, immunogenic proteins of this invention bias the adaptive immune response. In one embodiment, the immune response is biased toward a Th1 type response. In one embodiment, "Th1 type response" refers to a pattern of cytokine expression, elicited by T Helper cells as part of the adaptive immune response, which support the development of robust cell-mediated immunity. In one embodiment, Th1 type responses are beneficial in intracellular infections in a subject. In another embodiment, Th1 type responses are recognized by the production of interleukin-2 or interferon γ.

In another embodiment, the immune response is biased toward a Th2 type response. In one embodiment, "Th2 type response" refers to a pattern of cytokine expression, elicited by T Helper cells as part of the adaptive immune response, which support the development of a robust antibody response. In one embodiment, Th2 type responses are beneficial in helminth infections in a subject. In another embodiment, Th2 type responses are recognized by the production of interleukin-4 or interleukin 10.

In another embodiment, the immunogenic protein or polypeptide elicits a "Th1" response, in a disease where a so-called "Th2" type response has developed, when the development of a so-called "Th1" type response is beneficial to the subject. Introduction of the immunogenic protein or polypeptide results in a shift toward a Th1 type response. One example would be in leprosy, where the vectors, viral particles, liposomes, cells or compositions of the present invention express an antigen from M. leprae, where the antigen stimulates a Th1 cytokine shift, resulting in tuberculoid leprosy, as opposed to lepromatous leprosy, a much more severe form of the disease, associated with Th2 type responses.

In another embodiment, a Th1 type response has developed, when Th2 type responses provide a more beneficial outcome to a subject, where introduction of the immunogenic protein or polypeptide via the vectors, viral particles, liposomes, cells or compositions of the present invention provides a shift to the more beneficial cytokine profile.

In another embodiment, attenuating molecules are provided in the vectors, viral particles, liposomes, compositions and/or cells of the present invention. In another embodiment, the proteins of this invention when expressed result in the downregulation of the immune response, or in another embodiment, result in T cell anergy. Such a scenario may be utilized, in one embodiment, as a means of inhibiting or abrogating an autoimmune response, or an inflammatory response.

Regulating Gene Expression Via the Use of a Lentiviral NLS:

In one embodiment, the protein of interest regulates gene expression. In another embodiment, the protein regulates gene expression by stimulating or enhancing transcription of the gene. In another embodiment, the protein of interest regulates gene expression by repressing or diminishing transcription of the gene.

In another embodiment, this invention provides a method of regulating gene expression in a cell, comprising the steps of contacting a cell with a vector, comprising a nucleic acid encoding a lentiviral nuclear localization signal, wherein the nucleic acid encoding a lentiviral nuclear localization signal is fused in frame to a nucleic acid encoding an agent that regulates gene expression, under conditions favoring expression of the vector, thereby regulating gene expression in a cell.

In another embodiment, this invention provides a method of enhancing expression of a heterologous gene of interest in a cell, comprising the steps of contacting a cell with a vector comprising a nucleic acid encoding a lentiviral nuclear localization signal, wherein the nucleic acid encoding a lentiviral nuclear localization signal is fused in frame to a nucleic acid encoding a heterologous gene of interest, whereby expression of the lentiviral nuclear localization signal results in the heterologous gene of interest being imported into the cell nucleus, thereby enhancing expression of a heterologous gene of interest in a cell.

In one embodiment, the agent that regulates gene expression stimulates or enhances gene expression. In one embodiment, the agent is a transcriptional activator. In another embodiment, the agent that regulates gene expression diminishes or abrogates gene expression. In one embodiment, the agent is a repressor.

Targeting of a Heterologous Protein Via the Use of a Lentiviral NLS:

In another embodiment, targeting a protein of interest to the nucleus of a cell can be accomplished via the use of the nucleic acids, vectors, viral particles, liposomes, cells and compositions of this invention. In one embodiment, the vectors/viral particles/cells of this invention comprise a nucleic acid encoding for a nucleic acid encoding a protein of interest fused in frame to the nucleic acid encoding the lentiviral nuclear localization signal. In another embodiment, the vectors/viral particles/cells of this invention comprise a nucleic acid encoding for a detectable marker fused in frame to the nucleic acid encoding a protein of interest at a site distal to that of the nucleic acid encoding the lentiviral nuclear localization signal.

In one embodiment, this invention provides a method of targeting a nucleic acid or protein of interest to the nucleus of a cell, comprising the steps of contacting a cell with a vector, comprising a nucleic acid encoding a lentiviral nuclear localization signal, wherein said nucleic acid encoding a lentiviral nuclear localization signal is fused in frame to a nucleic acid encoding a protein of interest, thereby targeting a nucleic acid or protein of interest to the nucleus of a cell. In another embodiment, this invention provides a method of targeting a nucleic acid or protein of interest to the nucleus of a cell, comprising the steps of contacting a cell with a viral particle or cell, comprising a nucleic acid encoding a lentiviral nuclear localization signal, wherein said nucleic acid encoding a lentiviral nuclear localization signal is fused in flame to a nucleic acid encoding a protein of interest, thereby targeting a nucleic acid or protein of interest to the nucleus of a cell.

In one embodiment, the term "contacting a target cell" refers to direct and/or indirect exposure of the target cell to a virus, nucleic acid, vector or composition of the invention In one embodiment, contacting a cell may comprise direct injection of the cell through any means well known in the art, such as microinjection. It is also envisaged, in another embodiment, that supply to the cell is indirect, such as via provision in a culture medium that surrounds the cell.

In one embodiment, the target cell is a resting cell. In another embodiment, the target cell is a slowly dividing cell. In another embodiment, the cell is activated. In another embodiment, the target cell readily proliferates. In another embodiment, the cell is non-dividing.

According to this aspect of the invention, in additional embodiments, the target cell is an epithelial cell, a lung cell, a kidney cell, a liver cell, a pancreatic cell, a neuron, a chondrocyte, an osteocyte, an astrocyte, an endothelial cell, a cardiocyte, a myocyte, a cardiomyocyte, a retinal cell, an immune cell, a glial cell, a stem cell or an M cell.

In one embodiment, the target cell is contacted in vivo, or, in another embodiment, in vitro. In another embodiment, the cell is contacted ex vivo, and is then implanted into an appropriate host.

In another embodiment, targeting the therapeutic protein ameliorates or abrogates a disease in a subject. According to this aspect of the invention, the disease for which the subject is thus treated may comprise, but is not limited to: muscular dystrophy, cancer, cardiovascular disease, hypertension, infection, renal disease, neurodegenerative disease, such as alzlieimer's disease, parkinson's disease, huntington's chorea, Creuztfeld-Jacob disease, autoimmune disease, such as lupus, rheumatoid arthritis, endocarditis, Graves' disease or ALD, respiratory disease such as asthma or cystic fibrosis, bone disease, such as osteoporosis, joint disease, liver disease, disease of the skin, such as psoriasis or eczema, ophthalmic disease, otolaryngeal disease, other neurological disease such as Turret syndrome, schizophrenia, depression, autism, or stoke, or metabolic disease such as a glycogen storage disease or diabetes. It is to be understood that any disease whereby expression of a particular protein in a cell nucleus which can be accomplished via the use of the isolated nucleic acids, viral particles, vectors, liposomes or cells or compositions of this invention is sought, is to be considered as part of this invention.

Protocols for introducing the viruses, nucleic acids or vectors of the invention into target cells may comprise, for example: direct DNA uptake techniques, virus, plasmid, linear DNA or liposome mediated transduction, or transfection, magnetoporation methods employing calcium-phosphate mediated and DEAE-dextran mediated methods of introduction, electroporation, direct injection, and receptor-mediated uptake (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). It is to be understood that any direct means or indirect means of intracellular access of a virus, viral particle, nucleic acid or vector of the invention is contemplated herein, and represents an embodiment thereof.

In another embodiment, it may be desirable to target a therapeutic protein to a particular cell. In one embodiment, in addition to expression of a therapeutic protein, a targeting protein is expressed, such that the viral particles and cells of the invention are directed to specific sites, where expression of therapeutic proteins occurs.

In one embodiment, the targeting moiety may comprise an antibody or polypeptide fragment thereof, a bi-functional antibody, Fab, Fc, Fv, or single chain Fv (scFv) as their attachment protein. Such antibody fragments may be constructed, in another embodiment to identify and bind to a specific receptor or cell surface marker. In another embodiment, the antibody or fragment thereof may be constructed to bind to an antigen expressed on a cell surface, as a result of infection or, in another embodiment, transformation of the cell. These antibodies can, in another embodiment, be humanized, human, or chimeric antibodies (for discussion and additional references see S. L. Morrison "Antibody Molecules, Genetic Engineering of," in MOLECULAR BIOLOGY AND BIOTECHNOLOGY: A COMPREHENSIVE DESK REFERENCE 1995; S. D. Gillies et aL, (1990) Hum. Antibod. Hybridomas 1 (1): 47-54; E. HARLOW AND D. LANE, ANTIBODIES: A LABORATORY MANUAL (1988) Cold Spring Harbor Press, NY). Expression of functional single chain antibodies on the surface of viruses has been reported using Vaccinia virus (M. C. Galmiche et aL, (1997) J. Gen. Virol. 78: 3019-3027). Similar methods would be utilized in creating the vectors/ viral particles of this invention, for expression of the antibody or antibody fragment. The genes encoding monoclonal antibodies that target, for example, tumor associated antigens (TAAs) expressed on a cell surface (e.g., prostate specific antigen (PSA)), can be isolated and used to produce the desired viral particles of this invention, or subcloned into an appropriate expression vector and expressed on a cell surface, through methodology well known to an individual skilled in the art.

Examples of antibodies include those antibodies, which react with malignant prostatic epithelium but not with benign prostate tissue (e.g., ATCC No. HB-9119; ATCC HB-9120; and ATCC No. HB-11430) or react with malignant breast cancer cells but not with normal breast tissue (e.g., ATCC No. HB-8691; ATCC No. HB-10807; and 21HB-108011). Other antibodies or fragments thereof, which react with diseased tissue and not with normal tissue, would be apparent to the skilled artisan.

In one embodiment, the viral particles and cells described herein are targeted to tumor cells, expressing, for example, the surface marker erbB. Such erbB+cells, in turn, would be referred to herein as "target cells" as these cells are the population, which are targeted by the viral particles/cells of this invention. Target cells often express a surface marker or "target antigen" that may be utilized for directing the viral particles/cells to the cell, as opposed to neighboring cells, that are not tumor cells in origin and hence do not express erbB The target antigen may be a receptor, therefore an "antireceptor," also referred to as "attachment protein," signifies a protein displayed on surface of the viral particle, responsible for attachment of the viral particle/modified cell to its corresponding "receptor" on the target cell membrane. For example, the native antireceptor of the pararmyxovirus SV5 is the viral HN protein, which binds sialic acid on host cell membranes. Fusion thus accomplished is mediated via the binding of an attachment protein (or "antireceptor") on the viral envelope to a cognate receptor on the cell membrane.

In one embodiment, "attachment" refers to the act of antireceptor (expressed on viral particle lipid envelopes or engineered cell sufaces) recognition and binding to a target cell surface "receptor" during infection.

In another embodiment, the viral particles/cells of the present invention express anti-receptors which function to direct them to virally infected cells, via anti-receptor binding to viral proteins expressed on infected cell surfaces. In this case, antireceptors to promote viral particle/cell fusion with virally-infected cells, will recognize and bind to virally expressed surface proteins. For example, HIV-1 infected cells may express HIV-associated proteins, such as gp120, and therefore expression of CD4 by the viral particle/cell promotes targeting to HIV infected cells, via CD4-gp120 interaction.

Immune Responses to Heterologous Sequences Via Targeted Lentiviral NLS Expression:

In one embodiment, targeting of the vectors, viral particles, and/or cells of this invention serves to promote an immune response to a product expressed in a target cell, as a result of target cell contact with the vectors, viral particles, and/or cells of this invention.

Examples of infectious virus to which stimulation of a protective immune response is desirable via the methods of this invention include: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g. influenza viruses); Bungaviridae (e.g., Hantaan viruses, bunga viruses, phleboviruses and Nairo viruses); Arena viridae (hemorrhagic fever viruses); Reoviridae (erg., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviiidae (herpes simplex virus (HSV) 1 and 2, varicella zoster virus, cytomegalovirus (CMV), herpes viruses'); Poxviridae (variola viruses, vaccinia viruses, pox viruses); and Iridoviridae (e.g. African swine fever virus); and unclassified viruses (e.g., the etiological agents of Spongiform encephalopathies, the agent of delta hepatities (thought to be a defective satellite of hepatitis B virus), the agents of non-A, non-B hepatitis (class 1=intemally transmitted; class 2=parenterally transmitted (i.e., Hepatitis C); Norwalk and related viruses, and astroviruses)

Examples of infectious bacteria to which stimulation of a protective immune response is desirable include: *Helicobacter pyloi, Borellia burgdorferi, Legionella pneumophilia, Mycobacteria* sps (e.g. *M. tuberculosis, M. avium, M. intracellulare, M. kansaii, M. gordonae*), *Staphylococcus aureus, Neissera gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcius faecalis, Streptococcus bovis, Streptococcus* (*anaerobic* sps.), *Streptococcus pneumoniae, pathogenic Campylobacter* sp., *Enterococcus* sp., *Chlamidia* sp., *Haemophilus influenzae, Bacillus antracis, corynebacterium diphtheriae, corynebacterium* sp, *Erysipelothrix rhusiopathiae, Clostrididium perfringers, Clostridium tetani, Enterobacter aerogenes, Klebsiella pneumoniae, Pastur-ella multcoida, Bacteroides* sp., *Fusobacteriwn nucleatum, Streptobacillus moniliformis, Treponema pallidium, Treponema pertenue, Leptospira, Actinomyces israelli* and *Francisella tularensis.*

Examples of infectious fungi to which stimulation of a protective immune response is desirable include: *Cryptococcus neoformans, Histoplasma capsulatum, Coccidioides immitis, Blastomyces dermatitidis, Chlamydia trachoniatis, Candida albicans*. Other infectious organisms (i.e., protists) include: *Plasmodium* sp., *Leishniania* sp., *Schistosoma* sp. and *Toxoplasma* sp.

Proteins of parasitic agents, which reside intracellularly, also are targets contemplated for infection by the vectors, viral particles, liposomes and cells of this invention. The intracellular parasites contemplated include for example, Protozoa. Protozoa, which infect cells, include: parasites of the genus *Plasmodium* (e.g., *Plasmodium falciparum, P. Vivax P. ovale* and *P. malariae*), *Trypanosoma, Toxoplasma, Leishmania,* and *Cryptosporidium.*

In one embodiment, utilizing targeting moieties to cells infected with any of the above pathogens is considered as part of this invention. In another embodiment, the targeting moiety may be cleaved following cellular entry. Targeting may be accomplished via any of the methods well known to one skilled in the art, utilizing the vectors, viral particles, compositions, liposomes and cells of this invention In another embodiment, the heterologous protein expressed may comprise other immunomodulating proteins such as, for example, cytokines, chemokines, complement components, immune system accessory and adhesion molecules and their receptors of human or non-human animal specificity. In some embodiments the immunomodulatory proteins comprise GM-CSF, IL-2, IL-12, OX40, OX40L (gp34), lymphotactin, CD40, and CD40L. Further immunomolulatory proteins comprise interleukins, for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components and their receptors, or an accessory molecule such as B7.1, B7.2, TRAP, ICAM-1, 2 or 3 and cytokine receptors. OX40 and OX40-ligand (gp34) are further useful examples of immunomodulatory proteins. Immunomodulatory proteins may also comprise class II molecules of the MHC, which may be upregulated on infected cells such as professional antigen presenting cells. Multiple immunomodulatory proteins and/or immunogenic proteins may be incorporated within a single construct, and as such, represents an additional embodiment of the invention.

Diseased and/or abnormal cells may be targeted using the vectors, viral particles, liposomes, compositions and cells of the invention by the methods described above. The diseased or abnormal cells contemplated may comprise infected cells, neoplastic cells, pre-neoplastic cells, inflammatory foci, benign tumors or polyps, cafe au lait spots, leulcoplakia, skin moles, or cells deficient for expression of a particular gene product.

The vectors, viral particles, liposomes, compositions or cells of the invention may be targeted using an anti-receptor that will recognize and bind to its cognate receptor or ligand expressed on the diseased or abnormal cell.

In one embodiment, the viral particles, cells and compositions of the present invention comprise a targeting moiety as described, and a cytotoxic agent such that upon contacting a target cell, target cell cytotoxicity occurs.

In another embodiment, diseased and/or abnormal cells may be uniquely susceptible to infection with the vectors, viral particles, liposomes, compositions or cells of this invention. In another embodiment, the vectors, viral particles, liposomes, compositions or cells of this invention expressing an immunogenic protein or peptide fragment may generate immune responses of a variety of types that can be thus stimulated, including responses against the heterologously expressed protein or peptide, other antigens that are now immunogenic via a "by-stander" effect, against host antigens, and others, and represent additional embodiments of the invention. It is envisioned that methods of the present invention can be used to prevent or treat bacterial, viral, parasitic or other disease states, including tumors, in a subject.

Combination vaccines have been shown to provide enhanced immunogenicity and protection, and, as such, in another embodiment, the immunogenic proteins or peptides are derived from different species.

Induced Cytotoxicity Via the Use of the Lentiviral NLS:

In another embodiment, the vectors, viral particles, liposomes or cells of this invention further comprise/express a toxic protein, producing cell death. In one embodiment, the toxic protein is cytotoxic. In another embodiment, the toxic protein is a nuclease, whose expression results in DNA damage, promoting cell death. In another embodiment, the vectors, viral particles, liposomes or cells of this invention further comprise/express a suicide gene, resulting in cell death, in cells that comprise the products herein In one embodiment, the term "suicide gene" refers to a nucleic acid coding for a product, wherein the product causes cell death by itself or in the presence of other compounds. A representative example of a suicide gene is one, which codes for thymidine kinase of herpes simplex virus. Additional examples are thymidine kinase of varicella zoster virus and the bacterial gene cytosine deaminase, which can convert 5-fluorocytosine to the highly cytotoxic compound 5-fluorouracil.

Suicide genes may produce cytotoxicity by converting a prodrug to a product that is cytotoxic. As used herein "prodrug" means any compound that can be converted to a toxic product for cells. Representative examples of such a prodrug is gancyclovir which is converted in vivo to a toxic compound by HSV-thymidine kinase. The gancyclovir derivative subsequently is toxic to cells. Other representative examples of prodrugs include acyclovir, FIAU [1-(2-deoxy-2-fluoro-β-D-arabinofuranosyl)-5-iodouracil], 6-methoxypurine arabinoside for VZV-TK, and 5-fluorocytosine for cytosine dearninase.

In one embodiment, the incorporation of suicide genes within cells results in targeted cytotoxicity, which provides a therapeutic protocol when targeted cell lysis is desired. Such incorporation will, in another embodiment, be desirable for anti-cancer applications, whereby cancer cells are specifically targeted via the vectors, viral particles, liposomes, cells and/or compositions of the invention, and cancer cell specific lysis may be affected by incorporation of a suicide gene.

In another embodiment, this invention provides a method of targeted cell death, comprising contacting a cell with a viral particle comprising a nucleic acid encoding a lentiviral nuclear localization signal, fused in frame to a nucleic acid encoding for a cytotoxic protein and a targeting moiety expressed on said viral particle surface wherein said targeting moiety directs said viral particle to a cell of interest, whereby said nucleic acid is expressed in the cytoplasm of said cell of interest, and following nuclear import of said lentiviral nuclear localization signal to said cytotoxic protein cell death is stimulated, thereby accomplishing targeted cell death. In one embodiment, targeted cell death is inducible, by methods well known to one skilled in the art.

In another embodiment, the heterologous protein encoded by the isolated nucleic acids, and comprising the vectors, viral particles, liposomes, cells and/or compositions of this invention may stimulate or enhance apoptosis. Such proteins may be pro-apoptotic, such as, for example, REAPER, GRIM, HID, Sickle, Smac/Diablo, Omi/HtrA2, caspases, and other molecules well known to one skilled in the art.

In one embodiment, cellular cytotoxic effects may be determined via viability assays. In another embodiment, effects on cell proliferation are determined. In another embodiment, effects on cell surface marker expression or cell cycle stage are determined. Such effects are readily measured by methods well known to one skilled in the art, and comprise, but are not limited to:measurements of dye uptake as a measurement of viability, such as, for example, trypan blue exclusion, measurements of cell proliferation can be determined by, for example measurements of 3H -Thymidine uptake, and cell surface marker expression and cell cycle stage can be determined by FACS, and other methods, according to protocols well known to one skilled in the art. Each of these methods may be utilized to determine the effects on diseased cells, as well as cell cytotoxicity, and are to be considered additional embodiments of this invention In another embodiment, the vector/viral particle contemplated by this invention further comprises an insertion of a heterologous nucleic acid sequence encoding a marker polypeptide. The marker polypeptide may comprise, for example, green fluorescent protein (GFP), DS-Red (red fluorescent protein), secreted alkaline phosphatase (SEAP), β-galactosidase, luciferase, or any number of other reporter proteins known to one skilled in the art.

Recombinant Proteins Comprising a Lentiviral NLS:

In another embodiment, this invention provides a recombinant protein comprising a lentiviral nuclear localization signal, comprising an amino acid sequence corresponding to the formula: $R_5(R_6)_2$ $FrVYR_1R_3R_2R_8R_3nplWR_3GPR_8kR_4R_5WR_3GEGA(R_4)_3$ $R_6dR_6sR_6R_4kvR_4PR(R_3)_2R_8KIR_4R_3d$ wherein R1=an aromatic amino acid, R2=an acidic amino acid, R3=a basic amino acid, R4=a branched chain amino acid, R5=a hydrophobic amino acid, R6=a polar amino acid, R7=a proline or serine amino acid residue and R8=a small amino acid residue, lower case letters=the preferred amino acid residue, however substutions with amino acid residues from disparate groups are possible as well.

In another embodiment, this invention provides a recombinant protein comprising a lentiviral nuclear localization signal, comprising an amino acid sequence corresponding to: IQNFRVYYRDSRNPLWKGPAKLLWKGE-GAVVIQDNSDIKVVPRRKAKIIRD (SEQ ID NO:147).

In another embodiment, the recombinant protein comprises a lentiviral nuclear localization signal with an amino acid sequence homologous to SEQ ID NO: 139, 147 or 149. In another embodiment, the recombinant protein comprises a lentiviral nuclear localization signal encoded by a nucleic acid sequence homologous to SEQ ID NO: 130, 138 or 148.

In another embodiment, the recombinant protein comprises a lentiviral nuclear localization signal, wherein the NLS is located at an N- or C-terminus of the recombinant protein. The efficient expression of an N- or C-terminal NLS conferring the ability to transport to the nucleus was demonstrated herein, in Example 2.

In another embodiment, the recombinant protein may further comprise a heterologous protein, as described above, for expression of lentiviral NLS. It is to be understood that each embodiment for a nucleic acid encoding, or vectors, viral particles, compositions, liposomes and/or cells comprising an NLS are also envisioned for recombinant proteins comprising an NLS, such as, for example, the generation of a recombinanat protein comprising a lentiviral NLS, fused to, or further comprising a therapeutic protein, as described herein, an immunogenic protein, a targeting moiety, an agent that regulates gene expression and/or a cytotoxic agent. Combinations of some or all of these are also envisioned for the isolated nucleic acids, vectors, liposomes, viral particles, recombinant proteins, cells and/or compositions comprising the same.

It is to be understood that compositions, cells and/or viral particles comprising the recombinant proteins of this invention represent additional embodiments, and are considered as part of this invention.

Cytotoxicity MediatedVia the Lentiviral NLS

In another embodiment, this invention provides a method of stimulating or enhancing cell death, comprising contacting a cell with a complex comprising a lentiviral nuclear localization signal covalently attached to a cytotoxic agent, wherein following nuclear import of said complex said cytotoxic agent stimulates cell death, thereby stimulating or enhancing cell death.

In one embodiment, the terms "agent" or "candidate agent" are to be considered synonymous herein, and represent chemical or biological molecules such as a simple or complex organic molecules, peptides, peptidomimetics, mimetics, proteins, oligonucleotides, nucleic acid, drugs or other compounds that are utilized for the indicated purpose herein.

The cytotoxic agent may, in one embodiment, be attached to the lentiviral NLS via the use of a linker molecule. A "linker molecule", in one embodiment, is a molecule that is used to join two molecules. The linker molecule may, in another embodiment, form covalent bonds to both molecules. Linker molecules are well known to those of skill in the art and may include, in one embodiment, straight or branched-chain carbon linkers, or, in another embodiment, heterocyclic carbon linkers, or in another embodiment, peptide linkers. In another embodiment, when the cytotoxic agent comprises amino acids, the linkers may be joined to both constituent amino acids through their side groups (e.g., through a disulfide linkage to cysteine). In another embodiment, the linkers may be joined to the alpha carbon amino and carboxyl groups of terminal amino acids.

In one embodiment, the cytotoxic agent is an alkylating agent. Alkylating agents are, in another embodiment, polyfunctional compounds that have the ability to substitute alkyl groups for hydrogen ions. These compounds react with and irreversibly alkylate phosphate, amino, hydroxyl, sulfhydryl, carboxyl, and imidazole groups. Examples of alkylating agents include bischloroethylamines (nitrogen mustards), aziridines, alkyl alkone sulfonates, nitrosoureas, and platinum compounds. Under physiological conditions, these drugs ionize and produce positively charged ions that attach to susceptible nucleic acids and proteins, leading to cell cycle arrest and/or cell death. The alkylating agents are cell cycle phase nonspecific agents because they exert their activity independently of the specific phase of the cell cycle. The nitrogen mustards and alkyl alkone sulfonates are effective, in one embodiment, against cells in the G1 or M phase. Nitrosoureas, nitrogen mustards, and aziridines, in another embodiment, impair progression from the G1 and S phases to the M phase.

In another embodiment, the cytotoxic agent is an antimetabolic agent. In one embodiment, the antimetabolic agent is fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and/or gemcitabine.

In another embodiment the cytotoxic agent is a nuclease. In another embodiment, the cytotoxic agent is pro-apoptotic.

In another embodiment, a combination of the cytotoxic agents listed herein may be employed.

Cell death may be determined via any number of means well known in the art, including via dye exclusion assays and/or via histopathology, as determined by light or fluorescent microscopy or FACS analysis. Cellular cytotoxicity may also be a function of the stimulation of apoptosis. Apoptosis is an active process requiring metabolic activity by the dying cell; often characterized by shrinkage of the cell, cleavage of the DNA into fragments that give a so-called "laddering pattern" on gels and by condensation and margination of chromatin. Methodology for measuring apoptosis includes, but is not limited to: measurement of DNA fragmentation by pulsed field gel electrophoresis (Belyaev IY and Harms-Ringdahl M., (2002) Radiats Biol Radioecol 42: 279-83) or by terminal deoxynucleotidyl transferase-mediated deoxyuridinetriphosphate nick end-labeling (TUNEL) (Edston E. et al, (2002) Int J Legal Med 116: 22-6), measurement of membrane dielectric changes (Wang X, et al. (2002) Biochim Biophys Acta 1564: 412-20), microscopic examination and confirmation of the presence of characteristic pyknotic nucleii, and others.

Mutated Lentiviral NLS:

In one embodiment, this invention provides a mutated lentiviral nuclear localization signal.

Example 1 demonstrated that multiple alanine substitutions within the carboxy-terminus of integrase, spanning residues 236-40 and 262-266, or removal of the C-terminal 28 amino acids as well as more extensive deletions, resulted in nuclear exclusion.

According to this aspect of the invention, in one embodiment, the mutated lentiviral nuclear localization signal comprises an amino acid sequence homologous to SEQ ID NO: 67-129, 139, 140, 141, 142, 143, 144, 145, 146 or 147. In another embodiment, the mutated lentiviral nuclear localization signal is encoded by a nucleic acid sequence homologous to SEQ ID NO: 4-65, 130, 131, 132, 133, 134, 132, 136, 137, 138 or 146.

In another embodiment, this invention provides an isolated polynucleotide encoding for a mutated lentiviral nuclear localization signal. In one embodiment, the isolated polynucleotide encodes for a lentiviral nuclear localization signal, comprising encoding for a mutated lentiviral nuclear localization signal, comprising an amino acid sequence homologous to SEQ ID NO: 67-129, 139, 140, 141, 142, 143, 144, 145, 146 or 147. In another embodiment, the isolated polynucleotide comprises a nucleic acid sequence homologous to SEQ ID NO: 4-65, 130, 131, 132, 133, 134, 132, 136, 137, 138 or 146.

In another embodiment, this invention provides a recombinant protein comprising a mutated lentiviral nuclear localization signal. In one embodiment, the recombinant protein comprises a mutated lentiviral nuclear localization signal with an amino acid sequence corresponding to or homologous to SEQ ID NO: 67-129, 139, 140, 141, 142, 143, 144, 145, 146 or 147. In another embodiment, the recombinant protein comprises a mutated lentiviral nuclear localization signal encoded by a nucleic acid sequence corresponding to or homologous to SEQ ID NO: 4-65, 130, 131, 132, 133, 134, 132, 136, 137, 138 or 146. In another embodiment, the invention provides a cell, viral particle and/or composition comprising the mutated lentiviral nuclear localization signal.

In another embodiment, this invention provides for a vector, viral particle, liposome, cell and/or composition comprising a nucleic acid encoding for a mutated lentiviral nuclear localization signal, as described herein.

It is to be understood that each and every embodiment described herein for recombinant proteins, isolated nucleic acids, vectors, viral particles, liposomes, cells and/or compositions of this invention are applicable as well to those relating to mutated lentiviral nuclear localization signals, and are to be considered as part of this invention.

Inhibition of HIV Integration

Infections of monocyte-derived-macrophages with the integrase NLS mutant viruses were non-productive (FIG. 3C). Mutant viruses were also replication-defective in the cycling CEM-SS T-lymphoblastoma cell line and activated cultures of CD8-depleted peripheral blood lymphocytes. NLS-mutant viruses were also unable to induce Tat-mediated indicator gene expression in either dividing P4-CCR5 cells or those arrested with aphidicolin in the G1 phase of the cell cycle (FIG. 3D). Thus, these results demonstrated that the lentiviral integrase NLS-mutant viruses were compromised at an early stage of the HIV life cycle, prior to nuclear entry and tat gene-induced viral transcription.

Lentiviruses are able to maintain themselves in a non-integrated, extra-chromosomal form in resting T-cells, a phenomenon which may be related to the presence of latently infected peripheral blood lymphocytes in HIV-1 infected subjects, wherein the virus is present in a provirus form. The inhibition of proviral integration would impact HIV pathogenesis.

In one embodiment, this invention provides a method of inhibiting or abrogating HIV proviral integration, comprising contacting an HIV infected cell with a vector or viral particle comprising at least one copy of a nucleic acid encoding an integrase wherein said integrase comprises a mutated lentiviral nuclear localization signal, whereby said mutated integrase competes for the HIV integrase present in said infected cell, preventing proviral nuclear entry, thereby inhibiting or abrogating proviral integration.

In one embodiment, 2 copies of the mutated integrase are contacted with the HIV infected cell, or in another embodiment, 3 copies of the mutated integrase, or in another embodiment, 4 copies of the mutated integrase, or in another embodiment, 5 copies of the mutated integrase, or in another embodiment, 6 copies of the mutated integrase, or in another embodiment, 7 copies of the mutated integrase, are contacted with the HIV infected cell. Methods for designing vectors for multi-copy expression of a nucleic acid sequence are well known in the art, and are to be considered as part of this invention.

The method according to this aspect of the invention may be exercised, in one embodiment, at the onset of infection, or in another embodiment, following exposure to HIV infection, prior to evidence of HIV infection, or in another embodiment, at any stage of HIV disease.

In one embodiment, the mutated HIV integrase NLS is supplied as a recombinant protein, or in another embodiment, as a recombinant viral particle. In another embodiment, a vector comprising a nucleic acid sequence encoding for a mutated HIV integrase NLS is contacted with an HIV infected cell. In another embodiment, an isolated nucleic acid encoding for a mutated HIV integrase NLS is contacted with an HIV infected cell. In another embodiment, a cell comprising a mutated HIV integrase NLS is contacted with an HIV infected cell. In one embodiment, fusion of the cell comprising a mutated HIV integrase NLS with the HIV infected cell facilitates delivery of the mutated HIV integrase to the infected cell, with the mutated HIV integrase delivered to the cytoplasm of the HIV infected cell, competing with HIV integrase. In another embodiment, a liposome comprising a mutated HIV integrase NLS is contacted with an HIV infected cell, whereby, in one embodiment, following fusion with the infected cell, the mutated HIV integrase is delivered to the cytoplasm of the infected cell, and completes with native HIV integrase, thereby inhibiting or abrogating proviral integration. In another embodiment, a composition comprising the liposome, cells, recombinant protein, vector, viral particle or isolated nucleic acid comprising a mutated HIV integrase NLS is utilized in the methods described herein.

Inhibition of HIV proviral integration may be measured by any number of means well known in the art, including, in one embodiment, via southern blot analysis, or, in another embodiment via 2-LTR circle formation analysis, as exemplified herein, or, in another embodiment, via immunohistochemistry, or, in another embodiment, via in situ hybridization, and others.

As described herein, HIV proviral integration, in one embodiment, is involved in HIV pathogenesis, and in disease progression. In another embodiment, this invention provides a method of inhibiting or abrogating HIV pathogenesis or disease progression, comprising contacting an HIV infected cell with a vector or viral particle comprising at least one copy of a nucleic acid encoding an integrase wherein said integrase comprises a mutated lentiviral nuclear localization signal, whereby said mutated integrase competes for the HIV integrase present in said infected cell, preventing proviral nuclear entry, thereby inhibiting or abrogating HIV pathogenesis or disease progression.

Both the HIV Matrix and Integrase proteins have been shown to interact with the human embryonic ectoderm development (EED) protein, colocalizing in the nucleus and at nuclear pores, early post-infection. The present invention demonstrates conserved PXXP motifs present in human EED, where proline-enriched domains have been shown to exhibit SH3-binding ability. Thus, in addition to inhibition of the HIV integrase NLS, in another embodiment, abrogation or inhibition of EED binding to the HIV integrase NLS is another method where HIV pathogenesis, disease progression or latency may thereby be inhibited. In one embodiment, this inhibition is effected via selective mutation of the PXXP motif in a host cell EED. In another embodiment, the inhibition is effected via antibodies directed to the PXXP domain of the EED, thereby creating steric hindrance, obviating an interaction with the HIV integrase NLS. In another embodiment, competitive inhibition with a mutated EED protein, comprising a PXXP domain, such as, in one embodiment, a truncated protein, or, in another embodiment, C-terminal substitutions, may be utilized. According to this aspect of the invention, the mutated EED protein does not facilitate binding to the HIV integrase NLS and/or, does not facilitate nuclear import of the PIC complex.

Inhibition of HIV Pathogenesis and Disease Progression

HIV proviral integration is also involved, in another embodiment, in the establishment and/or maintenance of HIV latency. In another embodiment, this invention provides a method of inhibiting or abrogating HIV latency, comprising contacting an HIV infected cell with a vector or viral particle comprising at least one copy of a nucleic acid encoding an integrase wherein said integrase comprises a mutated lentiviral nuclear localization signal, whereby said mutated integrase competes for the HIV integrase present in said infected cell, preventing HIV integrase or derivatives thereof or of the HIV provirus from nuclear entry, thereby inhibiting or abrogating HIV latency.

In one embodiment, HIV integrase NLS targeting of the enzyme to the host cell nucleus, where proviral integration into the host genome occurs, plays a role in HIV pathogenesis and disease progression, as described. Specific inhibitors of the HIV NLS thereby prevent nuclear import, hence proviral integration, and ultimately HIV pathogenesis and disease progression In another embodiment, this invention provides a method of inhibiting or abrogating HIV pathogenesis or disease progression, comprising contacting an HIV infected cell with an inhibitor of a lentiviral nuclear localization signal, whereby said inhibitor prevents nuclear entry of HIV provirus, thereby inhibiting or abrogating HIV pathogenesis or disease progression.

In one embodiment, a lentiviral NLS inhibitor inhibits NLS expression, activity or function. In one embodiment, the inhibitor comprises a nucleic acid. The nucleic acid may, in one embodiment, be DNA, or in another embodiment, the nucleic acid is RNA. In other embodiments, the nucleic acid may be single or double stranded In another embodiment, the inhibitor is a nucleic acid that is antisense in orientation to a sequence encoding for a lentiviral NLS.

According to this aspect of the invention, in one embodiment, inhibition of NLS expression, activity or function is effected via the use of antisense oligonucleotides, which are chimeric molecules, containing two or more chemically distinct regions, each made up of at least one nucleotide. These chimeric oligonucleotides contain, in one embodiment, at least one region wherein the oligonucleotide is modified so as to confer upon the oligonucleotide, in one embodiment, an increased resistance to nuclease degradation, or, in another embodiment, increased cellular uptake, and/or, in another embodiment, an increased binding affinity for the target polynucleotide. An additional region of the oligonucleotide may serve as a substrate for enzymes capable of cleaving RNA: DNA or RNA:RNA hybrids, which according to this aspect of the invention, serves as a means of gene silencing via degradation of specific sequences. Cleavage of the RNA target can be detected, in one embodiment by gel electrophoresis or, in another embodiment via nucleic acid hybridization techniques known in the art.

The chimeric antisense oligonucleotides may, in one embodiment, be formed as composite structures of two or more oligonucleotides and/or modified oligonucleotides, as is well described in the art (see, for example, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922), and can, in another embodiment, comprise a ribozyme sequence.

Inhibition of lentiviral NLS expression, activity or function is effected, in another embodiment, via the use of small interfering RNAs, which provides sequence-specific inhibition of gene expression. Administration of double stranded/duplex RNA (dsRNA) corresponding to a single gene in an organism can silence expression of the specific gene by rapid degradation of the mRNA in affected cells. This process is referred to as gene silencing, with the dsRNA functioning as a specific RNA inhibitor (RNAi). RNAi may be derived from natural sources, such as in endogenous virus and transposon activity, or it can be artificially introduced into cells (Elbashir S M, et al (2001). Nature 411:494-498) via microinjection (Fire et al. (1998) Nature 391: 806-11), or by transformation with gene constructs generating complementary RNAs or fold-back RNA, or by other vectors (Waterhouse, P. M., et al. (1998). Proc. Natl. Acad. Sci. USA 95, 13959-13964 and Wang, Z., et al. (2000). J. Biol. Chem. 275, 40174-40179). The RNAi mediating MRNA degradation, in one embodiment, comprises duplex or double-stranded RNA, or, in other embodiments, include single-stranded RNA, isolated RNA (partially purified RNA, essentially pure RNA, synthetic RNA, recombinantly produced RNA), as well as altered RNA that differs from naturally occurring RNA by the addition, deletion and/or alteration of one or more nucleotides.

In another embodiment, the lentiviral NLS inhibitor comprises a chemical inhibitor or a polypeptide preventing protein function. The inhibitor may comprise an antibody or antibody fragment, the design of which is via methodology well known to those skilled in the art.

In another embodiment, the inhibitor is designed to physically block lentiviral NLS interaction with nuclear import machinery of the cell. The design of a molecule that physically blocks lentiviral NLS interaction with nuclear import machinery can be accomplished by methods well known in the art. The structure of the lentiviral NLS has been ascertained by computer algorithm to assume an SH3-like structure. The lentiviral NLS structure may further by established, by for example, X-Ray crystallographic data or NMR, whereupon binding sites can be ascertained, which can be filled with a close packed array of generic atoms. A Monte Carlo procedure (D. K. Gehlhaar, et al. "De Novo Design of Enzyme Inhibitors by Monte Carlo Ligand Generation" J. Med. Chem. 1995, 38, 466472) may be used, in another embodiment, to randomly move, rotate, exchange atom types and/or bond types, and the resulting chemical moieties, representing inhibitors for lentiviral NLS, designed can be tested for their ability to inhibit the lentiviral NLS interaction with nuclear import machinery, or lentiviral nuclear import, or other methods as describe herein.

In another embodiment, methods that can be modified to design inhibitors of the lentiviral NLS interaction with nuclear import machinery include: MCSS (Multiple Copy Simultaneous Search)/HOOK (A. Caflish, et al. J. Med.

Chem. 1993, 36, 2142-2167; M. B. Eisen, et al., Str. Funct. Genetics 1994, 19, 199-221), LUDI (H.-J. Bohm J. Comp-Aided Mol. Design 1992, 6, 61-78) GROW (J. B. Moon and W. J. Howe Str. Funct. Genetics 1991, 11, 314-328) CoMFA (Conformational Molecular Field Analysis) (J. J. Kaminski Adv. Drug Delivery Reviews 1994 14 331-337) and other methods known to one skilled in the art.

It is to be understood that any inhibitor designed to regulate lentiviral nuclear import, or proviral integration, or other methods described herein, via minimizing or preventing lentiviral NLS interaction with nuclear import machinery, is to be considered part of the present invention.

In another embodiment, this invention provides a method of inhibiting or abrogating HIV latency, comprising contacting an HIV infected cell with an inhibitor of a lentiviral nuclear localization signal, whereby said inhibitor prevents nuclear entry of HIV integrase or derivatives thereof or of the HIV provirus, thereby inhibiting or abrogating HIV latency, In another embodiment, this invention provides a method of inhibiting or abrogating HIV pathogenesis or disease progression, comprising contacting an HIV infected cell with an nucleic acid sequence complementary to a lentiviral nuclear localization signal, or a fragment thereof, whereby said nucleic acid sequence inhibits expression or promotes degradation of an HIV integrase nuclear localization signal, preventing nuclear entry of HIV provirus, thereby inhibiting or abrogating HIV pathogenesis or disease progression.

In another embodiment, this invention provides a method of inhibiting or abrogating HIV latency, comprising contacting an HIV infected cell with a nucleic acid sequence complementary to a lentiviral nuclear localization signal, or a fragment thereof, whereby said nucleic acid sequence inhibits expression or promotes degradation of an HIV integrase nuclear localization signal, preventing nuclear entry of HIV integrase or derivatives thereof or of the HIV provirus, thereby inhibiting or abrogating HIV latency.

Screening Methods for Identification of Lentiviral NLS Inhibitors

In another embodiment, this invention provides a method of screening for an agent that inhibits HIV nuclear import comprising contacting an HIV integrase protein with a candidate agent and determining HIV PIC nuclear import, wherein lack of HIV PIC nuclear import indicates that said candidate agent inhibits HIV nuclear import.

In one embodiment, the agent that inhibits nuclear import is a nucleic acid, as described hereinabove. In another embodiment, the agent is a chemical inhibitor or a polypeptide preventing protein function, such as, for example, an antibody or antibody fragment.

According to this aspect of the invention, the agent may exhibit, in one embodiment, homology to the lentiviral NLS, or the mutants described herein, or nucleic, or nucleotides encoding same, as disclosed hereinabove. Compounds for screening mimicking lentiviral NLS molecules, as herein described may be generated synthetically, via translation of sequences subjected to any mutagenesis technique, as well as via protein evolution techniques, well known to those skilled in the art.

In one embodiment, the screening method may determine lack of HIV PIC import via light, immunostaining, and/or fluorescent microscopy. In another embodiment, lack of HIV PIC import may be determined via hybridization technology measuring lentiviral proviral integration.

In another embodiment, the screening methods may be effected via determining 2-LTR circle formation, as described and exemplified herein. In another embodiment, the screening methods may be effected via determining lentivirus proviral integration. It is to be understood that any screening method that demonstrates an alteration in lentiviral nuclear import via the use of an agent that inhibits a lentiviral NLS for identification of an inhibitor of lentiviral nuclear import is to be considered as part of this invention, and an embodiment thereof.

The following examples are intended to illustrate but not limit the present invention.

EXAMPLES

Materials and Experimental Methods

Construction of Plasmids

Expression vectors containing the coding sequence for enhanced green fluorescent protein (EGFP) (Clontech), upstream of an HIV-1 integrase (IN) open reading frame derived from the CXCR4-tropic, HXB-2 subclone, R7/3 HIV strains were used (EGFP-IN) (Miller, M. D., et al. (1994) J Exp Med 179:101-13). The gene fusion was cloned into pcDNA3.1(+)-CTE, a derivative of pcDNA3.1(+) (Invitrogen), that includes the constitutive transport element (CTE) from Mason-Pfizer monkey virus.

A synthetic, codon-modified IN gene, IN-MOD, with a nucleic acid sequence: atgttcctgg acggtatcga caaagetcag gac-gagcacg aaaagtacca ttctaactggcgcgccatgg cctctgactt caatctc-ccg ccggttgttg ccaaggagat cgtggcttcttgcgacaagt gccaattgaa gggtgaggct atgcatggtc aggtcgattg ctctcccggtatctggcagc tggactgcac tcacctcgag ggtaaggtga ttctcgttgc tgtgcacgtggcttc-cggct acatcgaggc tgaggtcatc ccggctgaga ccggtcaaga gactgct-tacttcctgctca agctggccgg ccgttggcca gttaagacta ttcacactga taacggttct aactttactt ccgcaactgt gaaagctgca tgctggtggg ccg-gcattaa acaagagttc ggaattccgt ataacccgca gtctcagggc gttgtc-gagt ctatgaacaa ggagctcaaa aagatcattg gtcaagtccg tgaccaagct gagcacctta agaccgctgt gcagatggct gtttttattc ataacttcaa gcg-taagggt ggtatcggtg gttatagcgc tggtgagcgt atcgtagaca tcatcgc-tac tgatatccag acaaaggagc tgcagaagca gatcactaag atccagaact tccgtgtgta ctatcgggac tctaggaacc cgctctggaa gggtcctgct aaact-gctgt ggaagggaga gggtgctgtt gttatccagg acaactctga tatcaaggtg gttccgcgtc gtaaggctaa aattatccgc gactacggca agcaaatggc tggagacgac tgcgttgcta gccgtcaaga cgaagactaa (SEQ ID NO: 1) (GenBank Accession #AF422697), was constructed by primer extension of overlapping 100 base-pair oligonucleotide segments and cloned into pcDNA31(+)-CTE to create the modified integrase expression plasmid, pcDNA3.1(+) IN-MOD-CTE. The natural version of the viral integrase gene from R7/3, IN-VIR, was cloned into pcDNA3.1(+)-CTE to create the cognate, viral integrase expression vector, pcDNA3.1 (+) IN-VIR-CTE. These plasmids are identical except for the segment encoding the wild-type integrase amino acid sequence. For viral studies, relevant mutations were subcloned into derivatives of R7/3. In some cases, the envelope gene of R7/3 was replaced with that of the macrophage-tropic primary isolate, R7/3(YU-2) (Li, Y., et al. (1991) J Virol 65:3973-85; Wiskerchen, M., and M. A. Muesing (1995) J. Virol. 69:376-386), or with an interrupted envelope gene containing a gpt expression cassette, R7/3 gpt (M. A. Muesing (1995) J. Virol. 69:376-386).

Cell Culture, Transfections, and Viral Production

HEK293, Hek293T, P4-CCR5 and CEM-SS cells were maintained in the appropriate media. Macrophages were prepared from the peripheral blood mononuclear cells (PBMC) of normal blood donors by density gradient centrifugation on 46% Percoll (Amersharn Pharmacia Biotech), followed by plastic adherence and culture for 8-15 days in RPMI-1640 with 2% Human AB serum (Sigma) before infection. Activated CD8-depleted peripheral blood leukocytes (PBL) were generated from the same donor-matched PBMC samples used to prepare the macrophages. Lymphocytes and dendritic cells were purified from blood and transfected by nucleofection (AMAXA, Inc.) with plasmid DNA.

All viral stocks were prepared in transfected 293T cells filtered through 0.45 mm filters and treated with DNase I (Sigma) at 8 mg ml-1 for 30 minutes at 37° C.

Infections

P4-CCR5 (HeLa) cells were plated in the presence or absence of aphidicolin (present during the duration of the experiment) and infected with the equivalent of 10 ng of p24 of each virus (X4 or R5) per well, in triplicate, with saquinavir. β-galactosidase activity was quantified using the Galacto-Star kit (Tropix). In situ staining for β-galactosidase activity was performed using the original protocol of Emerman and co-workers (Kimpton, J., and M. Emermman (1992) J Virol 66:2232-9).

Virus was added to a confluent monolayer of macrophages (approximately $2\times10^5$ cells) or activated PBLs ($1\times10^6$) in 24-well format and infection enhanced by spinoculation (O'Doherty, U, et al. (2000) J Virol 74:10074-80). Inhibitors used: 8 mM aphidicolin, 1 mM saquinavir, 10 mM UC781 (Balzarini, J., et al (1996) Antimicrob Agents Chemother 40:1454-66), 5 mM L-731,988 (Hazuda, D. J., et al (2000) Science 287:646-50) Total nucleic acid was obtained using the QiAmp Blood Kit (Qiagen).

Viral stocks were prepared for the trans-complementation assays by co-transfection (1:5 molar ratio) of proviral DNA with either complementing (pVPR-PC-IN D116A) or non-complementing (pcDNA3.1) DNAs and used to infect cells (20 ng p24 CA). Transduction and stable maintenance of the trans-dominant marker, gpt, was used to detect and quantify individual integration events; an assay that has been described previously (Wiskerchen, M., and M. A. Muesing (1995) J. Virol 69:376-386).

Immunocytochemistry and Microscopy

Cells were grown on collagen-treated glass coverslips. After transfection, cells were fixed with 3% electron-microscopy grade formaldehyde in PBS, and, in some cases, stained using mouse monoclonal antibodies to IN (gift of M. Malim), and an AlexaFluor-594-conjugated anti-mouse antibody (Molecular Probes). Coveislips were mounted in medium containing DAPI (Vectashield, Vector Laboratories). EGFP, DAPI and antibody fluorescence were visualized using deconvolution, restoration microscopy (DeltaVision, Applied Precision).

Exogenous and Intravirion Reverse Transciption Assays

An enzymatic assay for reverse transcriptase activity was performed as described previously (Wiskerchen, M., and M. A. Muesing (1995) J. Virol. 69:376-386). To assay endogenous, intravirion reverse transcription, virions were pelleted for 90 minutes at 25,000 rpm over a 20% sucrose cushion and resuspended in PBS. Virus normalized to 100 ng p24 and incubated in 50 mM NaCl, 45 mM Tris (pH 8.0), 10 mM $MgCl_2$, 10 mM DTT, with 100 mM dNTPs, with or without 0.005% Triton X-100, at 37° C. for varying amounts of time. Reactions were diluted with PBS (EDTA), incubated at 65° C. for 30 minutes. Real-time PCR was performed to assay the formation of early and late reverse transcripts.

Northern, Western and Quantitiative PCR

Northern blots were performed by standard methods using as probe a 253 base-pair DNA segment (CTE) in common between the two versions of the integrase expression plasmids. Western blots were performed as described (Wiskerchen, M., and M. A. Muesing (1995) J. Virol. 69:376-386) using mouse monoclonal antibodies against integrase (6G5) (Nilsen, B. M., et al. (1996) J Virol 70:1580-7), GFP (gift of Michael Rout), g-tubulin (Sigma) or an AIDS patient anti-serum.

The sequences for primers and molecular beacons used in real-time were as follows: For the early reverse transcription Real Time PCR assay, primers used were as follows: Forward Printer: 5'-TCTCTGGCTAACTAGGGAACCCACTGCTT-3' (SEQ ID NO:152=bp181-209 in R region of LTR), 491-519 in R73*X4 complete; Reverse Primer: 5'-TGAC-TAAAAGGGTCTGAGGGATCTCTAGTTACCAG-3', (SEQ ID NO:153=bp271-302 in US region of LTR) 581-613 in R73*X4 complete. The molecular beacon used was as follows: 56-FAM-5' CCGAACCAGTAGTGTGTGC-CCGTCTGTTGTGTGGTTCGG-3 '-Dabcyl (SEQ ID NO:154=bp243-266 in U5 region of LTR) 552-576 in R73*X4 complete.

For the late reverse transcription Real Time PCR assay, primers used were as follows: Forward Primer: 5'-AGATC-CCTCAGACCCTTTTAGTCAGTGTGG-3' (SEQ ID NO:155=592-621), Reverse Primer: 5'-GCCGCCCCTCGC-CTCTTG-3', (SEQ ID NO:156=721-738); with the molecular beacon: 5'-CCGACCCTCTCGACGCAGGACTCGGCT-TGGGTCGG-3'. SEQ ID NO:157=684-705.

For 2-LTR Circle assays the forward primer used was: 5'-CTCAGACCCTTTTAGTCAGTGTGGAAAATCTCTA-3' (SEQ ID NO:158), reverse primer: 5'-TGACCCCTGGC-CCTGGTGTGTAG-3' (SEQ ID NO:159), and molecular beacon: 5'-CCGCACCTACCACACACAAGGCTACT-TCGTGCGG-3' (SEQ ID NO:160) 6453-6474 of pTRIP vector 53-74 in R73 X4 LTR.

For CCR5-the forward primer used was: 5'-TCATTACAC-CTGCAGCTCTCATTTTCCATACAGTC-3' (SEQ ID NO:161), reverse primer: 5'-CACCGAAGCAGAGTTTT-TAGGATTCCCGAGTA-3' (SEQ ID NO:162), and molecular beacon: 5'-GCGCCTATGACAAGCAGCGGCAGGAG-GCGC-3' (SEQ ID NO:163).

Molecular beacons were modified on the 5' end with 5-carboxy-fluorescein (FAM) and on the 3' end with Dabcyl (IDT) and reactions performed on an ABI 7700 Prism Sequence Detector Example 1

Figure 1B:
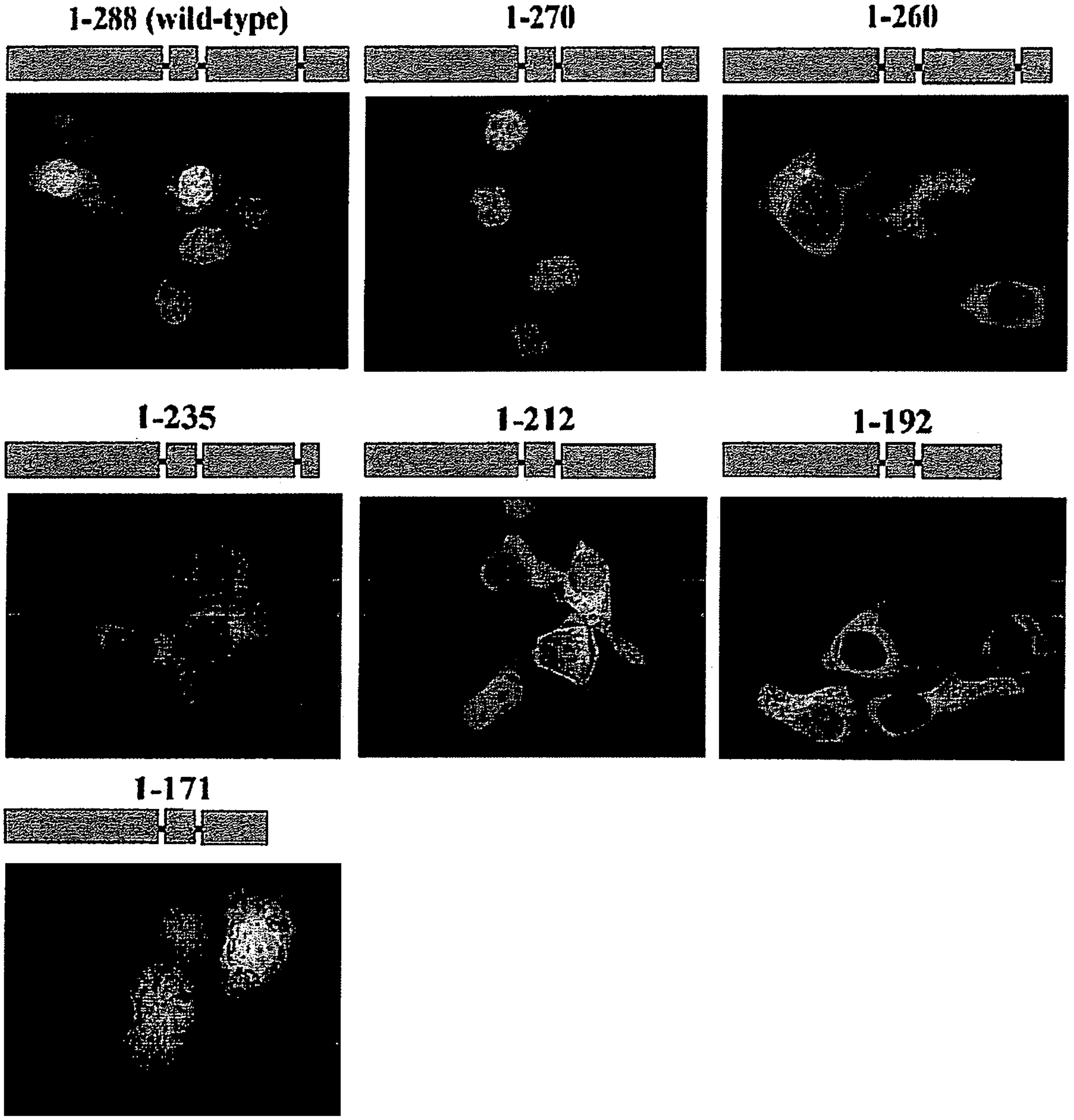

Residues in the Carboxyl-Terminus of Integrase are Determinants of Nuclear Localization Integrase has been mutagenized extensively in the context of numerous functional studies, but a systematic set of mutants has not yet been employed to localize determinants regulating its nuclear import. To identify determinants regulating nuclear import, a fluorescent marker for assaying the subcellular localization of integrase was constructed. (FIG. 1A). The integrase coding region (HIV-1 integrase (IN) open reading frame derived from the CXCR4-tropic, HXB-2 subclone, R7/3 HIV strain:

(SEQ ID NO: 2)
tttttagatggaatagataaggcccaagatgaacatgagaaatatcacag taattggagagcaatggctagtgattttaacctgccacctgtagtagcaa aagaaatagtagccagctgtgataaatgtcagctaaaaggagaagccatg -continued
```
catggacaagtagactgtagtccaggaatatggcaactagattgtacaca

tttagaaggaaaagttatcctggtagcagttcatgtagccagtggatata

tagaagcagaagttattccagcagaaacagggcaggaaacagcatatttt

cttttaaaattagcaggaagatggccagtaaaaacaatacatacagacaa

tggcagcaatttcaccagtgctacggttaaggccgcctgttggtgggcgg

gaatcaagcaggaatttggaattccctacaatccccaaagtcaaggagta

gtagaatctatgaataaagaattaaagaaaattataggacaggtaagaga

tcaggctgaacatcttaagacagcagtacaaatggcagtattcatccaca

attttaaaagaaaaggggggattgggggtacagtgcaggggaaagaata

gtagacataatagcaacagacatacaaactaaagaattacaaaaacaaat

tacaaaaattcaaaattttcgggtttattacagggacagcagaaatccac

tttggaaaggaccagcaaagctcctctggaaaggtgaaggggcagtagta

atacaagataatagtgacataaaagtagtgccaagaagaaaagcaaagat

cattagggattatggaaaacagatggcaggtgatgattgtgtggcaagta

gacaggatgaggattag
```

was fused to the carboxyl-terminus of enhanced green fluorescent protein (EGFP), and the construct was transfected into HEK293 cells. As expected, the 60 kD chimeric protein (EGFP-IN) localized predominantly to the nucleus in regions distinct from the nucleolus (FIG. 1B).

The amino acid sequence of the integrase protein is as follows:

```
                                              (SEQ ID NO: 3)
FLDGIDKAQDEHEKYHSNWRAMASDFNLPPVVAKEIVASCDKCQLKGEAM

HGQVDCSPGIWQLDCTHLEGKVILVAVHVASGYIEAEVIPAETGQETAYF

LLKLAGRWPVKTIHTDNGSNFTSATVKAACWWAGIKQEFGIPYNPQSQGV

VESMNKELKKIIGQVRDQAEHLKTAVQMAVFIHNFKRKGGIGGYSAGERI

VDIIATDIQTKELQKQITKIQNFRVYYRDSRNPLWKGPAKLLWKGEGAVV

IQDNSDIKVVPRRKAKIIRDYGKQMAGDDCVASRQDED.
```

An extensive set of charged-cluster-to-alanine mutations (Wiskerchen, M., and M. A. Muesing (1995) J. Virol. 69:376-386; Wiskerchen, M., and M. A. Muesing (1995) J. Virol. 69:597-601) and other point mutations were then introduced into the coding region of the integrase portion of the EGFP-IN construct (SEQ ID NOs: 4-65), and their effects on its subcellular localization were determined (FIG. 1F). A total of 64 individual or clustered mutations were created, covering 61 residues, including over 70% of all charged residues of the protein. Mutations reported by others as altering the cellular distribution of IN fusion proteins were included as well (Bouyac-Bertoia, M., Jet al (2001) Mol Cell 7:1025-35; Gallay, P., et al. (1997) Proc. Natl. Acad. Sci. USA 94:9825-9830). In contrast to these reports, mutation at residues 165, 166, 186, and 214-216 had no effect on the subcellular localization of the EGFP-IN fusion protein, although a triple mutant containing an alteration at 186 exhibited a pancellular distribution of fluorescence (FIG. 1F, Table 1).

Alanine substitutions within the carboxyl-terminus of IN, however, spanning residues 236-40 and 262-266, resulted either in partial (single substitution mutants) or complete exclusion of EGFP-IN from the nucleus (FIG. 1F, Table 2). For a subset of these mutants, transfected cells were growth-arrested by treatment with aphidicolin, or incubated at various temperatures.

To corroborate these results, a nested set of IN deletions originating from the carboxyl-terminus (Table 3) was examined in the context of EGFP-IN.

TABLE 3

C-terminal deletions in the Integrase coding region:

| Deletion Mutant Nucleotide sequence | Comprising amino acid residues | SEQ ID NO: |
|---|---|---|
| gaattacaaaaacaaattacaaaaattcaaaattt tcgggtttattacagggacagcagaaatccacttt ggaaaggaccagcaaagctcctctggaaaggtgaa ggggcagtagtaatacaagataatagtgacataaa agtagtgccaagaagaaaagcaaagatcattaggg at | 212-270 | 130 |
| gaattacaaaaacaaattacaaaaattcaaaattt tcgggtttattacagggacagcagaaatccacttt ggaaaggaccagcaaagctcctctggaaaggtgaa ggggcagtagtaatacaagataatagtgacataaa agtagtg | 212-260 | 131 |
| caaaattttcgggtttattacagggacagcagaaa tccactttggaaaggaccagcaaagctcctctgga aaggtgaaggggcagtagtaatacaagataatagt gacataaaagtagtgccaagaagaaaagcaaagat cattagggattatggaaaacagatggcaggtgatg attgtgtggcaagtagacaggatgaggat | 220-288 | 132 |
| agcagaaatccactttggaaaggaccagcaaagct cctctggaaaggtgaaggggcagtagtaatacaag ataatagtgacataaaagtagtgccaagaagaaaa gcaaagatcattagggattatggaaaacagatggc aggtgatgattgtgtggcaagtagacaggatgagg at | 230-288 | 133 |
| aagctcctctggaaaggtgaaggggcagtagtaat acaagataatagtgacataaaagtagtgccaagaa gaaaagcaaagatcattagggattatggaaaacag atggcaggtgatgattgtgtggcaagtagacagga tgaggat | 240-288 | 134 |
| gtaatacaagataatagtgacataaaagtagtgcc aagaagaaaagcaaagatcattagggattatggaa aacagatggcaggtgatgattgtgtggcaagtaga caggatgaggat | 250-288 | 135 |
| gtgccaagaagaaaagcaaagatcattagggatta tggaaaacagatggcaggtgatgattgtgtggcaa gtagacaggatgaggat | 260-288 | 136 |
| gattatggaaaacagatggcaggtgatgattgtgt ggcaagtagacaggatgaggat | 270-288 | 137 |
| caaaattttcgggtttattacagggacagcagaaa tccactttggaaaggaccagcaaagctcctctgga aaggtgaaggggcagtagtaatacaagataatagt gacataaaagtagtgccaagaagaaaagcaaagat cattagggat | 220-270 | 138 |

Subcellular localization of the deletion mutants was similarly examined (FIG. 1B and Table 4).

TABLE 4

Subcellular Localization of IN Deletion Mutants in the Context of Fusion to EGFP.

| IN Deletion Mutant: | Amino acid sequence | Nuclear Localization | Partial Change in Position | Nuclear Exclusion | SEQ ID NO: |
|---|---|---|---|---|---|
| 212-270 | ELQKQITK IQNFRVYYRDSRNPLW KGPAKLLWKGEGAVV IQDNSDIKVVPRRKAKI IRD | + | | | 139 |
| 212-260 | ELQKQITKIQNFRVYY RDSRNPLWKGPAKLL WKGEGAVVIQDNSDIK VV | | | + | 140 |
| 220-288 | IQNFRVYYRDSRNPLW KGPAKLLWKGEGAVV IQDNSDIKVVPRRKAKI IRDYGKQMAGDDCVA SRQDED | + | | | 141 |
| 230-288 | SRNPLWKGPAKLLWK GEGAVVIQDNSDIKVV PRRKAKIIRDYGKQMA GDDCVASRQDED | | | + | 142 |
| 240-288 | KLLWKGEGAVVIQDN SDIKVVPRRKAKIIRDY GKQMAGDDCVASRQD ED | | | + | 143 |
| 250-288 | VIQDNSDIKVVPRRKA KIIRDYGKQMAGDDCV ASRQDED | | | + | 144 |
| 260-288 | VPRRKAKIIRDYGKQM AGDDCVASRQDED | | | + | 145 |
| 270-288 | DYGKQMAGDDCVASR QDED | | | + | 146 |
| 220-270 | IQNFRVYYRDSRNPLW KGPAKLLWKGEGAVV IQDNSDIKVVPRRKAKI IRD | + | | | 147 |

Removal of the terminal 18 amino acids had no effect on nuclear localization (IN 1-270). However, removal of an additional 10 amino acids (IN 1-260), as well as more extensive deletions, led to nuclear exclusion (FIG. 1B). Pancellular distribution was also observed for several other EGFP-IN carboxyl-terminal deletions extending further into the core as well as the amino-terminal domains of integrase in which greater numbers of amino acid residues of integrase were removed (data not shown). Demonstrable nuclear transport occurred during cell cycle and G1 growth arrest by treatment with aphidicolin, as well. Results were identical under all conditions tested.

Figure 1C:
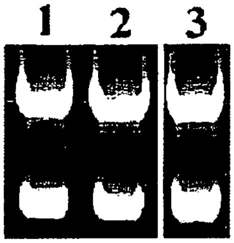
Figure 1D:
Figure 1E:
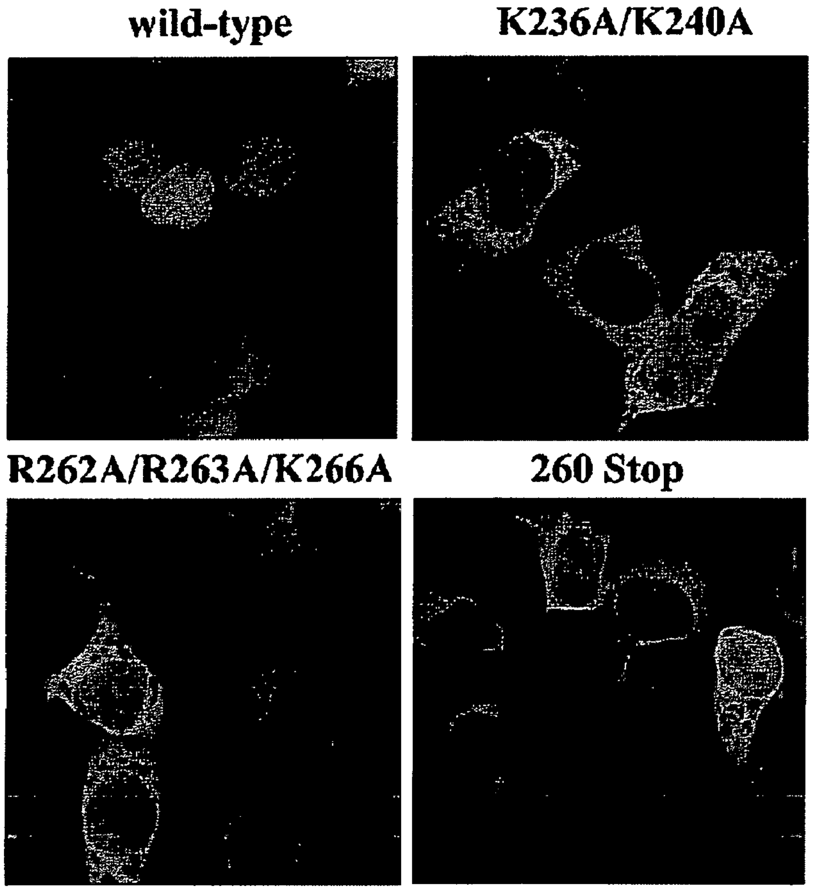

Chimeric proteins generated as indicator fusions or as epitope-tagged versions may have different biochemical properties than the individual components in their respective native states. To determine whether mutations affecting the subcellular localization of EGFP-IN had similar effects in the context of native integrase, it was first necessary to optimize native IN expression. Although mRNA encoding HIV-1 integrase is metabolically stable as part of the natural genomic mRNA during infection or in artificial fusion constructs such as pEGFP-IN or pEGFP-IRES-Ub-IN, it is unstable when expressed in isolation (FIG. 1C). Therefore, the coding sequence of IN was modified by introducing 297 codon-synonymous nucleotide substitutions (IN-MOD) (SEQ ID NO: 1). In contrast to the wild-type coding sequence, the IN-MOD reading frame is capable of stable mRNA accumulation (FIG. 1C), with correspondingly much higher levels of the integrase protein (FIG. 1D). The putative carboxyl-terminal NLS mutations were then introduced into this modified integrase expression construct, and the localization of the wild-type and mutant proteins examined inmiunocytochemically. Native IN localized to the nucleus, while the carboxyl-terminal NLS alanine substitution mutants were restricted to the cytoplasm (FIG. 1E). Given that the 32 kD IN might be expected to diffuse passively through the nuclear pore, our results indicated that these particular mutants were still able to homo-multimerize in vivo, as has been reported for wild-type IN.

Example 2

The Integrase NLS is Highly Conserved Among Primate Lentiviridae, and in Particular, Among Multiple HIV Clades Conservation of the carboxy-terminus of the integrase protein was demonstrated in multiple primate lentiviridae. Underlined residues in Table 4 of Example 1 indicate highly conserved residues among HIV-1 strains, and various SIVs (FIG. 2). The conservation is complete both in placement and sequence regarding HIV coordinants K236, R262, R263, K266, and somewhat at K240, as well. For the non-primate lentiviridae EIAV, FIV, BIV and Visna virus, the overall pattern of basic residue placement can be discerned as well. Clusters of basic residues are roughly 25-30 amino acids apart. Hydrophobic residues involved in maintaining the SH3 monomeric structure, and those involved in maintaining the SH3:SH3 dimer interface were as indicated.

Figure 4:
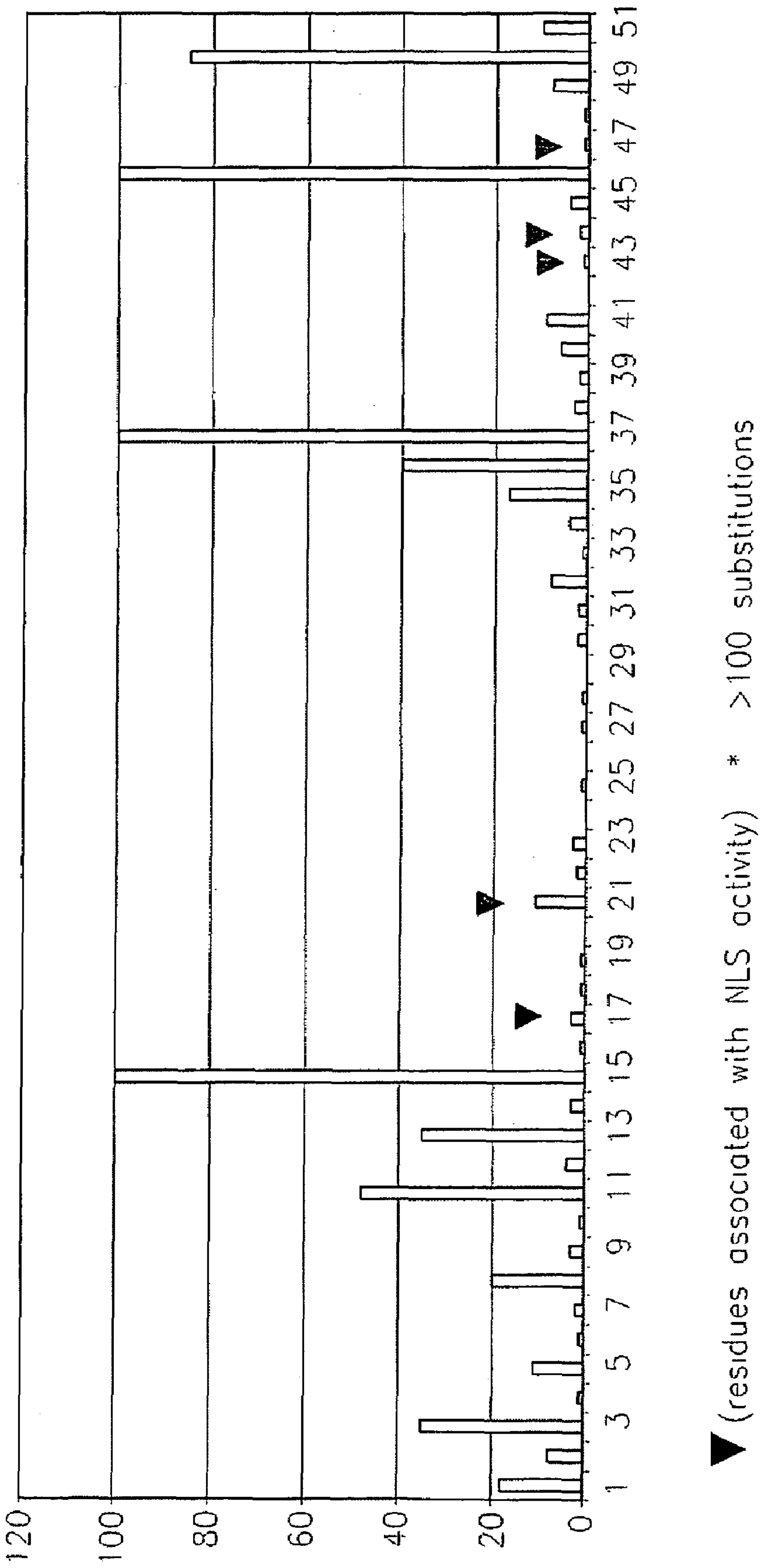
FIG. 4 graphically depicts the data presented in FIG. 3.

520 HIV independent proviral DNA sequences representing major clade groups were subjected to BLAST analysis via the HIV Sequence Database maintained on the Worldwide Web by The Los Alamos National Laboratories. The database was queried with the nucleotide sequence as set forth in SEQ IID NO: 147. The frequency of substitution of individual residues is depicted in FIG. 3, and displayed graphically in FIG. 4. The substitutions identified for each position in the clades evaluated is presented in FIG. 5.

Example 3

The C-terminus of HIV Integrase Contains a Transferable NLS

Figure 6A:
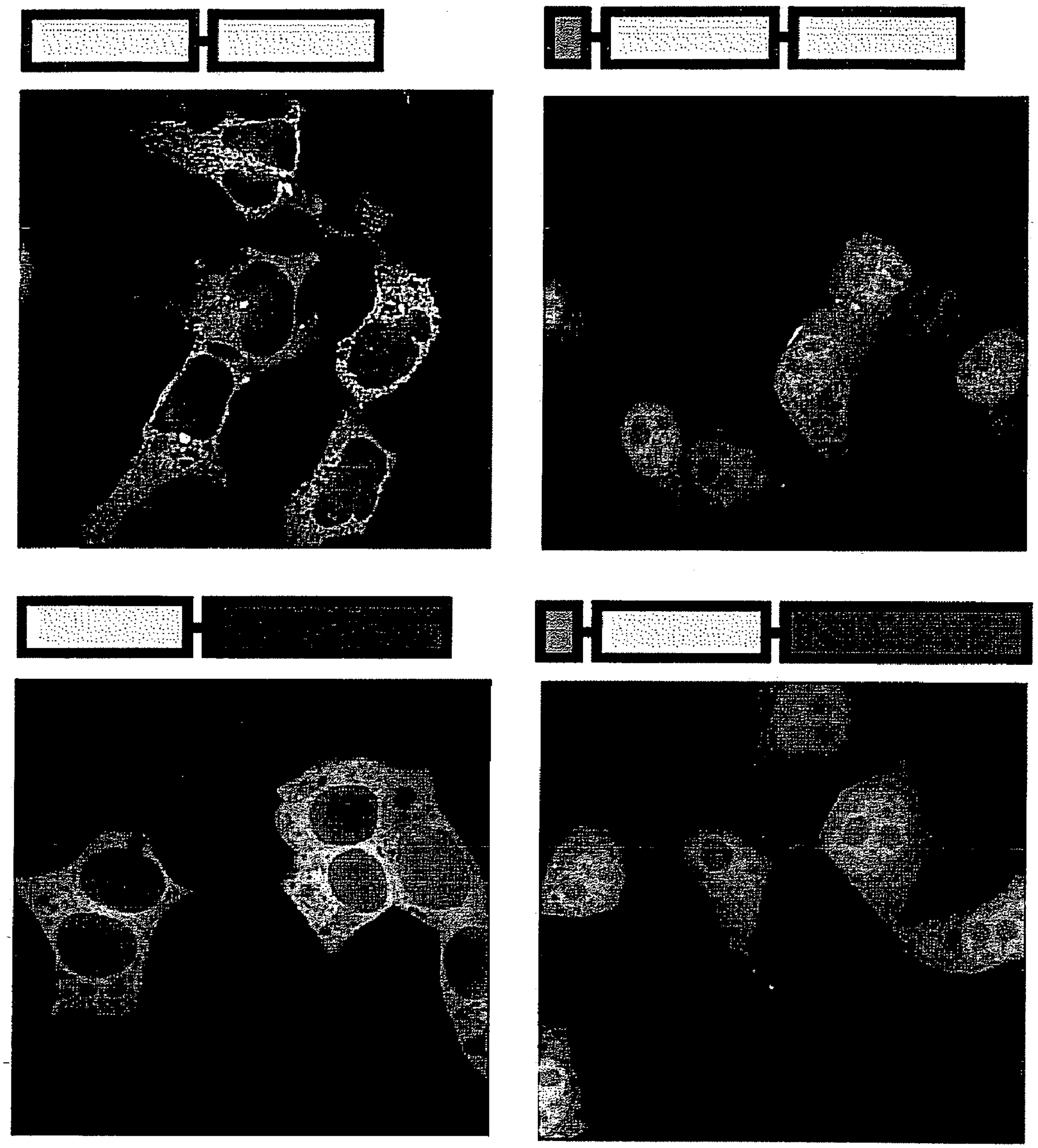
FIG. 6 shows that the carboxyl-terminal domain of HIV-1 integrase contains a transferable NLS. EGFP-EGFP and EGFP-MBP with or without the integrase NLS domain (IN-COOH) positioned at the amino terminus of the fusion protein partner (A). The nuclear exclusion phenotype associated with mutant integrase protein is recapitulated in the context of $IN^{COOH}$ positioned at either terminus of EGFP-MBP (B, amino-terminus; C, carboxyl-terminus). M1: $IN^{K236A/K240A}$, M2: $IN^{R262AR263AK266A}$, M3: $IN^{260\ Stop}$. The end-points of the integrase SH3 domain are required for NLS activity. A nested set of mutants removing consecutive 10 amino acid segments (arrow) from the integrase portion of the $IN^{COOH-EGFP-MBP}$ fusion protein was examined for NLS activity as above (D). Shown at upper right is a ribbon diagram (RasMol) of the revised structure of the SH3 domain specified by the amino acids 220-270 within the carboxyl terminal region (212-288) of HIV-1 integrase. Amino acids between 220 and 230 (blue) are required for NLS activity in addition to the charged-clusters at 236/240 and 262/263/266 as defined above. Western blot of the integrase-EGFP-MBP fusion proteins used in FIGS. 2A-D (E). 293T cells were transfected and probed with a mouse monoclonal antibody specific for EGFP developed and re-probed with an antibody specific for γ-tubulin. Lane: (1) mock transfected, (2) EGFP-MBP, (3-13): $IN^{COOH-EGFP-MBP}$ wild-type, deletion and point-mutant derivatives: (3) wild-type 212-288, (4) 220-288, (5) 230-288, (6) 240-288, (7) 250-288, (8) 260-288, (9) 270-288, (10) molecular weight marker, (11) mock transfected, (12) EGFP-MBP, (13) wild-type 212-288, (14) $IN^{k236A/K240A}$ (212-288), (15) $IN^{R262A/R263A/K266A}$ (212-288), (16) molecular weight marker, (17-20): EGFP-MBP-$IN^{COOH}$ wild-type and point-mutant derivatives: (17) wild-type 212-288, (18) $IN^{K236A/K240A}$ (212-288), (19) $IN^{R262A/R263A/K266A}$ (212-288), (20), $IN^{260\ Stop}$ (212-288).
Figure 6B:
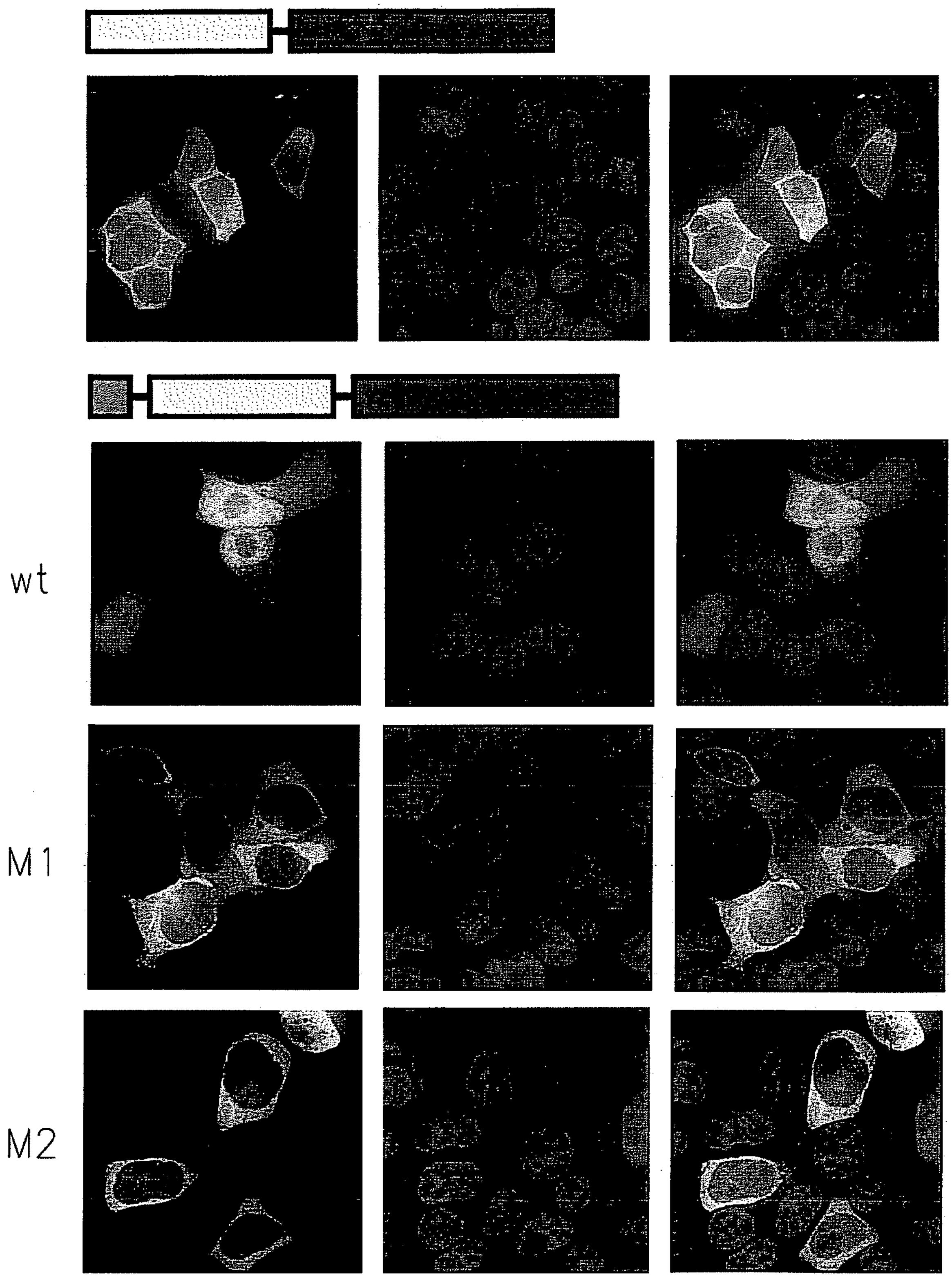
Figure 6C:
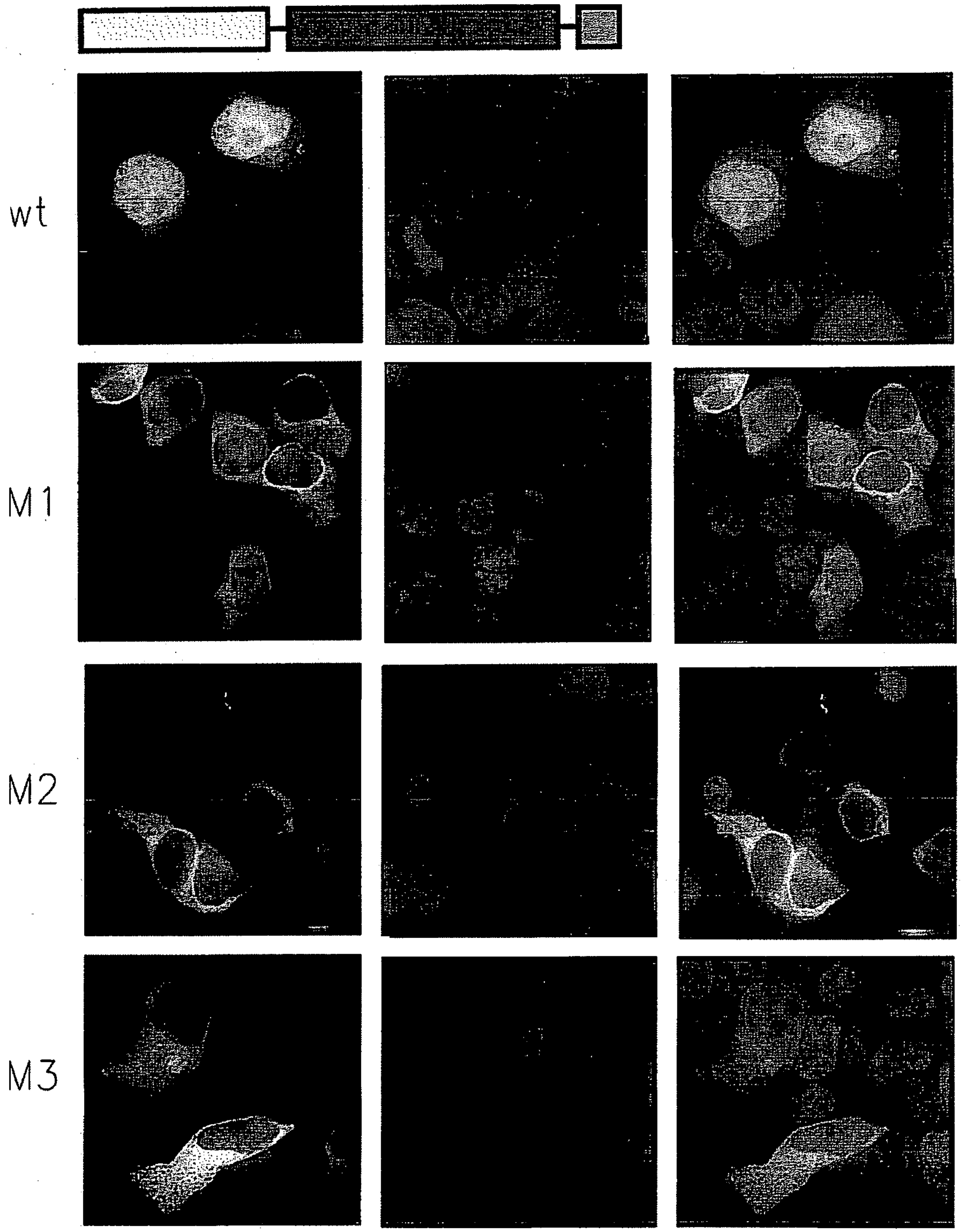

A hallmark of NLS functionality is the ability of an NLS-containing polypeptide to confer nuclear localization to a large protein that is otherwise cytoplasmic. To determine whether the carboxyl-terninal domain of IN contains such a transferable NLS, two large, fluorescent, chimeric proteins that are unable to enter the nucleus (pEGFP-EGFP, 59 kD and pEGFP-MBP, 74 kD) were constructed. Both proteins localized entirely to the cytoplasm of transfected cells (FIG. 6A). However, constructs comprising a nucleotide sequence encoding for the addition of the carboxyl-terminal domain of IN: gaattacaaaaacaaattacaaaaat-tcaaaattttcgggtttattacagggacagcagaaatccactttggaaaggacca gcaaagctcctctggaaaggt-gaaggggcagtagtaatacaagataat-agtgacataaaagtagtgccaagaagaaaa gcaaagatcattagggattatg-gaaaacagatggcaggtgatgattgtgtggcaagtagacaggatgaggattag (SEQ ID NO: 148), spanning residues 212-288 ELQKQIT-KIQNFRVYYRDSRNPLWKGPAKLLWKGE-GAVVIQDNSDIKV VPRRKAKIIRDYGKQMAGD-DCVASRQDED* (SEQ ID NO: 149), caused all cytoplasmic substrates to relocalize to the nucleus of transfected cells (again in regions distinct from the nucleolus), indicating the existence of a transferable NLS in this region of integrase (FIG. 6A). The integrase NLS was functional regardless of its placement at either the amino- or carboxyl- terminus of the test protein (FIGS. 6B and C). Significantly, substitution of the charged-cluster-to-alanine NLS mutations in these constructs results in a protein that is unable to -access the nucleus (FIGS. 6B and C), recapitulating the phenotype observed in the context of both the EGFP-IN fusion and the full-length native integrase protein.

Figure 6D:
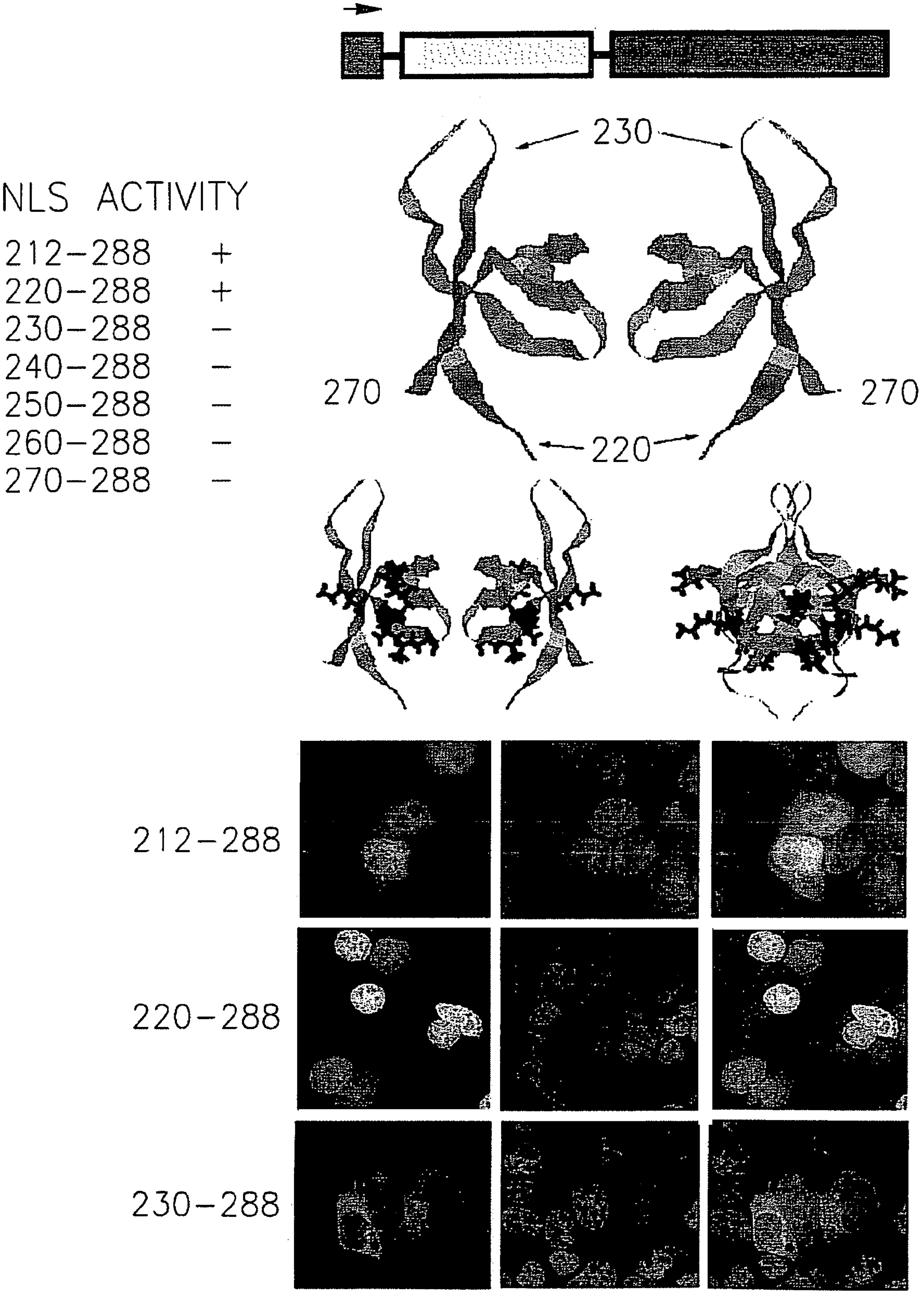
Figure 6E:
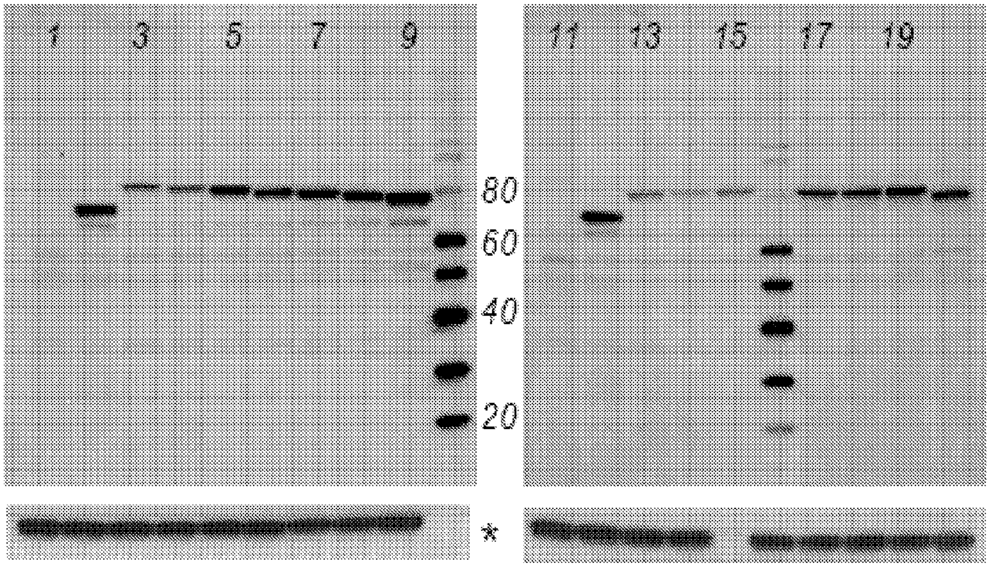

In an effort to map the amino-terminal endpoint of the integiase NLS, progressive amino-terminal deletion mutants originating from position 212 were constructed and examined for NLS activity (FIG. 6D). Interestingly, nuclear localization activity was lost in mutants with deletions between amino acid residues 220 and 230 (SEQ ID NO: 131-137) (See Table 4) even though the basic residues at 236/240 and 262/263/266 are maintained in the IN230-288-EGFP-MBP fusion protein. The cumulative results define a contiguous segment of primary amino acid sequence of HIV-1 integrase required for NLS activity, bounded at the amino-terminal end by residue 220 and at the carboxyl-terminus at position 270 (SEQ ID NO: 147). These amino acid residues are co-linear to those that define an SH3-like structural analog, as determined by NMR spectroscopy. Thus, it is plausible that the integrase NLS is defined not only by the relevant charged-clusters of basic amino acids described here but also by the structural context in which these residues normally exist.

Although basic residues were critical for NLS activity, there is little homology to classic, bipartite, or basic NLSs such as that of nucleoplasmin (NP). Interestingly, unlike canonical nuclear localization signals, the IN NLS activity cannot be transferred as a small peptide unit but instead requires the region of the protein spanning residues 220-270. This region of HIV integrase is dimerized in solution, each monomer adopting an SH3-like fold. In this configuration, a highly charged surface is created at the solvent interface by the contribution of the basic residues at positions 236/240 and 262/263/266, each cluster contributed by a separate monomeric unit. Thus, orientation of the constituent residues of the NLS within the context of a larger three-dimensional space may be critical to its function.

Figure 7A:
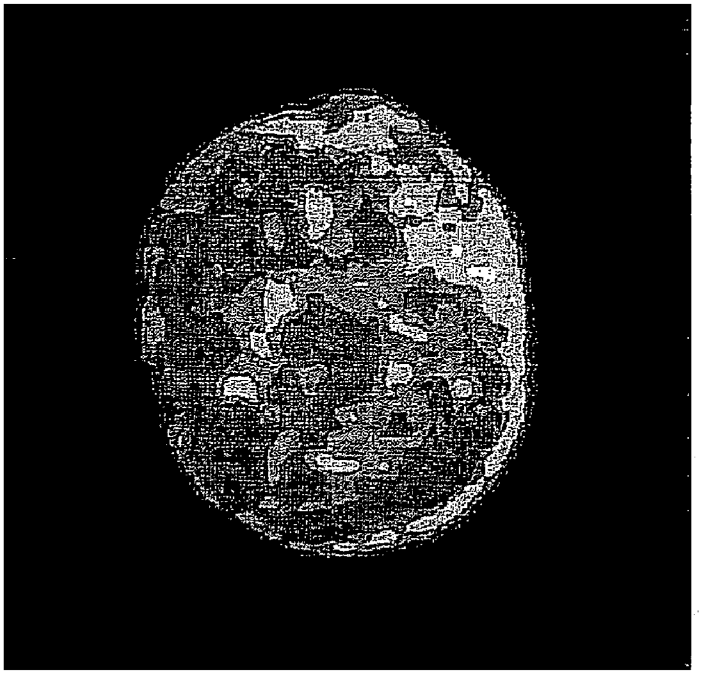
FIG. 7 demonstrates integrase NLS coordination of nuclear localization in primary human CD4+ lymphocytes. Cells were purified from blood and transfected by nucleofection (AMAXA, Inc.) with the indicated plasmid DNA. Cells were visualized 24 hours later for both the location of EGFP and DAPI, a nuclear counterstain. EGFP-MBP-IN (212-288) wild-type (Left), EGFP-MBP-IN (212-288) R262A/R263A/K2(Right).
Figure 7B:
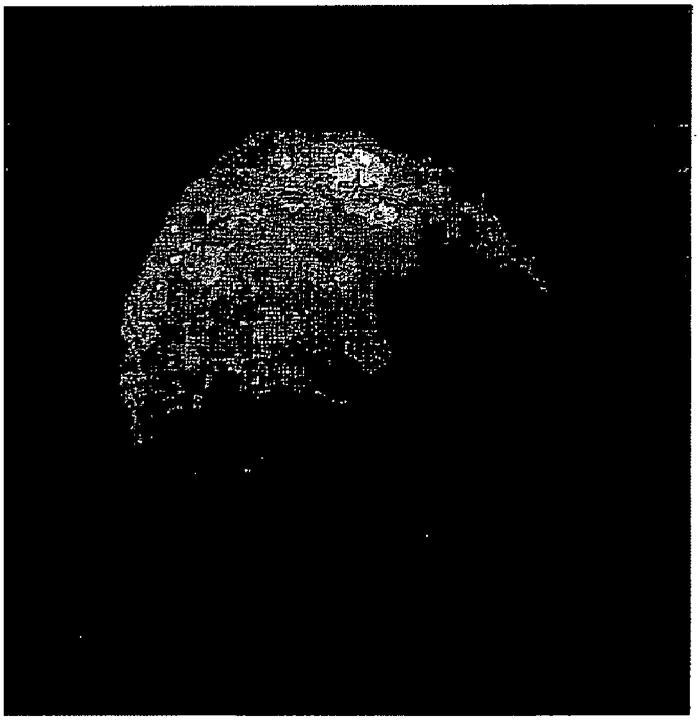
Figure 8A:
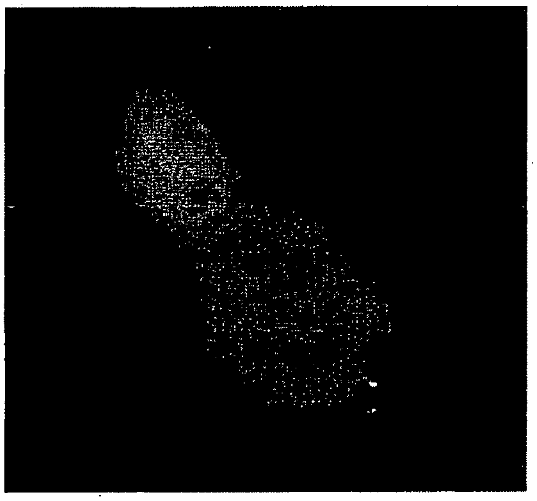
FIG. 8 demonstrates integrase NLS coordination of nuclear localization in primary, non-dividing human dendritic cells. Cells were purified from blood and transfected by nucleofection (AMAXA, Inc.) with EGFP-MBP-IN (212-288) wild-type (A, B) and EGFP-MBP-IN (212-288) R262A/R263A/K266A (C, D) plasmid DNA. Cells were visualized 24 hours later for both the location of EGFP (A, C) and DAPI (B, D), a nuclear counterstain.
Figure 8B:
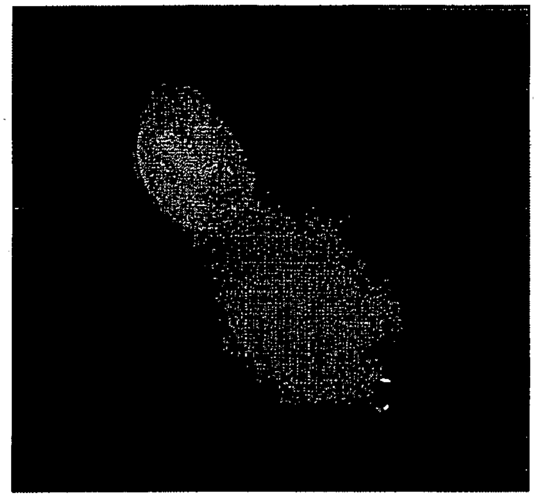
Figure 8C:
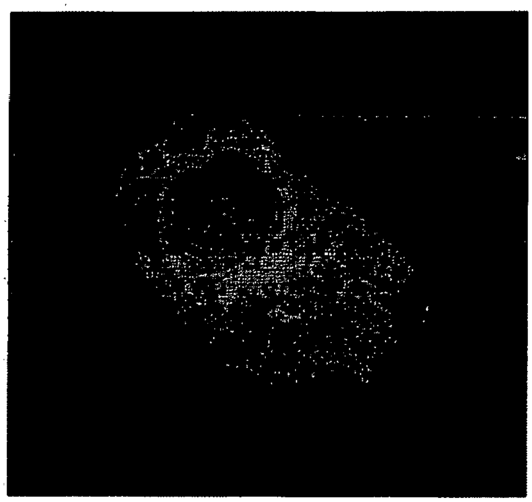
Figure 8D:
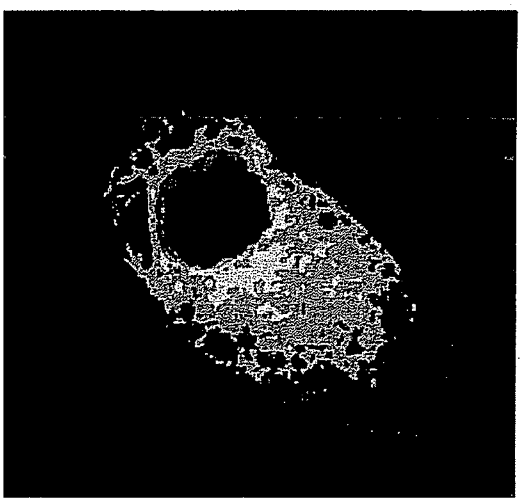

The integrase NLS coordinates nuclear localization in primary, non-dividing human CD4+ lymphocytes (FIG. 7), and in primary, non-dividing dendritic cells (FIG. 8). Further, another unique finding regarding the HIV NLS was that the NLS mimics the behavior of HIV during natural infection, with regard to the activation status of the host. Purified primary CD4+ lymphocytes and dendritic isolated and transfected with EGFP-MBP-IN (220-270) were transported to the nucleus, which was abrogated in integrase NLS mutants, however T-cell activation was required for nuclear transport, which was unique to the HIV-integrase constructs. Control cells, transfected with a construct comprising the NLS of nucleoplasmin, NLSnp-EGFP-EGFP was transported to the nucleus of the T cells, regardless of its activation status, in marked contrast to that of cells transfected with EGFP-MBP-IN (220-270).

Example 4

Integrase NLS-Mutant Viruses are Replication Defective

To examine the effects of the integrase NLS mutations identified above in the context of the HIV life cycle, each NLS mutation was introduced into an otherwise infectious HIV-1 proviral DNA clone, R7/3. None of these mutants overlap with the splice acceptor of the vif gene or its reading frame. In all cases, the vpr reading frame, which terminates prematurely in R7/3, was repaired. For experiments involving infection of monocyte-derived macrophages (MDM), the gp120 domain of the CXCR4-tropic envelope protein (env) of R7/3 was replaced with the same domain from the CCR5-tropic env of the primary isolate clone, YU-2.

Figure 9A:
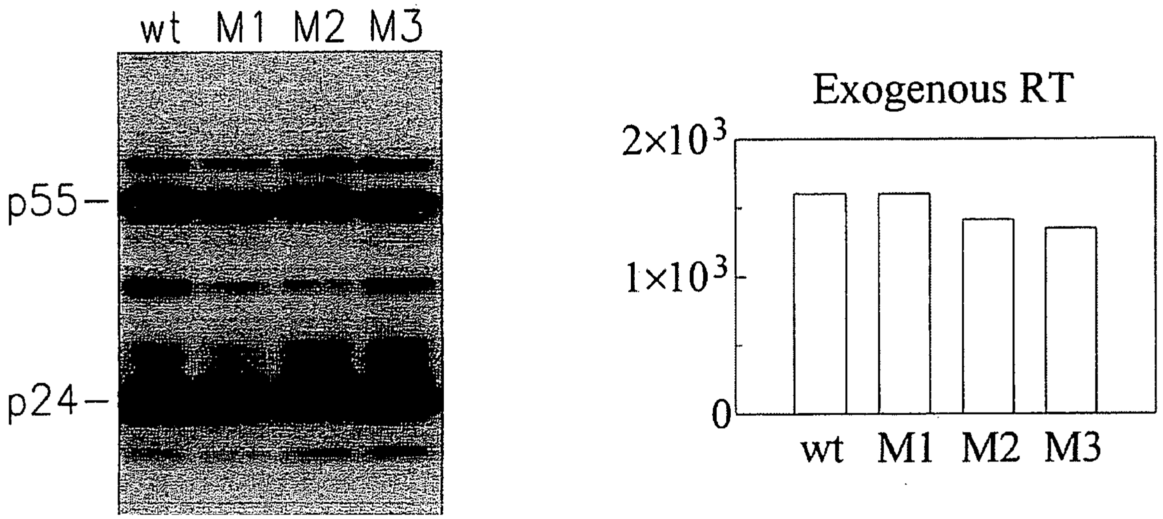
FIG. 9 shows that HIV-1 integrase NLS mutations do not perturb viral production or in vitro properties but are replication-defective regardless of cell division. Western blot analysis of cells transfected with the wild-type or NLS-mutant proviral construct (A). Virions were pelleted by ultracentrifugation from producer cell supernatants, normalized for p24 CA content and probed using AIDS patient anti-sera (upper) or with the anti-integrase mouse monoclonal antibody, 6G5 (lower). Comparative reverse transcriptase activity in wild-type and NLS-mutant virions (B). Virus was prepared as above, normalized for p24 content, and assayed for enzymatic, exogenous template added RT activity (upper) and RT activity on the intravirion endogenous viral RNA template (lower). A representative experiment is shown for each. Time Course of p24 CA production by infected MDM, CEM-SS and PBL cells (left) (C). Cells were infected with viruses containing the indicated IN mutation, and soluble p24 CA production measured over the indicated time period (Macrophage, R5 virus; CEM-SS and PBL, X4 virus). Single-cycle infections in dividing and growth-arrested P4-CCR5 (HeLa) cells (right) (D). Cells (either untreated or treated with aphidicolin) were infected with R5 viruses containing the indicated IN mutation. Tat-induced β-Galactosidase reporter gene activity was quantified at 48 hours post-infection wt (1,5), 236/240 (2,6), 262/263/266 (3,7), 260 stop (4,8). 1-4 (X4), 5-8 (R5).
Figure 9B:
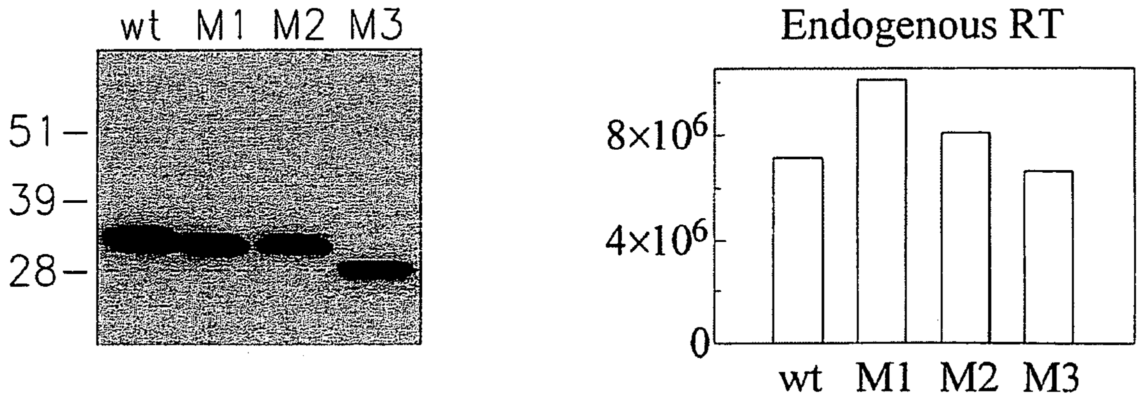

Integrase NLS-mutant viruses were first characterized for defects in virion production, protein incorporation and/or polyprotein processing. The wild-type and mutant viruses were produced with equal efficiency in 293T cells, as measured by the amount of p24 (CA) protein, and expressed and processed the Gag-Pol precursor protein correctly. Wild-type levels of the constituent Gag-Pol proteins were found for all of the replication-defective NLS viruses, indicating that the mutations had no detectable effect on Gag processing or incorporation (FIG. 9A, upper). No difference in the amount of integrase protein relative to wild-type was detected in mutant virion preparations (FIG. 9A, lower). Wild-type and NLS-mutant virions were also examined for reverse transcriptase activity by both measurement of radioactive deoxynucleotide incorporation using exogenously added template (FIG. 8B, upper) and by quantification of the synthesis of nascent transcripts from the endogenous, viral template using real-time PCR (FIG. 9B, lower). The amount of enzymatically active RT incorporated into virions as well as the efficiency of endogenous reverse transcription was identical for all viruses. Thus integrase NLS mutations do not alter Gag-Pol processing, levels of matrix, core, or integrase proteins packaged into virions, or inherent reverse transcriptase activity.

Figure 9C:
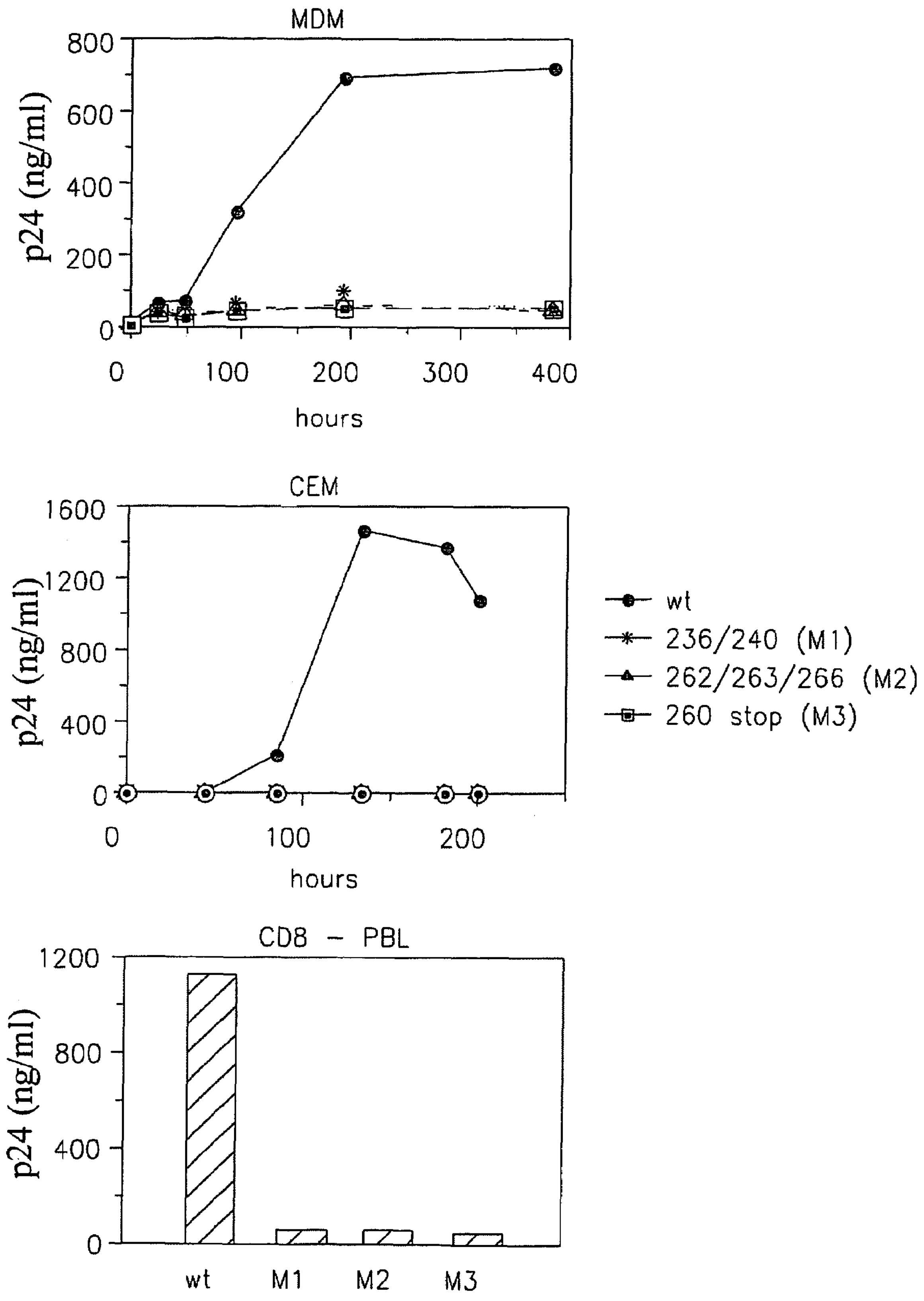
Figure 9D:
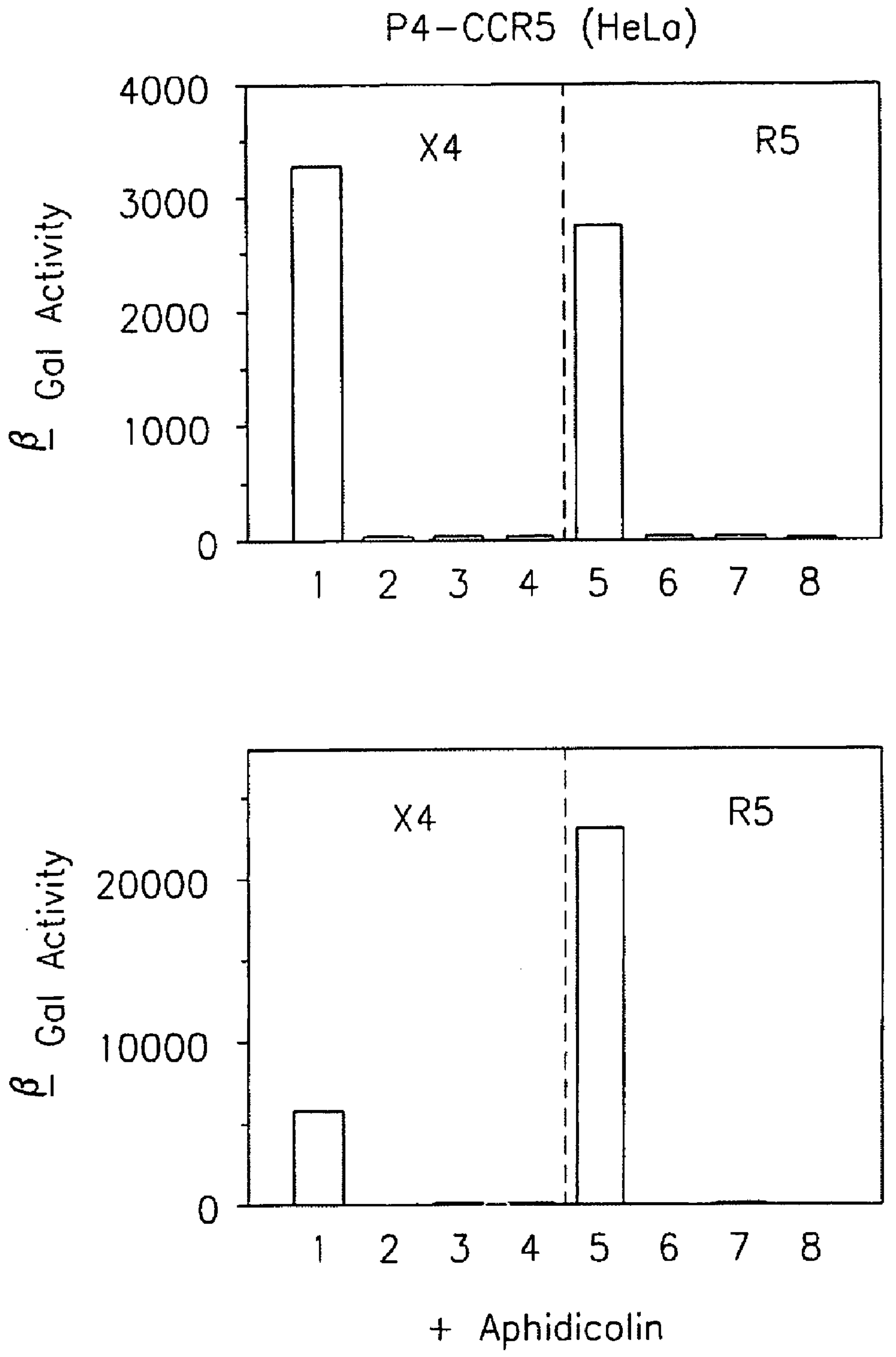

Next, integrase NLS mutations were examined for their effects on viral replication in a variety of cell types. As would be expected for viruses compromised for nuclear import, infections of monocyte-derived-macrophages with the integrase NLS mutant viruses were non-productive (FIG. 9C). Interestingly, the same mutant viruses (isogenic except for the CXCR4-tropic env gene substitution) were also replication-defective in the cycling CEM-SS T-lymphoblastoma cell line and activated cultures of CD8-depleted peripheral blood lymphocytes. Similar results were observed during single-cycle infections of the HeLa-derived, P4-CCR5 β-galactosidase indicator cell line. NLS-mutant viruses were unable to induce Tat-mediated indicator gene expression in either dividing P4-CCR5 cells or those arrested with aphidicolin in the G1 phase of the cell cycle (FIG. 9D). Thus, these results suggest that IN NLS-mutant viruses are likely compromised at an early stage of the HIV life cycle, prior to nuclear entry and tat gene-induced viral transcription.

Example 5

Infection with Integrase NLS-Mutant Viruses Exclusively Affects Nuclear Import in Infection of Primary Cells To examine the effects of NLS mutants on specific early stages of the HIV life cycle, a series of sensitive, stage-specific real-time PCR-based assays that quantitatively measure progression through reverse transcription and nuclear import were conducted. In agreement with other kinetic PCR assays, calibration of a typical spreading infection of CEM-SS cells with wild-type virus R7/3 exhibits a 2- to 4-log increase over baseline for each of the viral DNA intermediates over 48 hours, as the stage-specific products appear sequentially (data not shown). Notably, the copy number per cell equivalent of each stage-specific product is approximately 1-2 orders of magnitude less than the previous step, highlighting the relative inefficiency of the conversion of viral RNA into the nuclear viral DNA species.

Single-cycle infections with wild-type and NLS-mutant R5 and X4 viruses were performed in MDM and CD8-depleted, activated primary lymphocytes, respectively. In all cases, the integrase strand-transfer inhibitor L-731,988 was added during infection. This inhibitor has no effect on the nuclear localization of the enzyme (data not shown) or viral DNA accumulation in the nucleus but renders it catalytically inactive at the strand-transfer step (27). First, this allowed for all viruses to be compared in a single round of infection. Second, it increased the utility and accuracy of the 2-LTR circle assay as a marker for PIC nuclear import by eliminating potential variations in integration efficiency between the wild-type and mutant viruses. This is important for avoiding confounding effects, since the frequency of viral integration is inversely correlated with the accumulation of the circular viral DNA species found in the nucleus.

Figure 10B:
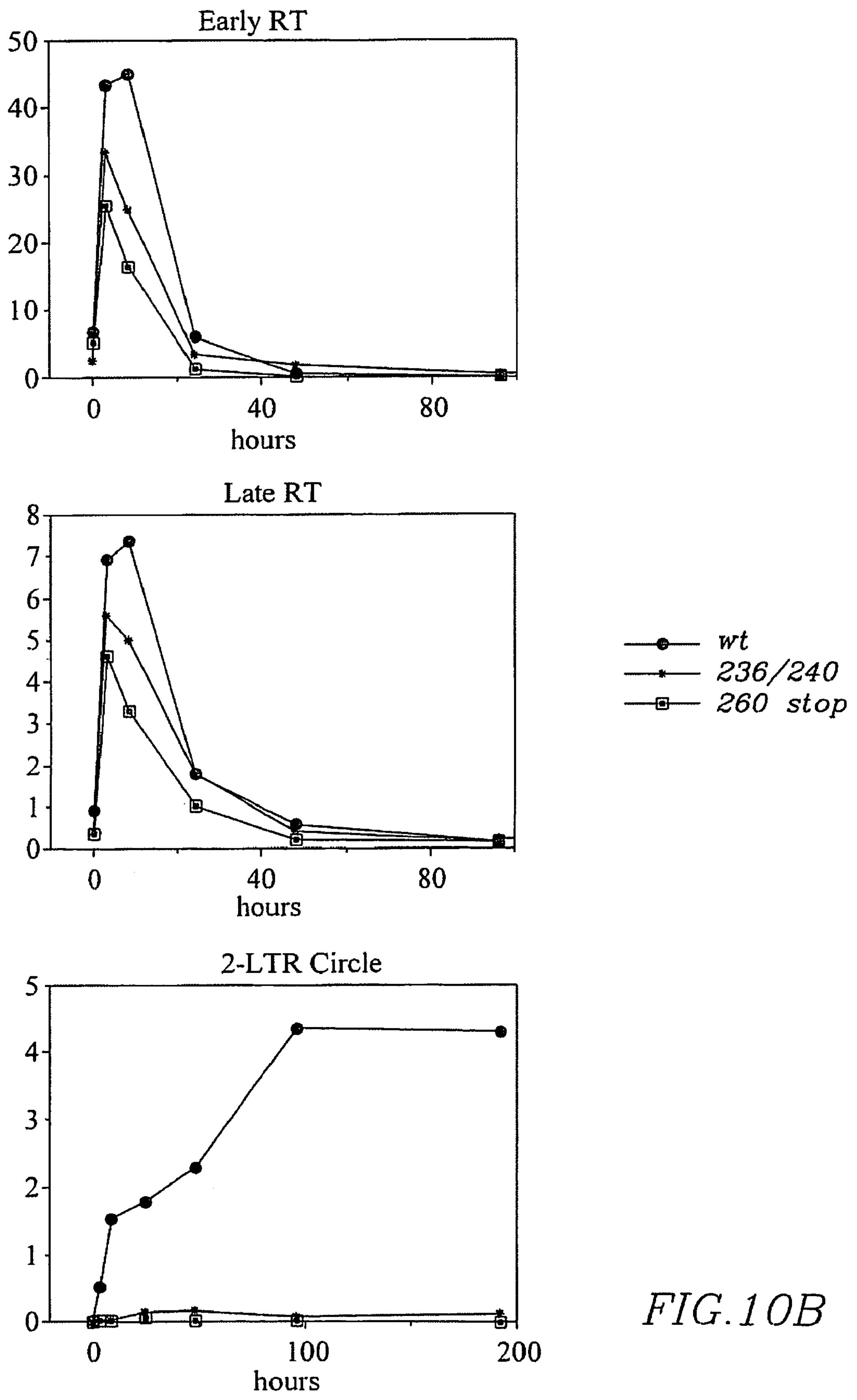
FIG. 10 shows via kinetic PCR analysis of viral DNAs after infection that NLS-mutant viruses are defective for nuclear import in primary cells and immortalized cell lines. Viral DNA products from single cycle infections of MDM and CD8-depleted PBLs monitored over time (A). Cells were infected with equivalent amounts (200 ng p24 CA) of R5 (MDM) or X4 (PBL) wild-type or integrase NLS-mutant viral stock, with infection enhanced by spinoculation. Subsequent levels of viral reverse transcripts and 2-LTR circles were measured at various times post-infection using real-time PCR analysis, and normalized on a per-cell basis using CCR5, a single-copy gene. The integrase inhibitor L-731,988 was added 6 hours post-infection to control for downstream effects on 2-LTR circle accumulation. A representative experiment is shown Single-step infection of primary human macrophages in the absence of the integrase inhibitor, L-731, 988 (B). Viral Infections were initiated as in A however, each virus contained an additional integrase mutation (D116A) at the catalytic site. Titration of X4 and R5 viruses on primary or immortalized cells revealed a cell-type specific reverse transcriptase defect associated with mutation in the integrase NLS (C). Cells were infected by spinoculation in 24-well format with 1,3,9,27,81 or 243 ng (p24 CA) of viral stock. Four hours post-infection total intracellular DNA was isolated and assayed for late reverse transcripts. A pharmacologically-isolated population of newly-synthesized HIV-1 DNA is defective for nuclear import in IN-NLS mutant viruses (D). MDM were infected with either wild-type or IN NLS mutant virus in the presence of integrase inhibitor L-731,988. At three hours post-infection, a reverse transcriptase inhibitor, UC781, was added to inhibit further viral DNA synthesis.

FIG. 10A shows that while wild-type and integiase NLS-mutant viruses are able to complete the late stage of reverse transcription with equal efficiency, all NLS-mutant viruses exhibit a severe defect in proviral nuclear import, as measured by 2-LTR circle formation, in both macrophages and activated lymphocytes. In order to ensure that the presence of a pharmacological integrase inhibitor did not confound our results by exerting pleiotropic effects, experiments were repeated in the absence of the drug. Here, MDM were infected with wild-type and NLS-mutant viruses containing an additional mutation, IN D116A, which by itself has no effect on nuclear localization of the integrase protein (Table 1) or reverse transcription (see below) or transport of the viral genome into the nuclear compartment but prevents integration and further progression through the viral life cycle. Results using these viruses were the same as those obtained using the small molecule integrase inhibitor, with a specific and severe two-log defect evident at the level of 2-LTR circle formation (FIG. 10B). Thus, the functional integrase NLS described here is necessary for efficient nuclear accumulation of the viral genome in the context of infection in cell types relevant for HIV infection in vivo.

Under a wide variety of experimental conditions, the steps preceding nuclear import of the viral genome during single-cycle infection were indistinguishable between wild-type and the NLS mutant viruses. Yet, the accumulation of nuclear viral LTR circular DNAs differed dramatically in absolute number between the two types of viruses. The difference was detected early (24 hours post-infection) and persisted throughout each 8-day experiment, reaching a two-log difference in LTR circle accumulation for each of the three NLS mutants examined. Interestingly, the phenotypes of NLS mutations were manifest in both dividing and non-dividing cells. While, this is similar to what has been observed for alterations in the cPPT, it differs from the phenotype of MA and Vpr NLS mutants, where replicative defects are seen primarily in non-dividing cells.

Over the course of our experimentation, we observed that IN NLS-mutant viruses exhibit an additional replicative defect, apparent at the earliest stage of reverse transcription, in certain immortalized cell-lines. To understand the relationship between nuclear localization and reverse transcription in the context of the identity of the infected cell, we determined the level of late reverse transcripts over a two-log range of X4 and R5 viral input inocula (1-243 ng p24). Total cellular DNA was isolated four hours after infection and the amount of late reverse transcription product was determined for each of the immortalized cell lines, CEM-SS, P4-CCR5 (HeLa) as well as primary cultures of MDM and CD8-depleted PBLs (FIG. 10C). Remarkably, a decreased efficiency of reverse transcription was manifest for NLS mutants in CEM-SS cells but not PBL, P4-CCR5 (HeLa) or MDM, regardless of the input inoculum. This cell-type specific effect was unanticipated and reveals an additional level of complexity with regard to the interpretation of nuclear transport studies using immortalized cell lines, suggesting that cell lines may not reflect accurately the events occurring during infection of primary cells.

Figure 10D:
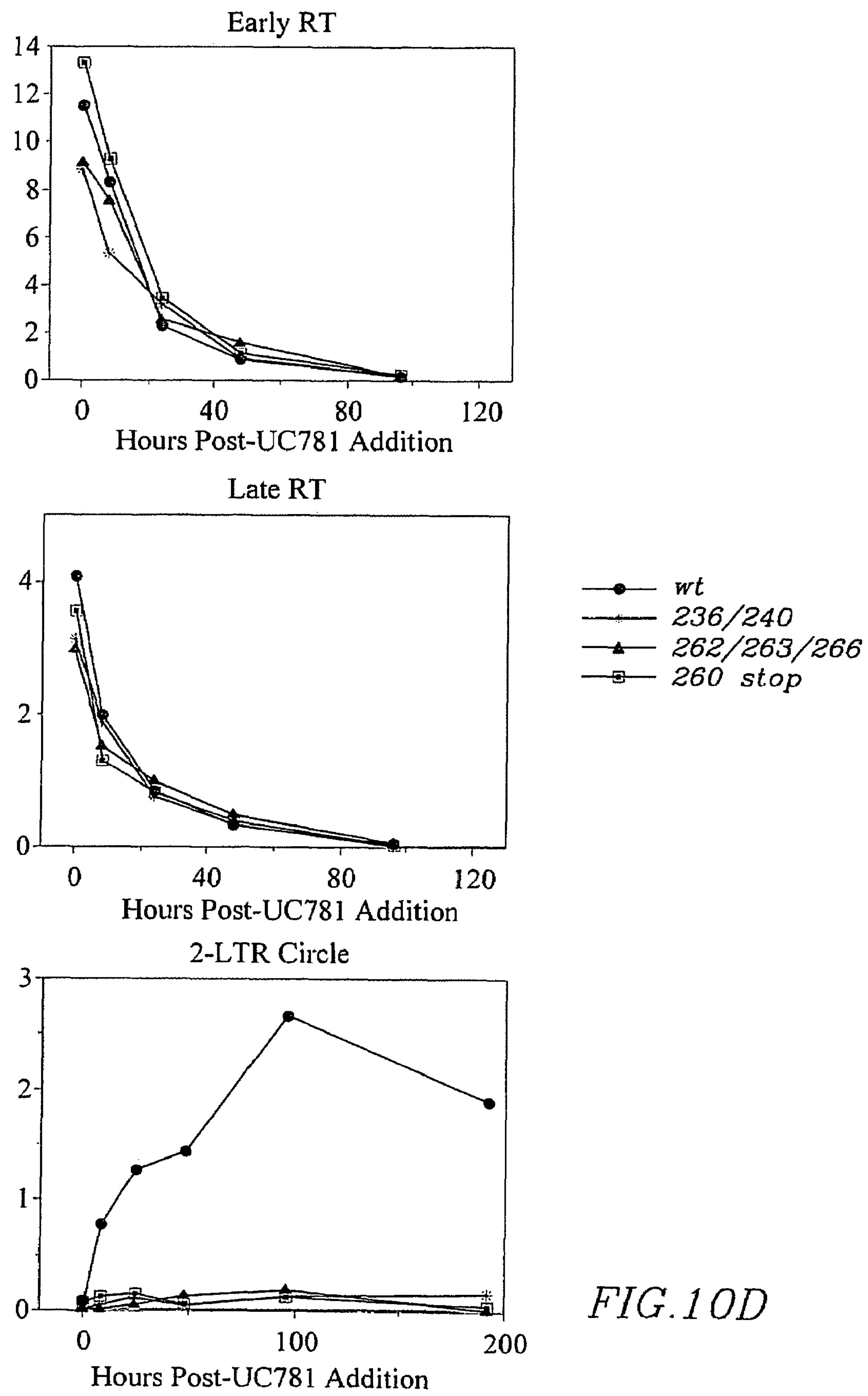

To ensure that the role of integrase in viral nuclear import was independent of upstream events of the viral life cycle, we attempted to pharmacologically isolate and monitor a single population of reverse transcripts for nuclear import. MDM were infected with either wild-type or IN NLS mutant virus in the presence of the integrase inhibitor as described above. At 3 hours post-infection, the non-nucleoside reverse transcriptase inhibitor, UC781, was added to block further DNA synthesis, and the levels of reverse transcript and 2-LTR circle formation monitored by real-time PCR. Under these conditions, both the production and stability of viral cDNA transcripts were identical in the wild-type and mutant viral infections (FIG. 10D). However, 2-LTR circle formation was dramatically reduced for the IN K236A/240A virus relative to the wild-type, indicating a specific and severe defect for nuclear import when this stage of the viral life cycle is pharmacologically uncoupled from upstream and downstream events.

Example 6

Integrase NLS Mutants are Capable of Providing Catalytic Activity During Infection Although severely compromised for the ability to gain access to the nuclear compartment, the integrase NLS mutants are nonetheless capable of providing integrase enzymatic function in trans, by means of intravirion complementation. Viral stocks prepared by co-transfection of either the wild-type or NLS-mutant proviral DNAs with pVPR-PC-IN, an expression plasmid encoding a fusion protein containing the natural RT-IN protease cleavage site (15 amino acids) positioned between the Vpr and integrase genes (VPR-PC-IN) produces a protein packaged into virions by means of Vpr, which is processed to yield active, authentic integrase.

Figure 11:
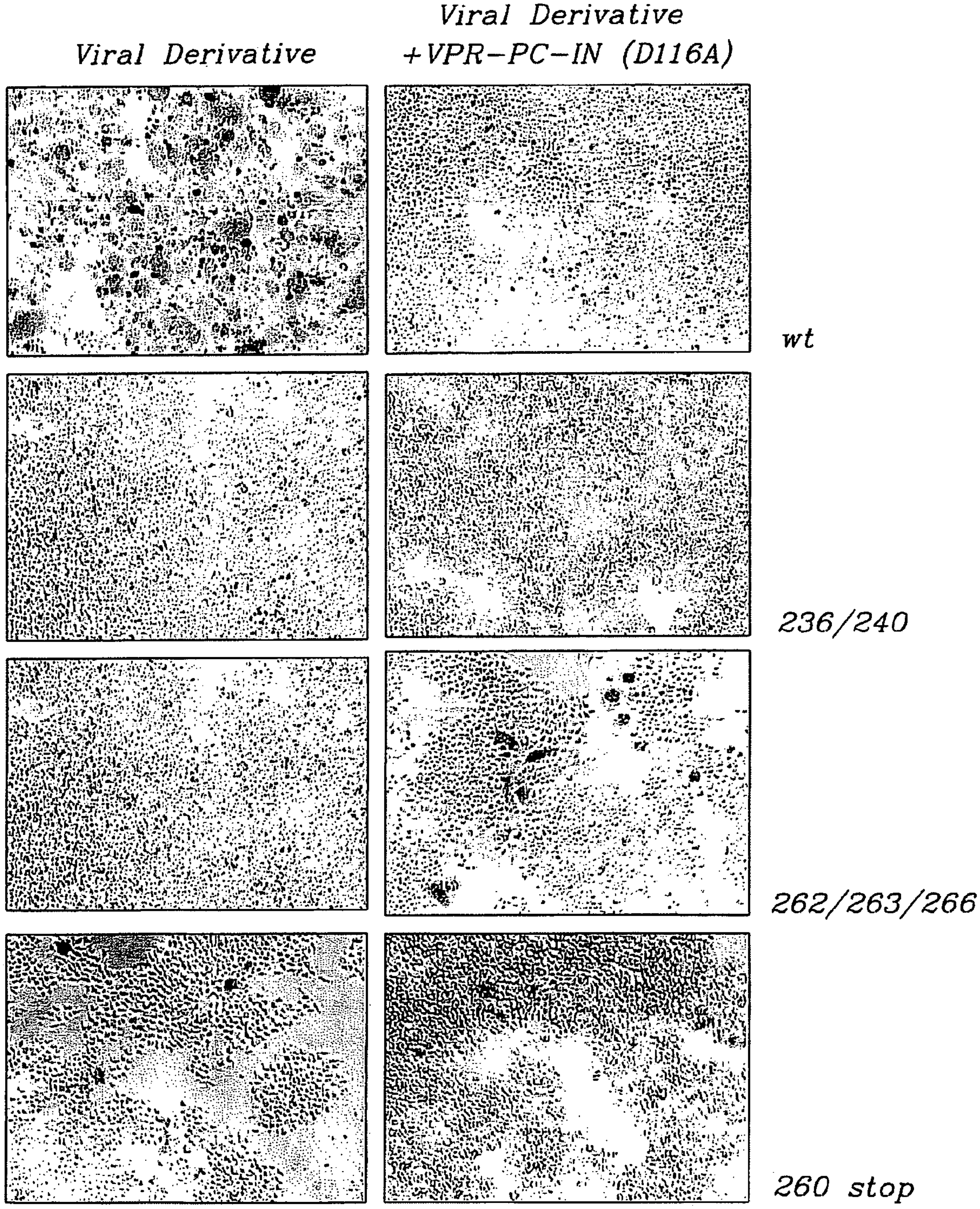
FIG. 11 shows that integrase NLS mutants are capable of providing catalytic activity though intravirion complementation R5 wild-type and mutant viral stocks were prepared by co-transfection of proviral DNA with either pcDNA3.1(+) (left) or pVPR-PC-IN (D116A) (right) p24-nonnalized stocks were used to infect P4-CCR5 (HeLa) cells in the presence of an inhibitory concentration of the protease inhibitor, Saquinavir to prevent viral propagation. Forty-eight hours later the cells were stained for β-galactosidase activity in situ.

It was then determined whether activities associated normally with HIV-1 integrase were restored by intravirion complementation between an NLS mutant and a mutant unable to perform the normal enzymatic functions associated with integrase. pVPR-PC-IN was modified by an aspartic acid-to-alanine substitution at position 116, which renders integrase catalytically inactive yet has no effect on nuclear transport of EGFP-integrase fusion proteins (see above). Productive infection of P4-CCR5 (HeLa) cells with hybrid virions was monitored over a single-cycle, and the efficiency of viral nuclear import and integration measured qualitatively by histochemical staining for β-galactosidase activity in situ. As shown in FIG. 11, IN NLS mutants and the catalytic site mutant D116A were able to functionally complement each other in trans. To corroborate these results, transduction of a trans-dominant marker gene, guanosine phosphotransferase (gpt), was used as a direct indicator of retroviral integration. The wild-type and mutant viral DNAs were modified to encode gpt and viral stocks were prepared in either the presence or absence of VPR-PC-IN (D116A) as above. Neither D116A nor the NLS mutants are capable of stable transduction of the gpt marker gene (data not shown). In contrast, intragenic complementation of the NLS mutants by the co-incorporation of D116A integrase into the virion restored integration to between 10-20% that of the wild-type virus (data not shown). Importantly, no complementation (integration) was detected when D116A was in homologous combination. Thus integrase NLS mutations do not abrogate enzymatic function in a global sense, but rather create specific defect(s) in the transportation of the viral genome into the host cell nucleus.

Example 7

Integrase NLS Mutant Inhibition of HIV Pathogenesis

Figure 12:
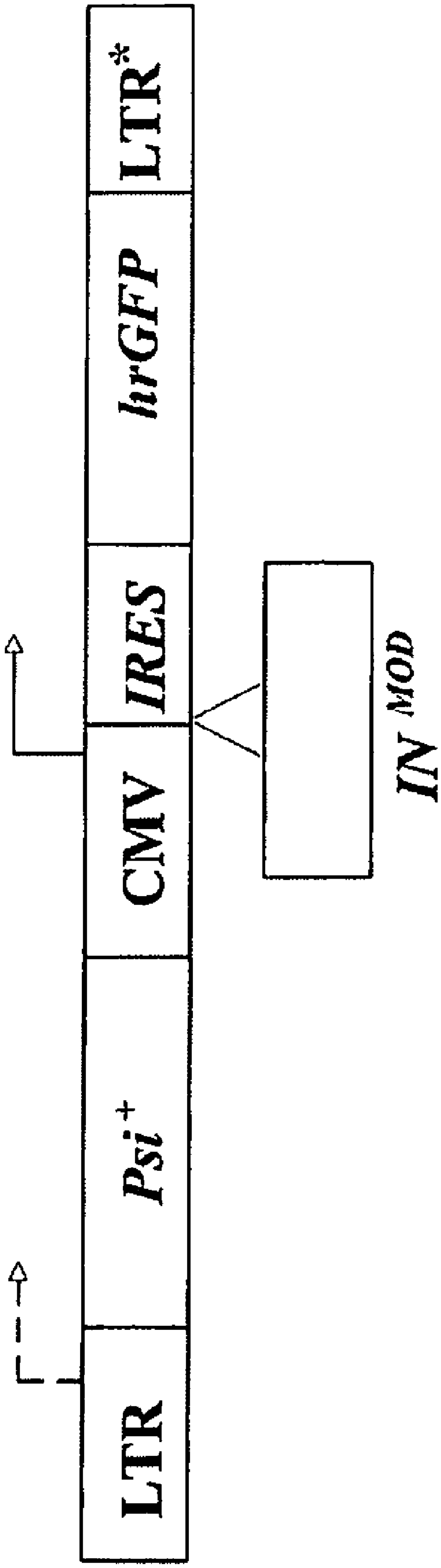
FIG. 12 depicts a murine retroviral vector expressing a bi-cistronic transcript containing a modified version of the HIV-1 integrase protein, an internal ribosome entry sequence (IRES) and a humanized version of the renilla green fluorescent protein (hrGFP). CMV is the cytomegalovirus promoter: enhancer. LTR* was constructed by deletion of the MLV promoter:enhancer in the 3'LTR but retention of the viral polyA addition signal. The 5' LTR is used to produce virions after DNA transfection of the proviral DNA clone After reverse transcription and integration the 5' LTR is inactivated by deletion of its enhancer and promoter elements and vector gene expression is driven by an internal CMV promoter: enhancer.

A murine retroviral vector was constructed that when stably incorporated in cells, creates lines that overexpress the integrase NLS (220-270). The murine retroviral vector expresses a bi-cistronic transcript containing a modified version of the HIV-1 integrase protein, an internal ribosome entry sequence (IRES) and a humanized version of the *renilla* green fluorescent protein (hrGFP) (FIG. 12). The 5' LTR produces virions following DNA transfection of cells with the proviral DNA clone. Following reverse transcription and integration, the 5' LTR is inactivated by deletion of its enhancer and promoter elements and vector gene expression is driven by the internal cytomegalovirus (CMV) promoter/enhancer. LTR* was constructed to be deleted for the MLV promoter/enhancer yet retaining the viral polyA addition signal.

Figure 13:
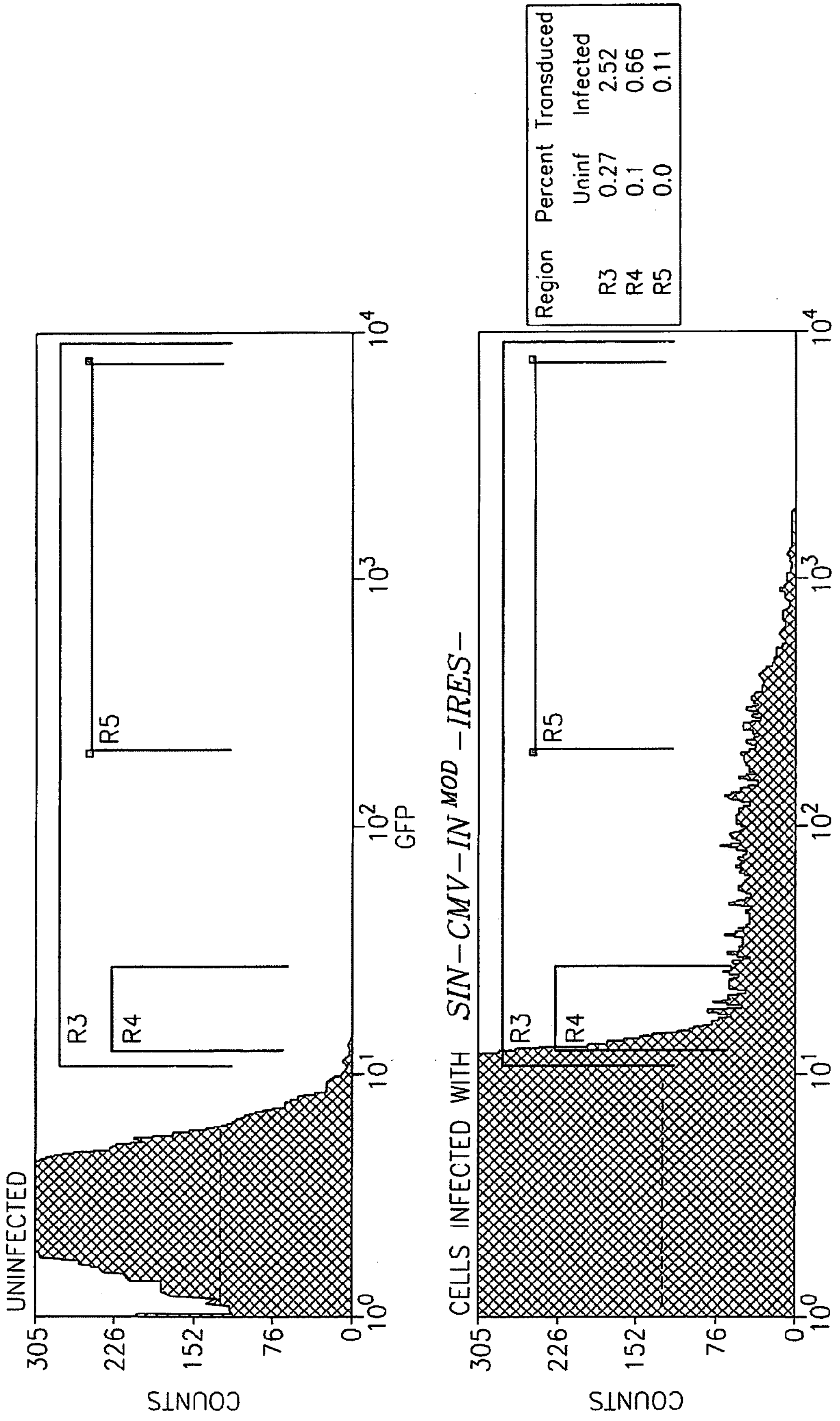
FIG. 13 depicts a FACS Analysis of SIN-CMV-INMOD-IRES-hrGFP Transduced Cells. Cells were infected with a retroviral vector expressing integrase and sorted for high-level green fluorescence. Cells were obtained for gated cells (R4 and R5).
Figures 14, 15:
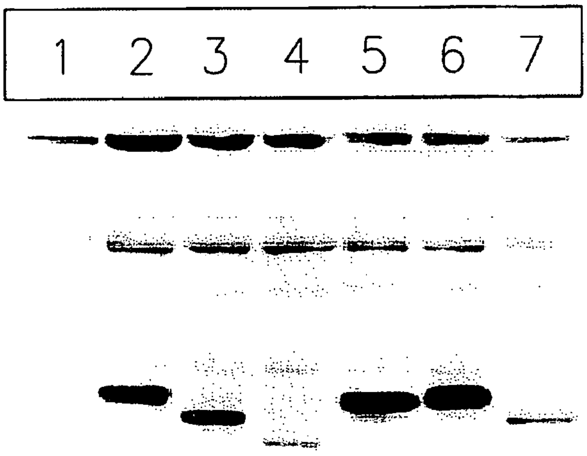
FIG. 14 shows the results of a Western Blot analysis of integrase expression in cells infected with derivatives-of SIN-CMV-INMOD-IRES-hrGFP and sorted for high-level hrGFP fluorescence. Lane 1, uninfected cells; Lane 2, wild-type integrase protein (1-288); Lane 3, integrase (22-288); Lane 4, integrase (50-288); Lane 5, integrase K136A/E138A (1-288); Lane 6, integrase D116A (1-288); Lane 7, integrase (1-260). Probed with a monoclonal antibody specific for integrase.
FIG. 15 demonstrates consensus PXXP Motifs in the human EED protein. PXXP exist within the context of a larger consensus sequence typical of intra-and/or inter- molecular SH3 domain interaction. As indicated, the human EED protein contains three PXXP motifs (set forth as SEQ ID NO:164, SEQ ID NO:165 and SEQ ID NO:166, respectively), two of which have flanking amino acid residues typical of known, functional PXXP motifs.

The retroviral vector in this case is self-inactivating (for ltr promoter/enhancer functions), and target gene expression was driven by an internal cmv promoter and monitored via a linked ires-hrgfp reporter protein together comprising a bicistronic mRNA. Cells expressing large amounts of the transduced target protein were therefore readily identified and purified using the fluorescent surrogate marker, hrGFP (FIG. 13). FACS Analysis of SIN-CMV-INMOD-IRES-hrGFP transduced cells demonstrated high-levels of green fluorescence, indicating good transduction efficiency. Cells transduced with derivatives of SIN-CMV-INMOD-IRES-hrGFP isolated via FACS sorted for high hrGFP fluorescence were then examined by western blot analysis for HIV-1 integrase expression (FIG. 14). Constructs comprising WT integrase and integrase derivatives were expressed in cells infected with respective SIN-CMV-INMOD-IRES-hrGFP constructs.

Transfected cells are then challenged with wild type HIV, and the ability of the expressed mutant integrase to "decoy" or sequester necessary cellular factors required for viral infection are determined by p24 assay, syncytia formation, and other methods for measuring HIV infection. Constructs comprising mutant integrase NLS, unable to mediate nuclear import, provide an advantage in inhibiting HIV pathogenesis.

Example 8

The Human EED-Polycomb Protein Comprises a PXXP Motif, which Coordinates Binding to SH3 Domains Human embryonic ectoderm development protein (EED) exists in three isofornis (a, b and truncated; Genbank accession numbers: NP_003788, NP_694536 and AAH47672, respectively). Review of all 3 isoforms demonstrated the existence of a conserved PXXP motif (FIG. 15). The PXXP motif exists within the context of a larger consensus sequence typical of intra- and/or inter- molecular SH3 domain interaction, with proline-enriched domains having been shown previously to exhibit SH3 binding activity The HIV integrase NLS comprises an SH3 domain. Mutation of the PXXP motif of EED abrogates binding to the NLS. Toward this end, the portion of the HIV-1 gene segment-coding for the IN NLS is cloned in frame with the DNA-binding Gal4 gene into a pGBKT7 (yeast) or pM (mammalian) vectors (Clontech). The sequence of the construct is verified by DNA sequencing, and the expression of recombinant fusion protein in yeast or mammalian cells is confirmed by gel electrophoresis and immunoblot analysis with anti-NLS antibody as described herein. Plasmids containing the wild-type and mutant EED reading frame are constructed by RT/PCR of total RNA from activated, human primary CD4+ lymphocytes using DNA primers specific for human EED and cloned in frame with the transcriptional activation domain of Ga14 (pACT, yeast expression, Clontech) or VP16 (pVP16, mammalian expression, Clontech), which produces a Ga14 activation domain AD-EED hybrid or a VP16-EED hybrid. Hybrids are constructed with 2 mutant forms of EED, the PXXP motif mutant P56A/P60A and the EED NLS mutant (K74A/K76A/K77A/K79A). The two-hybrid assays are then performed as described.

What is claimed is:

1. An isolated polynucleotide comprising a nucleic acid encoding a lentiviral nuclear localization signal derived from a fragment of an HIV-1 integrase consisting of the amino acid sequence corresponding to the formula:

$R_5(R_6)_2FRVYR_1R_3R_2R_8R_3NPLWR_3GPR_8KR_4R_5WR_3GEGA(R_4)_3R_6DR_6SR_6R_4KVR_4PR(R_3)_2R_8KIR_4R_3D$, wherein:

$R_1$=an aromatic amino acid;

$R_2$=an acidic amino acid;

$R_3$=a basic amino acid;

$R_4$=a branched chain amino acid;

$R_5$=a hydrophobic amino acid;

$R_6$=a polar amino acid;

$R_7$=a proline or serine amino acid residue;

$R_8$=a small amino acid residue selected from the group consisting of a glycine, an alanine, a cysteine and an asparagine amino acid residue.

* * * * *

SEQUENCE LISTING

```
<160> NUMBER OF SEQ ID NOS: 149

<210> SEQ ID NO 1
<211> LENGTH: 870
<212> TYPE: DNA
<213> ORGANISM: Artificial
<220> FEATURE:
<223> OTHER INFORMATION: Synthetic construct

<400> SEQUENCE: 1

atgttcctgg acggtatcga caaagctcag gacgagcacg aaaagtacca ttctaactgg     60

cgcgccatgg cctctgactt caatctcccg ccggttgttg ccaaggagat cgtggcttct    120

tgcgacaagt gccaattgaa gggtgaggct atgcatggtc aggtcgattg ctctcccggt    180

atctggcagc tggactgcac tcacctcgag ggtaaggtga ttctcgttgc tgtgcacgtg    240

gcttccggct acatcgaggc tgaggtcatc ccggctgaga ccggtcaaga gactgcttac    300

ttcctgctca agctggccgg ccgttggcca gttaagacta ttcacactga taacggttct    360

aactttactt ccgcaactgt gaaagctgca tgctggtggg ccggcattaa acaagagttc    420

ggaattccgt ataacccgca gtctcagggc gttgtcgagt ctatgaacaa ggagctcaaa    480

aagatcattg gtcaagtccg tgaccaagct gagcacctta agaccgctgt gcagatggct    540

gtttttattc ataacttcaa gcgtaagggt ggtatcggtg gttatagcgc tggtgagcgt    600

atcgtagaca tcatcgctac tgatatccag acaaaggagc tgcagaagca gatcactaag    660

atccagaact tccgtgtgta ctatcgggac tctaggaacc cgctctggaa gggtcctgct    720

aaactgctgt ggaagggaga gggtgctgtt gttatccagg acaactctga tatcaaggtg    780

gttccgcgtc gtaaggctaa aattatccgc gactacggca agcaaatggc tggagacgac    840

tgcgttgcta gccgtcaaga cgaagactaa                                     870


<210> SEQ ID NO 2
<211> LENGTH: 867
<212> TYPE: DNA
<213> ORGANISM: Human immunodeficiency virus type 1

<400> SEQUENCE: 2

tttttagatg gaatagataa ggcccaagat gaacatgaga aatatcacag taattggaga     60

gcaatggcta gtgattttaa cctgccacct gtagtagcaa aagaaatagt agccagctgt    120

gataaatgtc agctaaaagg agaagccatg catggacaag tagactgtag tccaggaata    180

tggcaactag attgtacaca tttagaagga aaagttatcc tggtagcagt tcatgtagcc    240

agtggatata tagaagcaga agttattcca gcagaaacag ggcaggaaac agcatatttt    300

cttttaaaat tagcaggaag atggccagta aaaacaatac atacagacaa tggcagcaat    360

ttcaccagtg ctacggttaa ggccgcctgt tggtgggcgg gaatcaagca ggaatttgga    420

attccctaca atccccaaag tcaaggagta gtagaatcta tgaataaaga attaaagaaa    480
```

-continued

```
attataggac aggtaagaga tcaggctgaa catcttaaga cagcagtaca aatggcagta    540

ttcatccaca attttaaaag aaaagggggg attgggggt acagtgcagg ggaaagaata    600

gtagacataa tagcaacaga catacaaact aaagaattac aaaaacaaat tacaaaaatt    660

caaaattttc gggtttatta cagggacagc agaaatccac tttggaaagg accagcaaag    720

ctcctctgga aaggtgaagg ggcagtagta atacaagata atagtgacat aaaagtagtg    780

ccaagaagaa aagcaaagat cattagggat tatggaaaac agatggcagg tgatgattgt    840

gtggcaagta gacaggatga ggattag                                        867
```

<210> SEQ ID NO 3
<211> LENGTH: 288
<212> TYPE: PRT
<213> ORGANISM: Human immunodeficiency virus type 1

<400> SEQUENCE: 3

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 4

-continued

<211> LENGTH: 30
<212> TYPE: DNA
<213> ORGANISM: Human immunodeficiency virus type 1

<400> SEQUENCE: 4
gcaatggcta gtgcttttaa cctgccacct 30

<210> SEQ ID NO 5
<211> LENGTH: 30
<212> TYPE: DNA
<213> ORGANISM: Human immunodeficiency virus type 1

<400> SEQUENCE: 5
atatggcaac tagcttgtac acatttagaa 30

<210> SEQ ID NO 6
<211> LENGTH: 29
<212> TYPE: DNA
<213> ORGANISM: Human immunodeficiency virus type 1

<400> SEQUENCE: 6
catggacaag tagcctgtag tccaggaat 29

<210> SEQ ID NO 7
<211> LENGTH: 30
<212> TYPE: DNA
<213> ORGANISM: Human immunodeficiency virus type 1

<400> SEQUENCE: 7
ctggtagcag ttgctgtagc cagtggatat 30

<210> SEQ ID NO 8
<211> LENGTH: 30
<212> TYPE: DNA
<213> ORGANISM: Human immunodeficiency virus type 1

<400> SEQUENCE: 8
acaatacata cagccaatgg cagcaatttc 30

<210> SEQ ID NO 9
<211> LENGTH: 30
<212> TYPE: DNA
<213> ORGANISM: Human immunodeficiency virus type 1

<400> SEQUENCE: 9
agtgctacgg ttgcggccgc ctgttggtgg 30

<210> SEQ ID NO 10
<211> LENGTH: 30
<212> TYPE: DNA
<213> ORGANISM: Human immunodeficiency virus type 1

<400> SEQUENCE: 10
tgggcgggaa tcgcgcagga atttggaatt 30

<210> SEQ ID NO 11
<211> LENGTH: 30
<212> TYPE: DNA
<213> ORGANISM: Human immunodeficiency virus type 1

<400> SEQUENCE: 11
caaggagtag tagcatctat gaataaagaa 30

-continued

<210> SEQ ID NO 12
<211> LENGTH: 30
<212> TYPE: DNA
<213> ORGANISM: Human immunodeficiency virus type 1

<400> SEQUENCE: 12
gaatctatga atgcagaatt aaagaaaatt 30

<210> SEQ ID NO 13
<211> LENGTH: 30
<212> TYPE: DNA
<213> ORGANISM: Human immunodeficiency virus type 1

<400> SEQUENCE: 13
aataaagaat tagcgaaaat tataggacag 30

<210> SEQ ID NO 14
<211> LENGTH: 30
<212> TYPE: DNA
<213> ORGANISM: Human immunodeficiency virus type 1

<400> SEQUENCE: 14
aaagaattaa aggcaattat aggacaggta 30

<210> SEQ ID NO 15
<211> LENGTH: 30
<212> TYPE: DNA
<213> ORGANISM: Human immunodeficiency virus type 1

<400> SEQUENCE: 15
attataggac aggcaagaga tcaggctgaa 30

<210> SEQ ID NO 16
<211> LENGTH: 30
<212> TYPE: DNA
<213> ORGANISM: Human immunodeficiency virus type 1

<400> SEQUENCE: 16
ataggacagg tagcagatca ggctgaacat 30

<210> SEQ ID NO 17
<211> LENGTH: 30
<212> TYPE: DNA
<213> ORGANISM: Human immunodeficiency virus type 1

<400> SEQUENCE: 17
gcagtattca tcgccaattt taaaagaaaa 30

<210> SEQ ID NO 18
<211> LENGTH: 30
<212> TYPE: DNA
<213> ORGANISM: Human immunodeficiency virus type 1

<400> SEQUENCE: 18
atccacaatt ttgcaagaaa aggggggatt 30

<210> SEQ ID NO 19
<211> LENGTH: 30
<212> TYPE: DNA
<213> ORGANISM: Human immunodeficiency virus type 1

<400> SEQUENCE: 19
atccacaatt ttcaaagaaa aggggggatt 30

-continued

<210> SEQ ID NO 20
<211> LENGTH: 30
<212> TYPE: DNA
<213> ORGANISM: Human immunodeficiency virus type 1

<400> SEQUENCE: 20
cacaatttta aagcaaaagg ggggattggg 30

<210> SEQ ID NO 21
<211> LENGTH: 30
<212> TYPE: DNA
<213> ORGANISM: Human immunodeficiency virus type 1

<400> SEQUENCE: 21
gacatacaaa ctgcagaatt acaaaaacaa 30

<210> SEQ ID NO 22
<211> LENGTH: 30
<212> TYPE: DNA
<213> ORGANISM: Human immunodeficiency virus type 1

<400> SEQUENCE: 22
atacaaacta aagcattaca aaaacaaatt 30

<210> SEQ ID NO 23
<211> LENGTH: 30
<212> TYPE: DNA
<213> ORGANISM: Human immunodeficiency virus type 1

<400> SEQUENCE: 23
aaagaattac aagcacaaat tacaaaaatt 30

<210> SEQ ID NO 24
<211> LENGTH: 30
<212> TYPE: DNA
<213> ORGANISM: Human immunodeficiency virus type 1

<400> SEQUENCE: 24
aaacaaatta cagcaattca aaattttcgg 30

<210> SEQ ID NO 25
<211> LENGTH: 30
<212> TYPE: DNA
<213> ORGANISM: Human immunodeficiency virus type 1

<400> SEQUENCE: 25
attcaaaatt ttgcggttta ttacagggac 30

<210> SEQ ID NO 26
<211> LENGTH: 30
<212> TYPE: DNA
<213> ORGANISM: Human immunodeficiency virus type 1

<400> SEQUENCE: 26
cgggtttatt acgcggacag cagaaatcca 30

<210> SEQ ID NO 27
<211> LENGTH: 30
<212> TYPE: DNA
<213> ORGANISM: Human immunodeficiency virus type 1

<400> SEQUENCE: 27
aagctcctct gggcaggtga aggggcagta 30

-continued

<210> SEQ ID NO 28
<211> LENGTH: 30
<212> TYPE: DNA
<213> ORGANISM: Human immunodeficiency virus type 1

<400> SEQUENCE: 28
aatccacttt gggcaggacc agcaaagctc 30

<210> SEQ ID NO 29
<211> LENGTH: 30
<212> TYPE: DNA
<213> ORGANISM: Human immunodeficiency virus type 1

<400> SEQUENCE: 29
aaaggaccag cagcgctcct ctggaaaggt 30

<210> SEQ ID NO 30
<211> LENGTH: 30
<212> TYPE: DNA
<213> ORGANISM: Human immunodeficiency virus type 1

<400> SEQUENCE: 30
aaagtagtgc cagcaagaaa agcaaagatc 30

<210> SEQ ID NO 31
<211> LENGTH: 30
<212> TYPE: DNA
<213> ORGANISM: Human immunodeficiency virus type 1

<400> SEQUENCE: 31
gtagtgccaa gagcaaaagc aaagatcatt 30

<210> SEQ ID NO 32
<211> LENGTH: 30
<212> TYPE: DNA
<213> ORGANISM: Human immunodeficiency virus type 1

<400> SEQUENCE: 32
gtgccaagaa gagcagcaaa gatcattagg 30

<210> SEQ ID NO 33
<211> LENGTH: 30
<212> TYPE: DNA
<213> ORGANISM: Human immunodeficiency virus type 1

<400> SEQUENCE: 33
agaagaaaag cagcgatcat tagggattat 30

<210> SEQ ID NO 34
<211> LENGTH: 30
<212> TYPE: DNA
<213> ORGANISM: Human immunodeficiency virus type 1

<400> SEQUENCE: 34
gcaaagatca ttgcggatta tggaaaacag 30

<210> SEQ ID NO 35
<211> LENGTH: 30
<212> TYPE: DNA
<213> ORGANISM: Human immunodeficiency virus type 1

<400> SEQUENCE: 35

-continued cctgtagtag cagcagcaat agtagccagc 30

<210> SEQ ID NO 36
<211> LENGTH: 30
<212> TYPE: DNA
<213> ORGANISM: Human immunodeficiency virus type 1

<400> SEQUENCE: 36
gtagccagct gtgctgcatg tcagctaaaa 30

<210> SEQ ID NO 37
<211> LENGTH: 30
<212> TYPE: DNA
<213> ORGANISM: Human immunodeficiency virus type 1

<400> SEQUENCE: 37
aaatgtcagc tagcaggagc agccatgcat 30

<210> SEQ ID NO 38
<211> LENGTH: 30
<212> TYPE: DNA
<213> ORGANISM: Human immunodeficiency virus type 1

<400> SEQUENCE: 38
ctagattgta cagctttagc aggaaaagtt 30

<210> SEQ ID NO 39
<211> LENGTH: 30
<212> TYPE: DNA
<213> ORGANISM: Human immunodeficiency virus type 1

<400> SEQUENCE: 39
tgtacacatt tagcaggagc agttatcctg 30

<210> SEQ ID NO 40
<211> LENGTH: 30
<212> TYPE: DNA
<213> ORGANISM: Human immunodeficiency virus type 1

<400> SEQUENCE: 40
agtggatata tagcagcagc agttattcca 30

<210> SEQ ID NO 41
<211> LENGTH: 30
<212> TYPE: DNA
<213> ORGANISM: Human immunodeficiency virus type 1

<400> SEQUENCE: 41
tattttcttt tagcattagc aggagcatgg 30

<210> SEQ ID NO 42
<211> LENGTH: 30
<212> TYPE: DNA
<213> ORGANISM: Human immunodeficiency virus type 1

<400> SEQUENCE: 42
agatggccag tagcaacaat agctacagac 30

<210> SEQ ID NO 43
<211> LENGTH: 30
<212> TYPE: DNA
<213> ORGANISM: Human immunodeficiency virus type 1

<400> SEQUENCE: 43

-continued agatggccag tagcaacaat agctacagac 30

<210> SEQ ID NO 44
<211> LENGTH: 30
<212> TYPE: DNA
<213> ORGANISM: Human immunodeficiency virus type 1

<400> SEQUENCE: 44
gaatctatga atgcagaatt agcgaaaatt 30

<210> SEQ ID NO 45
<211> LENGTH: 30
<212> TYPE: DNA
<213> ORGANISM: Human immunodeficiency virus type 1

<400> SEQUENCE: 45
gaatctatga atgcagaatt agcggcaatt 30

<210> SEQ ID NO 46
<211> LENGTH: 30
<212> TYPE: DNA
<213> ORGANISM: Human immunodeficiency virus type 1

<400> SEQUENCE: 46
gaatctatga atgcagaatt aaaggcaatt 30

<210> SEQ ID NO 47
<211> LENGTH: 30
<212> TYPE: DNA
<213> ORGANISM: Human immunodeficiency virus type 1

<400> SEQUENCE: 47
aataaagaat tagcggcaat tataggacag 30

<210> SEQ ID NO 48
<211> LENGTH: 30
<212> TYPE: DNA
<213> ORGANISM: Human immunodeficiency virus type 1

<400> SEQUENCE: 48
attataggac aggcagcaga tcaggctgaa 30

<210> SEQ ID NO 49
<211> LENGTH: 30
<212> TYPE: DNA
<213> ORGANISM: Human immunodeficiency virus type 1

<400> SEQUENCE: 49
ataggacagg tagcagctca ggctgaacat 30

<210> SEQ ID NO 50
<211> LENGTH: 30
<212> TYPE: DNA
<213> ORGANISM: Human immunodeficiency virus type 1

<400> SEQUENCE: 50
agagatcagg ctgcagctct taagacagca 30

<210> SEQ ID NO 51
<211> LENGTH: 30
<212> TYPE: DNA
<213> ORGANISM: Human immunodeficiency virus type 1

-continued

<400> SEQUENCE: 51
gatcaggctg aagctcttgc gacagcagta 30

<210> SEQ ID NO 52
<211> LENGTH: 30
<212> TYPE: DNA
<213> ORGANISM: Human immunodeficiency virus type 1

<400> SEQUENCE: 52
atccacaatt ttgcagcaaa aggggggatt 30

<210> SEQ ID NO 53
<211> LENGTH: 30
<212> TYPE: DNA
<213> ORGANISM: Human immunodeficiency virus type 1

<400> SEQUENCE: 53
atccacaatt ttgcaagagc aggggggatt 30

<210> SEQ ID NO 54
<211> LENGTH: 30
<212> TYPE: DNA
<213> ORGANISM: Human immunodeficiency virus type 1

<400> SEQUENCE: 54
atccacaatt ttgcagcagc aggggggatt 30

<210> SEQ ID NO 55
<211> LENGTH: 30
<212> TYPE: DNA
<213> ORGANISM: Human immunodeficiency virus type 1

<400> SEQUENCE: 55
atccacaatt ttaaagcagc aggggggatt 30

<210> SEQ ID NO 56
<211> LENGTH: 30
<212> TYPE: DNA
<213> ORGANISM: Human immunodeficiency virus type 1

<400> SEQUENCE: 56
tacagtgcag gggcagcaat agtagacata 30

<210> SEQ ID NO 57
<211> LENGTH: 30
<212> TYPE: DNA
<213> ORGANISM: Human immunodeficiency virus type 1

<400> SEQUENCE: 57
agtgcagggg aagcaatagt agccataata 30

<210> SEQ ID NO 58
<211> LENGTH: 30
<212> TYPE: DNA
<213> ORGANISM: Human immunodeficiency virus type 1

<400> SEQUENCE: 58
actaaagaat tactaaaact aattacaaaa 30

<210> SEQ ID NO 59
<211> LENGTH: 30
<212> TYPE: DNA
<213> ORGANISM: Human immunodeficiency virus type 1

-continued

<400> SEQUENCE: 59
attcaaaatt ttgcggttta ttacgcggac 30

<210> SEQ ID NO 60
<211> LENGTH: 30
<212> TYPE: DNA
<213> ORGANISM: Human immunodeficiency virus type 1

<400> SEQUENCE: 60
gtttattaca gggccagcgc aaatccactt 30

<210> SEQ ID NO 61
<211> LENGTH: 30
<212> TYPE: DNA
<213> ORGANISM: Human immunodeficiency virus type 1

<400> SEQUENCE: 61
aatccacttt gggcaggacc agcagcgctc 30

<210> SEQ ID NO 62
<211> LENGTH: 30
<212> TYPE: DNA
<213> ORGANISM: Human immunodeficiency virus type 1

<400> SEQUENCE: 62
gtagtaatac aagctaatag tgccataaaa 30

<210> SEQ ID NO 63
<211> LENGTH: 30
<212> TYPE: DNA
<213> ORGANISM: Human immunodeficiency virus type 1

<400> SEQUENCE: 63
caagataata gtgccatagc agtagtgcca 30

<210> SEQ ID NO 64
<211> LENGTH: 30
<212> TYPE: DNA
<213> ORGANISM: Human immunodeficiency virus type 1

<400> SEQUENCE: 64
aaagtagtgc cagcagcaaa agcagcgatc 30

<210> SEQ ID NO 65
<211> LENGTH: 30
<212> TYPE: DNA
<213> ORGANISM: Human immunodeficiency virus type 1

<400> SEQUENCE: 65
gtagtgccaa gagcagcagc aaagatcatt 30

<210> SEQ ID NO 66
<211> LENGTH: 29
<212> TYPE: DNA
<213> ORGANISM: Human immunodeficiency virus type 1

<400> SEQUENCE: 66
gcaaagatca ttgcggctta tggaaaaca 29

<210> SEQ ID NO 67
<211> LENGTH: 288
<212> TYPE: PRT

-continued

<213> ORGANISM: Human immunodeficiency virus type 1

<400> SEQUENCE: 67

Phe Leu Asp Gly Ile Asp Lys Ala Gln Asp Glu His Glu Lys Tyr His
1               5                   10                  15

Ser Asn Trp Arg Ala Met Ala Ser Ala Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285

<210> SEQ ID NO 68
<211> LENGTH: 288
<212> TYPE: PRT
<213> ORGANISM: Human immunodeficiency virus type 1

<400> SEQUENCE: 68

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Ala
    50                  55                  60

Cys Thr His Leu Glu Gly Lys Val Ile Leu Val Ala Val His Val Ala

-continued

```
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 69
<211> LENGTH: 288
<212> TYPE: PRT
<213> ORGANISM: Human immunodeficiency virus type 1

<400> SEQUENCE: 69

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Ala Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160
```

-continued

```
Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 70
<211> LENGTH: 288
<212> TYPE: PRT
<213> ORGANISM: Human immunodeficiency virus type 1

<400> SEQUENCE: 70

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val Ala Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255
```

-continued

```
Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 71
<211> LENGTH: 288
<212> TYPE: PRT
<213> ORGANISM: Human immunodeficiency virus type 1

<400> SEQUENCE: 71

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Ala Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 72
<211> LENGTH: 288
<212> TYPE: PRT
<213> ORGANISM: Human immunodeficiency virus type 1

<400> SEQUENCE: 72

```
Phe Leu Asp Gly Ile Asp Lys Ala Gln Asp Glu His Glu Lys Tyr His
1               5                   10                  15
```

-continued

```
Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Ala Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 73
<211> LENGTH: 288
<212> TYPE: PRT
<213> ORGANISM: Human immunodeficiency virus type 1

<400> SEQUENCE: 73

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
```

-continued

```
            100                 105                 110

Ile His Thr Asp Asn Gly Ser Asn Phe Thr Ser Ala Thr Val Lys Ala
        115                 120                 125

Ala Cys Trp Trp Ala Gly Ile Ala Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 74
<211> LENGTH: 288
<212> TYPE: PRT
<213> ORGANISM: Human immunodeficiency virus type 1

<400> SEQUENCE: 74

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Ala Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190
```

-continued

```
Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 75
<211> LENGTH: 288
<212> TYPE: PRT
<213> ORGANISM: Human immunodeficiency virus type 1

<400> SEQUENCE: 75

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Ala Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

-continued

<210> SEQ ID NO 76
<211> LENGTH: 288
<212> TYPE: PRT
<213> ORGANISM: Human immunodeficiency virus type 1

<400> SEQUENCE: 76

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Ala Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 77
<211> LENGTH: 288
<212> TYPE: PRT
<213> ORGANISM: Human immunodeficiency virus type 1

<400> SEQUENCE: 77

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45
```

-continued

```
Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Ala
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 78
<211> LENGTH: 288
<212> TYPE: PRT
<213> ORGANISM: Human immunodeficiency virus type 1

<400> SEQUENCE: 78

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
```

-continued

```
    130                 135                 140

Pro Gln Ser Gln Gly Val Val Glu Ser Met Asn Lys Glu Leu Lys Lys
145                 150                 155                 160

Ile Ile Gly Gln Ala Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 79
<211> LENGTH: 288
<212> TYPE: PRT
<213> ORGANISM: Human immunodeficiency virus type 1

<400> SEQUENCE: 79

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Ala Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220
```

-continued

```
Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 80
<211> LENGTH: 288
<212> TYPE: PRT
<213> ORGANISM: Human immunodeficiency virus type 1

<400> SEQUENCE: 80

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile Ala Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 81
<211> LENGTH: 288
<212> TYPE: PRT
<213> ORGANISM: Human immunodeficiency virus type 1
```

-continued

<400> SEQUENCE: 81

Phe Leu Asp Gly Ile Asp Lys Ala Gln Asp Glu His Glu Lys Tyr His
1 5 10 15

Ser Asn Trp Arg Ala Met Ala Ser Asp Phe Asn Leu Pro Pro Val Val
20 25 30

Ala Lys Glu Ile Val Ala Ser Cys Asp Lys Cys Gln Leu Lys Gly Glu
35 40 45

Ala Met His Gly Gln Val Asp Cys Ser Pro Gly Ile Trp Gln Leu Asp
50 55 60

Cys Thr His Leu Glu Gly Lys Val Ile Leu Val Ala Val His Val Ala
65 70 75 80

Ser Gly Tyr Ile Glu Ala Glu Val Ile Pro Ala Glu Thr Gly Gln Glu
85 90 95

Thr Ala Tyr Phe Leu Leu Lys Leu Ala Gly Arg Trp Pro Val Lys Thr
100 105 110

Ile His Thr Asp Asn Gly Ser Asn Phe Thr Ser Ala Thr Val Lys Ala
115 120 125

Ala Cys Trp Trp Ala Gly Ile Lys Gln Glu Phe Gly Ile Pro Tyr Asn
130 135 140

Pro Gln Ser Gln Gly Val Val Glu Ser Met Asn Lys Glu Leu Lys Lys
145 150 155 160

Ile Ile Gly Gln Val Arg Asp Gln Ala Glu His Leu Lys Thr Ala Val
165 170 175

Gln Met Ala Val Phe Ile His Asn Phe Ala Arg Lys Gly Gly Ile Gly
180 185 190

Gly Tyr Ser Ala Gly Glu Arg Ile Val Asp Ile Ile Ala Thr Asp Ile
195 200 205

Gln Thr Lys Glu Leu Gln Lys Gln Ile Thr Lys Ile Gln Asn Phe Arg
210 215 220

Val Tyr Tyr Arg Asp Ser Arg Asn Pro Leu Trp Lys Gly Pro Ala Lys
225 230 235 240

Leu Leu Trp Lys Gly Glu Gly Ala Val Val Ile Gln Asp Asn Ser Asp
245 250 255

Ile Lys Val Val Pro Arg Arg Lys Ala Lys Ile Ile Arg Asp Tyr Gly
260 265 270

Lys Gln Met Ala Gly Asp Asp Cys Val Ala Ser Arg Gln Asp Glu Asp
275 280 285

<210> SEQ ID NO 82
<211> LENGTH: 288
<212> TYPE: PRT
<213> ORGANISM: Human immunodeficiency virus type 1

<400> SEQUENCE: 82

Phe Leu Asp Gly Ile Asp Lys Ala Gln Asp Glu His Glu Lys Tyr His
1 5 10 15

Ser Asn Trp Arg Ala Met Ala Ser Asp Phe Asn Leu Pro Pro Val Val
20 25 30

Ala Lys Glu Ile Val Ala Ser Cys Asp Lys Cys Gln Leu Lys Gly Glu
35 40 45

Ala Met His Gly Gln Val Asp Cys Ser Pro Gly Ile Trp Gln Leu Asp
50 55 60

Cys Thr His Leu Glu Gly Lys Val Ile Leu Val Ala Val His Val Ala
65 70 75 80

-continued

```
Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Gln Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 83
<211> LENGTH: 288
<212> TYPE: PRT
<213> ORGANISM: Human immunodeficiency virus type 1

<400> SEQUENCE: 83

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
```

-continued

```
                165                 170                 175

Gln Met Ala Val Phe Ile His Asn Phe Lys Ala Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 84
<211> LENGTH: 288
<212> TYPE: PRT
<213> ORGANISM: Human immunodeficiency virus type 1

<400> SEQUENCE: 84

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Ala Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255
```

-continued

Ile Lys Val Val Pro Arg Arg Lys Ala Lys Ile Ile Arg Asp Tyr Gly
260 265 270

Lys Gln Met Ala Gly Asp Asp Cys Val Ala Ser Arg Gln Asp Glu Asp
275 280 285

<210> SEQ ID NO 85
<211> LENGTH: 288
<212> TYPE: PRT
<213> ORGANISM: Human immunodeficiency virus type 1

<400> SEQUENCE: 85

Phe Leu Asp Gly Ile Asp Lys Ala Gln Asp Glu His Glu Lys Tyr His
1 5 10 15

Ser Asn Trp Arg Ala Met Ala Ser Asp Phe Asn Leu Pro Pro Val Val
20 25 30

Ala Lys Glu Ile Val Ala Ser Cys Asp Lys Cys Gln Leu Lys Gly Glu
35 40 45

Ala Met His Gly Gln Val Asp Cys Ser Pro Gly Ile Trp Gln Leu Asp
50 55 60

Cys Thr His Leu Glu Gly Lys Val Ile Leu Val Ala Val His Val Ala
65 70 75 80

Ser Gly Tyr Ile Glu Ala Glu Val Ile Pro Ala Glu Thr Gly Gln Glu
85 90 95

Thr Ala Tyr Phe Leu Leu Lys Leu Ala Gly Arg Trp Pro Val Lys Thr
100 105 110

Ile His Thr Asp Asn Gly Ser Asn Phe Thr Ser Ala Thr Val Lys Ala
115 120 125

Ala Cys Trp Trp Ala Gly Ile Lys Gln Glu Phe Gly Ile Pro Tyr Asn
130 135 140

Pro Gln Ser Gln Gly Val Val Glu Ser Met Asn Lys Glu Leu Lys Lys
145 150 155 160

Ile Ile Gly Gln Val Arg Asp Gln Ala Glu His Leu Lys Thr Ala Val
165 170 175

Gln Met Ala Val Phe Ile His Asn Phe Lys Arg Lys Gly Gly Ile Gly
180 185 190

Gly Tyr Ser Ala Gly Glu Arg Ile Val Asp Ile Ile Ala Thr Asp Ile
195 200 205

Gln Thr Lys Ala Leu Gln Lys Gln Ile Thr Lys Ile Gln Asn Phe Arg
210 215 220

Val Tyr Tyr Arg Asp Ser Arg Asn Pro Leu Trp Lys Gly Pro Ala Lys
225 230 235 240

Leu Leu Trp Lys Gly Glu Gly Ala Val Val Ile Gln Asp Asn Ser Asp
245 250 255

Ile Lys Val Val Pro Arg Arg Lys Ala Lys Ile Ile Arg Asp Tyr Gly
260 265 270

Lys Gln Met Ala Gly Asp Asp Cys Val Ala Ser Arg Gln Asp Glu Asp
275 280 285

<210> SEQ ID NO 86
<211> LENGTH: 288
<212> TYPE: PRT
<213> ORGANISM: Human immunodeficiency virus type 1

<400> SEQUENCE: 86

Phe Leu Asp Gly Ile Asp Lys Ala Gln Asp Glu His Glu Lys Tyr His
1 5 10 15

-continued

```
Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Ala Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 87
<211> LENGTH: 288
<212> TYPE: PRT
<213> ORGANISM: Human immunodeficiency virus type 1

<400> SEQUENCE: 87

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110
```

-continued

```
Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Ala Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 88
<211> LENGTH: 288
<212> TYPE: PRT
<213> ORGANISM: Human immunodeficiency virus type 1

<400> SEQUENCE: 88

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
```

-continued

```
        195                 200                 205

Gln Thr Lys Glu Leu Gln Lys Gln Ile Thr Lys Ile Gln Asn Phe Ala
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 89
<211> LENGTH: 288
<212> TYPE: PRT
<213> ORGANISM: Human immunodeficiency virus type 1

<400> SEQUENCE: 89

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Ala Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

-continued

<210> SEQ ID NO 90
<211> LENGTH: 288
<212> TYPE: PRT
<213> ORGANISM: Human immunodeficiency virus type 1

<400> SEQUENCE: 90

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Ala Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 91
<211> LENGTH: 288
<212> TYPE: PRT
<213> ORGANISM: Human immunodeficiency virus type 1

<400> SEQUENCE: 91

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45
```

-continued

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Ala Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285

<210> SEQ ID NO 92
<211> LENGTH: 288
<212> TYPE: PRT
<213> ORGANISM: Human immunodeficiency virus type 1

<400> SEQUENCE: 92

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

-continued

Pro Gln Ser Gln Gly Val Val Glu Ser Met Asn Lys Glu Leu Lys Lys
145 150 155 160

Ile Ile Gly Gln Val Arg Asp Gln Ala Glu His Leu Lys Thr Ala Val
165 170 175

Gln Met Ala Val Phe Ile His Asn Phe Lys Arg Lys Gly Gly Ile Gly
180 185 190

Gly Tyr Ser Ala Gly Glu Arg Ile Val Asp Ile Ile Ala Thr Asp Ile
195 200 205

Gln Thr Lys Glu Leu Gln Lys Gln Ile Thr Lys Ile Gln Asn Phe Arg
210 215 220

Val Tyr Tyr Arg Asp Ser Arg Asn Pro Leu Trp Lys Gly Pro Ala Ala
225 230 235 240

Leu Leu Trp Lys Gly Glu Gly Ala Val Val Ile Gln Asp Asn Ser Asp
245 250 255

Ile Lys Val Val Pro Arg Arg Lys Ala Lys Ile Ile Arg Asp Tyr Gly
260 265 270

Lys Gln Met Ala Gly Asp Asp Cys Val Ala Ser Arg Gln Asp Glu Asp
275 280 285

<210> SEQ ID NO 93
<211> LENGTH: 288
<212> TYPE: PRT
<213> ORGANISM: Human immunodeficiency virus type 1

<400> SEQUENCE: 93

Phe Leu Asp Gly Ile Asp Lys Ala Gln Asp Glu His Glu Lys Tyr His
1 5 10 15

Ser Asn Trp Arg Ala Met Ala Ser Asp Phe Asn Leu Pro Pro Val Val
20 25 30

Ala Lys Glu Ile Val Ala Ser Cys Asp Lys Cys Gln Leu Lys Gly Glu
35 40 45

Ala Met His Gly Gln Val Asp Cys Ser Pro Gly Ile Trp Gln Leu Asp
50 55 60

Cys Thr His Leu Glu Gly Lys Val Ile Leu Val Ala Val His Val Ala
65 70 75 80

Ser Gly Tyr Ile Glu Ala Glu Val Ile Pro Ala Glu Thr Gly Gln Glu
85 90 95

Thr Ala Tyr Phe Leu Leu Lys Leu Ala Gly Arg Trp Pro Val Lys Thr
100 105 110

Ile His Thr Asp Asn Gly Ser Asn Phe Thr Ser Ala Thr Val Lys Ala
115 120 125

Ala Cys Trp Trp Ala Gly Ile Lys Gln Glu Phe Gly Ile Pro Tyr Asn
130 135 140

Pro Gln Ser Gln Gly Val Val Glu Ser Met Asn Lys Glu Leu Lys Lys
145 150 155 160

Ile Ile Gly Gln Val Arg Asp Gln Ala Glu His Leu Lys Thr Ala Val
165 170 175

Gln Met Ala Val Phe Ile His Asn Phe Lys Arg Lys Gly Gly Ile Gly
180 185 190

Gly Tyr Ser Ala Gly Glu Arg Ile Val Asp Ile Ile Ala Thr Asp Ile
195 200 205

Gln Thr Lys Glu Leu Gln Lys Gln Ile Thr Lys Ile Gln Asn Phe Arg
210 215 220

Val Tyr Tyr Arg Asp Ser Arg Asn Pro Leu Trp Lys Gly Pro Ala Lys

-continued

```
225                 230                 235                 240

Leu Leu Trp Lys Gly Glu Gly Ala Val Val Ile Gln Asp Asn Ser Asp
                245                 250                 255

Ile Lys Val Val Pro Ala Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 94
<211> LENGTH: 288
<212> TYPE: PRT
<213> ORGANISM: Human immunodeficiency virus type 1

<400> SEQUENCE: 94

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Ala Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 95
<211> LENGTH: 288
<212> TYPE: PRT
<213> ORGANISM: Human immunodeficiency virus type 1
```

-continued

<400> SEQUENCE: 95

Phe Leu Asp Gly Ile Asp Lys Ala Gln Asp Glu His Glu Lys Tyr His
1 5 10 15

Ser Asn Trp Arg Ala Met Ala Ser Asp Phe Asn Leu Pro Pro Val Val
20 25 30

Ala Lys Glu Ile Val Ala Ser Cys Asp Lys Cys Gln Leu Lys Gly Glu
35 40 45

Ala Met His Gly Gln Val Asp Cys Ser Pro Gly Ile Trp Gln Leu Asp
50 55 60

Cys Thr His Leu Glu Gly Lys Val Ile Leu Val Ala Val His Val Ala
65 70 75 80

Ser Gly Tyr Ile Glu Ala Glu Val Ile Pro Ala Glu Thr Gly Gln Glu
85 90 95

Thr Ala Tyr Phe Leu Leu Lys Leu Ala Gly Arg Trp Pro Val Lys Thr
100 105 110

Ile His Thr Asp Asn Gly Ser Asn Phe Thr Ser Ala Thr Val Lys Ala
115 120 125

Ala Cys Trp Trp Ala Gly Ile Lys Gln Glu Phe Gly Ile Pro Tyr Asn
130 135 140

Pro Gln Ser Gln Gly Val Val Glu Ser Met Asn Lys Glu Leu Lys Lys
145 150 155 160

Ile Ile Gly Gln Val Arg Asp Gln Ala Glu His Leu Lys Thr Ala Val
165 170 175

Gln Met Ala Val Phe Ile His Asn Phe Lys Arg Lys Gly Gly Ile Gly
180 185 190

Gly Tyr Ser Ala Gly Glu Arg Ile Val Asp Ile Ile Ala Thr Asp Ile
195 200 205

Gln Thr Lys Glu Leu Gln Lys Gln Ile Thr Lys Ile Gln Asn Phe Arg
210 215 220

Val Tyr Tyr Arg Asp Ser Arg Asn Pro Leu Trp Lys Gly Pro Ala Lys
225 230 235 240

Leu Leu Trp Lys Gly Glu Gly Ala Val Val Ile Gln Asp Asn Ser Asp
245 250 255

Ile Lys Val Val Pro Arg Arg Ala Ala Lys Ile Ile Arg Asp Tyr Gly
260 265 270

Lys Gln Met Ala Gly Asp Asp Cys Val Ala Ser Arg Gln Asp Glu Asp
275 280 285

<210> SEQ ID NO 96
<211> LENGTH: 288
<212> TYPE: PRT
<213> ORGANISM: Human immunodeficiency virus type 1

<400> SEQUENCE: 96

Phe Leu Asp Gly Ile Asp Lys Ala Gln Asp Glu His Glu Lys Tyr His
1 5 10 15

Ser Asn Trp Arg Ala Met Ala Ser Asp Phe Asn Leu Pro Pro Val Val
20 25 30

Ala Lys Glu Ile Val Ala Ser Cys Asp Lys Cys Gln Leu Lys Gly Glu
35 40 45

Ala Met His Gly Gln Val Asp Cys Ser Pro Gly Ile Trp Gln Leu Asp
50 55 60

Cys Thr His Leu Glu Gly Lys Val Ile Leu Val Ala Val His Val Ala
65 70 75 80

-continued

```
Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Ala Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 97
<211> LENGTH: 288
<212> TYPE: PRT
<213> ORGANISM: Human immunodeficiency virus type 1

<400> SEQUENCE: 97

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175
```

-continued

Gln Met Ala Val Phe Ile His Asn Phe Lys Arg Lys Gly Gly Ile Gly
180 185 190

Gly Tyr Ser Ala Gly Glu Arg Ile Val Asp Ile Ile Ala Thr Asp Ile
195 200 205

Gln Thr Lys Glu Leu Gln Lys Gln Ile Thr Lys Ile Gln Asn Phe Arg
210 215 220

Val Tyr Tyr Arg Asp Ser Arg Asn Pro Leu Trp Lys Gly Pro Ala Lys
225 230 235 240

Leu Leu Trp Lys Gly Glu Gly Ala Val Val Ile Gln Asp Asn Ser Asp
245 250 255

Ile Lys Val Val Pro Arg Arg Lys Ala Lys Ile Ile Ala Asp Tyr Gly
260 265 270

Lys Gln Met Ala Gly Asp Asp Cys Val Ala Ser Arg Gln Asp Glu Asp
275 280 285

<210> SEQ ID NO 98
<211> LENGTH: 288
<212> TYPE: PRT
<213> ORGANISM: Human immunodeficiency virus type 1

<400> SEQUENCE: 98

Phe Leu Asp Gly Ile Asp Lys Ala Gln Asp Glu His Glu Lys Tyr His
1 5 10 15

Ser Asn Trp Arg Ala Met Ala Ser Asp Phe Asn Leu Pro Pro Val Val
20 25 30

Ala Ala Ala Ile Val Ala Ser Cys Asp Lys Cys Gln Leu Lys Gly Glu
35 40 45

Ala Met His Gly Gln Val Asp Cys Ser Pro Gly Ile Trp Gln Leu Asp
50 55 60

Cys Thr His Leu Glu Gly Lys Val Ile Leu Val Ala Val His Val Ala
65 70 75 80

Ser Gly Tyr Ile Glu Ala Glu Val Ile Pro Ala Glu Thr Gly Gln Glu
85 90 95

Thr Ala Tyr Phe Leu Leu Lys Leu Ala Gly Arg Trp Pro Val Lys Thr
100 105 110

Ile His Thr Asp Asn Gly Ser Asn Phe Thr Ser Ala Thr Val Lys Ala
115 120 125

Ala Cys Trp Trp Ala Gly Ile Lys Gln Glu Phe Gly Ile Pro Tyr Asn
130 135 140

Pro Gln Ser Gln Gly Val Val Glu Ser Met Asn Lys Glu Leu Lys Lys
145 150 155 160

Ile Ile Gly Gln Val Arg Asp Gln Ala Glu His Leu Lys Thr Ala Val
165 170 175

Gln Met Ala Val Phe Ile His Asn Phe Lys Arg Lys Gly Gly Ile Gly
180 185 190

Gly Tyr Ser Ala Gly Glu Arg Ile Val Asp Ile Ile Ala Thr Asp Ile
195 200 205

Gln Thr Lys Glu Leu Gln Lys Gln Ile Thr Lys Ile Gln Asn Phe Arg
210 215 220

Val Tyr Tyr Arg Asp Ser Arg Asn Pro Leu Trp Lys Gly Pro Ala Lys
225 230 235 240

Leu Leu Trp Lys Gly Glu Gly Ala Val Val Ile Gln Asp Asn Ser Asp
245 250 255

Ile Lys Val Val Pro Arg Arg Lys Ala Lys Ile Ile Arg Asp Tyr Gly

-continued

```
            260                 265                 270

Lys Gln Met Ala Gly Asp Asp Cys Val Ala Ser Arg Gln Asp Glu Asp
        275                 280                 285


<210> SEQ ID NO 99
<211> LENGTH: 288
<212> TYPE: PRT
<213> ORGANISM: Human immunodeficiency virus type 1

<400> SEQUENCE: 99

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Ala Ala Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 100
<211> LENGTH: 288
<212> TYPE: PRT
<213> ORGANISM: Human immunodeficiency virus type 1

<400> SEQUENCE: 100

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
```

-continued

```
            20                  25                  30

Ala Lys Glu Ile Val Ala Ser Cys Asp Lys Cys Gln Leu Ala Gly Ala
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 101
<211> LENGTH: 288
<212> TYPE: PRT
<213> ORGANISM: Human immunodeficiency virus type 1

<400> SEQUENCE: 101

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr Ala Leu Ala Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110
```

-continued

```
Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 102
<211> LENGTH: 288
<212> TYPE: PRT
<213> ORGANISM: Human immunodeficiency virus type 1

<400> SEQUENCE: 102

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Ala Gly Ala Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205
```

-continued

```
Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
            245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 103
<211> LENGTH: 288
<212> TYPE: PRT
<213> ORGANISM: Human immunodeficiency virus type 1

<400> SEQUENCE: 103

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Ala Ala Ala Val Ile Pro Ala Glu Thr Gly Gln Glu
            85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
            165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
            245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

-continued

<210> SEQ ID NO 104
<211> LENGTH: 288
<212> TYPE: PRT
<213> ORGANISM: Human immunodeficiency virus type 1

<400> SEQUENCE: 104

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Ala Leu Ala Gly Ala Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 105
<211> LENGTH: 288
<212> TYPE: PRT
<213> ORGANISM: Human immunodeficiency virus type 1

<400> SEQUENCE: 105

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
```

-continued

```
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Ala Trp Pro Val Ala Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 106
<211> LENGTH: 288
<212> TYPE: PRT
<213> ORGANISM: Human immunodeficiency virus type 1

<400> SEQUENCE: 106

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Ala Thr
            100                 105                 110

Ile Ala Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140
```

-continued

```
Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 107
<211> LENGTH: 288
<212> TYPE: PRT
<213> ORGANISM: Human immunodeficiency virus type 1

<400> SEQUENCE: 107

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Ala Glu Leu Ala Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240
```

-continued

```
Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 108
<211> LENGTH: 288
<212> TYPE: PRT
<213> ORGANISM: Human immunodeficiency virus type 1

<400> SEQUENCE: 108

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Ala Glu Leu Ala Lys
145                 150                 155                 160

Ile Ile Gly Gln Val Ala Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 109
<211> LENGTH: 288
<212> TYPE: PRT
<213> ORGANISM: Human immunodeficiency virus type 1

<400> SEQUENCE: 109
```

-continued

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Ala Glu Leu Lys Ala
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 110
<211> LENGTH: 288
<212> TYPE: PRT
<213> ORGANISM: Human immunodeficiency virus type 1

<400> SEQUENCE: 110

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
```

-continued

```
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Ala Ala
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 111
<211> LENGTH: 288
<212> TYPE: PRT
<213> ORGANISM: Human immunodeficiency virus type 1

<400> SEQUENCE: 111

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Ala Ala Asp Gln Ala Glu His Leu Lys Thr Ala Val
                165                 170                 175
```

-continued

Gln Met Ala Val Phe Ile His Asn Phe Lys Arg Lys Gly Gly Ile Gly
180 185 190

Gly Tyr Ser Ala Gly Glu Arg Ile Val Asp Ile Ile Ala Thr Asp Ile
195 200 205

Gln Thr Lys Glu Leu Gln Lys Gln Ile Thr Lys Ile Gln Asn Phe Arg
210 215 220

Val Tyr Tyr Arg Asp Ser Arg Asn Pro Leu Trp Lys Gly Pro Ala Lys
225 230 235 240

Leu Leu Trp Lys Gly Glu Gly Ala Val Val Ile Gln Asp Asn Ser Asp
245 250 255

Ile Lys Val Val Pro Arg Arg Lys Ala Lys Ile Ile Arg Asp Tyr Gly
260 265 270

Lys Gln Met Ala Gly Asp Asp Cys Val Ala Ser Arg Gln Asp Glu Asp
275 280 285

<210> SEQ ID NO 112
<211> LENGTH: 288
<212> TYPE: PRT
<213> ORGANISM: Human immunodeficiency virus type 1

<400> SEQUENCE: 112

Phe Leu Asp Gly Ile Asp Lys Ala Gln Asp Glu His Glu Lys Tyr His
1 5 10 15

Ser Asn Trp Arg Ala Met Ala Ser Asp Phe Asn Leu Pro Pro Val Val
20 25 30

Ala Lys Glu Ile Val Ala Ser Cys Asp Lys Cys Gln Leu Lys Gly Glu
35 40 45

Ala Met His Gly Gln Val Asp Cys Ser Pro Gly Ile Trp Gln Leu Asp
50 55 60

Cys Thr His Leu Glu Gly Lys Val Ile Leu Val Ala Val His Val Ala
65 70 75 80

Ser Gly Tyr Ile Glu Ala Glu Val Ile Pro Ala Glu Thr Gly Gln Glu
85 90 95

Thr Ala Tyr Phe Leu Leu Lys Leu Ala Gly Arg Trp Pro Val Lys Thr
100 105 110

Ile His Thr Asp Asn Gly Ser Asn Phe Thr Ser Ala Thr Val Lys Ala
115 120 125

Ala Cys Trp Trp Ala Gly Ile Lys Gln Glu Phe Gly Ile Pro Tyr Asn
130 135 140

Pro Gln Ser Gln Gly Val Val Glu Ser Met Asn Lys Glu Leu Lys Lys
145 150 155 160

Ile Ile Gly Gln Val Ala Ala Gln Ala Glu His Leu Lys Thr Ala Val
165 170 175

Gln Met Ala Val Phe Ile His Asn Phe Lys Arg Lys Gly Gly Ile Gly
180 185 190

Gly Tyr Ser Ala Gly Glu Arg Ile Val Asp Ile Ile Ala Thr Asp Ile
195 200 205

Gln Thr Lys Glu Leu Gln Lys Gln Ile Thr Lys Ile Gln Asn Phe Arg
210 215 220

Val Tyr Tyr Arg Asp Ser Arg Asn Pro Leu Trp Lys Gly Pro Ala Lys
225 230 235 240

Leu Leu Trp Lys Gly Glu Gly Ala Val Val Ile Gln Asp Asn Ser Asp
245 250 255

Ile Lys Val Val Pro Arg Arg Lys Ala Lys Ile Ile Arg Asp Tyr Gly
260 265 270

```
Lys Gln Met Ala Gly Asp Asp Cys Val Ala Ser Arg Gln Asp Glu Asp
        275                 280                 285
```

<210> SEQ ID NO 113
<211> LENGTH: 288
<212> TYPE: PRT
<213> ORGANISM: Human immunodeficiency virus type 1

<400> SEQUENCE: 113

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Ala Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 114
<211> LENGTH: 288
<212> TYPE: PRT
<213> ORGANISM: Human immunodeficiency virus type 1

<400> SEQUENCE: 114

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30
```

-continued

```
Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu Ala Leu Ala Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 115
<211> LENGTH: 288
<212> TYPE: PRT
<213> ORGANISM: Human immunodeficiency virus type 1

<400> SEQUENCE: 115

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
```

-continued

```
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Ala Ala Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 116
<211> LENGTH: 288
<212> TYPE: PRT
<213> ORGANISM: Human immunodeficiency virus type 1

<400> SEQUENCE: 116

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Ala Arg Ala Gly Gly Ile Gly
            180                 185                 190

Gly Tyr Ser Ala Gly Glu Arg Ile Val Asp Ile Ile Ala Thr Asp Ile
        195                 200                 205
```

-continued

```
Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 117
<211> LENGTH: 288
<212> TYPE: PRT
<213> ORGANISM: Human immunodeficiency virus type 1

<400> SEQUENCE: 117

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Ala Ala Ala Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 118
```

-continued

<211> LENGTH: 288
<212> TYPE: PRT
<213> ORGANISM: Human immunodeficiency virus type 1

<400> SEQUENCE: 118

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Ala Ala Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 119
<211> LENGTH: 288
<212> TYPE: PRT
<213> ORGANISM: Human immunodeficiency virus type 1

<400> SEQUENCE: 119

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60
```

-continued

Cys Thr His Leu Glu Gly Lys Val Ile Leu Val Ala Val His Val Ala
65 70 75 80

Ser Gly Tyr Ile Glu Ala Glu Val Ile Pro Ala Glu Thr Gly Gln Glu
85 90 95

Thr Ala Tyr Phe Leu Leu Lys Leu Ala Gly Arg Trp Pro Val Lys Thr
100 105 110

Ile His Thr Asp Asn Gly Ser Asn Phe Thr Ser Ala Thr Val Lys Ala
115 120 125

Ala Cys Trp Trp Ala Gly Ile Lys Gln Glu Phe Gly Ile Pro Tyr Asn
130 135 140

Pro Gln Ser Gln Gly Val Val Glu Ser Met Asn Lys Glu Leu Lys Lys
145 150 155 160

Ile Ile Gly Gln Val Arg Asp Gln Ala Glu His Leu Lys Thr Ala Val
165 170 175

Gln Met Ala Val Phe Ile His Asn Phe Lys Arg Lys Gly Gly Ile Gly
180 185 190

Gly Tyr Ser Ala Gly Ala Ala Ile Val Asp Ile Ile Ala Thr Asp Ile
195 200 205

Gln Thr Lys Glu Leu Gln Lys Gln Ile Thr Lys Ile Gln Asn Phe Arg
210 215 220

Val Tyr Tyr Arg Asp Ser Arg Asn Pro Leu Trp Lys Gly Pro Ala Lys
225 230 235 240

Leu Leu Trp Lys Gly Glu Gly Ala Val Val Ile Gln Asp Asn Ser Asp
245 250 255

Ile Lys Val Val Pro Arg Arg Lys Ala Lys Ile Ile Arg Asp Tyr Gly
260 265 270

Lys Gln Met Ala Gly Asp Asp Cys Val Ala Ser Arg Gln Asp Glu Asp
275 280 285

<210> SEQ ID NO 120
<211> LENGTH: 288
<212> TYPE: PRT
<213> ORGANISM: Human immunodeficiency virus type 1

<400> SEQUENCE: 120

Phe Leu Asp Gly Ile Asp Lys Ala Gln Asp Glu His Glu Lys Tyr His
1 5 10 15

Ser Asn Trp Arg Ala Met Ala Ser Asp Phe Asn Leu Pro Pro Val Val
20 25 30

Ala Lys Glu Ile Val Ala Ser Cys Asp Lys Cys Gln Leu Lys Gly Glu
35 40 45

Ala Met His Gly Gln Val Asp Cys Ser Pro Gly Ile Trp Gln Leu Asp
50 55 60

Cys Thr His Leu Glu Gly Lys Val Ile Leu Val Ala Val His Val Ala
65 70 75 80

Ser Gly Tyr Ile Glu Ala Glu Val Ile Pro Ala Glu Thr Gly Gln Glu
85 90 95

Thr Ala Tyr Phe Leu Leu Lys Leu Ala Gly Arg Trp Pro Val Lys Thr
100 105 110

Ile His Thr Asp Asn Gly Ser Asn Phe Thr Ser Ala Thr Val Lys Ala
115 120 125

Ala Cys Trp Trp Ala Gly Ile Lys Gln Glu Phe Gly Ile Pro Tyr Asn
130 135 140

Pro Gln Ser Gln Gly Val Val Glu Ser Met Asn Lys Glu Leu Lys Lys

-continued

```
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Ala Ile Val Ala Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 121
<211> LENGTH: 288
<212> TYPE: PRT
<213> ORGANISM: Human immunodeficiency virus type 1

<400> SEQUENCE: 121

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Leu Lys Leu Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240
```

-continued

Leu Leu Trp Lys Gly Glu Gly Ala Val Val Ile Gln Asp Asn Ser Asp
245 250 255

Ile Lys Val Val Pro Arg Arg Lys Ala Lys Ile Ile Arg Asp Tyr Gly
260 265 270

Lys Gln Met Ala Gly Asp Asp Cys Val Ala Ser Arg Gln Asp Glu Asp
275 280 285

<210> SEQ ID NO 122
<211> LENGTH: 288
<212> TYPE: PRT
<213> ORGANISM: Human immunodeficiency virus type 1

<400> SEQUENCE: 122

Phe Leu Asp Gly Ile Asp Lys Ala Gln Asp Glu His Glu Lys Tyr His
1 5 10 15

Ser Asn Trp Arg Ala Met Ala Ser Asp Phe Asn Leu Pro Pro Val Val
20 25 30

Ala Lys Glu Ile Val Ala Ser Cys Asp Lys Cys Gln Leu Lys Gly Glu
35 40 45

Ala Met His Gly Gln Val Asp Cys Ser Pro Gly Ile Trp Gln Leu Asp
50 55 60

Cys Thr His Leu Glu Gly Lys Val Ile Leu Val Ala Val His Val Ala
65 70 75 80

Ser Gly Tyr Ile Glu Ala Glu Val Ile Pro Ala Glu Thr Gly Gln Glu
85 90 95

Thr Ala Tyr Phe Leu Leu Lys Leu Ala Gly Arg Trp Pro Val Lys Thr
100 105 110

Ile His Thr Asp Asn Gly Ser Asn Phe Thr Ser Ala Thr Val Lys Ala
115 120 125

Ala Cys Trp Trp Ala Gly Ile Lys Gln Glu Phe Gly Ile Pro Tyr Asn
130 135 140

Pro Gln Ser Gln Gly Val Val Glu Ser Met Asn Lys Glu Leu Lys Lys
145 150 155 160

Ile Ile Gly Gln Val Arg Asp Gln Ala Glu His Leu Lys Thr Ala Val
165 170 175

Gln Met Ala Val Phe Ile His Asn Phe Lys Arg Lys Gly Gly Ile Gly
180 185 190

Gly Tyr Ser Ala Gly Glu Arg Ile Val Asp Ile Ile Ala Thr Asp Ile
195 200 205

Gln Thr Lys Glu Leu Gln Lys Gln Ile Thr Lys Ile Gln Asn Phe Ala
210 215 220

Val Tyr Tyr Ala Asp Ser Arg Asn Pro Leu Trp Lys Gly Pro Ala Lys
225 230 235 240

Leu Leu Trp Lys Gly Glu Gly Ala Val Val Ile Gln Asp Asn Ser Asp
245 250 255

Ile Lys Val Val Pro Arg Arg Lys Ala Lys Ile Ile Arg Asp Tyr Gly
260 265 270

Lys Gln Met Ala Gly Asp Asp Cys Val Ala Ser Arg Gln Asp Glu Asp
275 280 285

<210> SEQ ID NO 123
<211> LENGTH: 288
<212> TYPE: PRT
<213> ORGANISM: Human immunodeficiency virus type 1

<400> SEQUENCE: 123

-continued

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Ala Ser Ala Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 124
<211> LENGTH: 288
<212> TYPE: PRT
<213> ORGANISM: Human immunodeficiency virus type 1

<400> SEQUENCE: 124

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95
```

-continued

```
Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Ala Gly Pro Ala Ala
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 125
<211> LENGTH: 288
<212> TYPE: PRT
<213> ORGANISM: Human immunodeficiency virus type 1

<400> SEQUENCE: 125

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
```

-continued

```
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Ala Asn Ser Ala
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 126
<211> LENGTH: 288
<212> TYPE: PRT
<213> ORGANISM: Human immunodeficiency virus type 1

<400> SEQUENCE: 126

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Ala
                245                 250                 255

Ile Ala Val Val Pro Arg Arg Lys Ala Lys Ile Ile Arg Asp Tyr Gly
            260                 265                 270
```

-continued

```
Lys Gln Met Ala Gly Asp Asp Cys Val Ala Ser Arg Gln Asp Glu Asp
        275                 280                 285
```

<210> SEQ ID NO 127
<211> LENGTH: 288
<212> TYPE: PRT
<213> ORGANISM: Human immunodeficiency virus type 1

<400> SEQUENCE: 127

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Ala Ala Lys Ala Ala Ile Ile Arg Asp Tyr Gly
            260                 265                 270

Lys Gln Met Ala Gly Asp Asp Cys Val Ala Ser Arg Gln Asp Glu Asp
        275                 280                 285
```

<210> SEQ ID NO 128
<211> LENGTH: 288
<212> TYPE: PRT
<213> ORGANISM: Human immunodeficiency virus type 1

<400> SEQUENCE: 128

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30
```

-continued

```
Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Ala Ala Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 129
<211> LENGTH: 288
<212> TYPE: PRT
<213> ORGANISM: Human immunodeficiency virus type 1

<400> SEQUENCE: 129

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Ser Ala Thr Val Lys Ala
        115                 120                 125
```

-continued

```
Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Ala Ala Tyr Gly
            260                 265                 270

Lys Gln Met Ala Gly Asp Asp Cys Val Ala Ser Arg Gln Asp Glu Asp
        275                 280                 285
```

<210> SEQ ID NO 130
<211> LENGTH: 177
<212> TYPE: DNA
<213> ORGANISM: Human immunodeficiency virus type 1

<400> SEQUENCE: 130

```
gaattacaaa aacaaattac aaaaattcaa aattttcggg tttattacag ggacagcaga     60

aatccacttt ggaaaggacc agcaaagctc ctctggaaag gtgaaggggc agtagtaata    120

caagataata gtgacataaa agtagtgcca agaagaaaag caaagatcat tagggat       177
```

<210> SEQ ID NO 131
<211> LENGTH: 147
<212> TYPE: DNA
<213> ORGANISM: Human immunodeficiency virus type 1

<400> SEQUENCE: 131

```
gaattacaaa aacaaattac aaaaattcaa aattttcggg tttattacag ggacagcaga     60

aatccacttt ggaaaggacc agcaaagctc ctctggaaag gtgaaggggc agtagtaata    120

caagataata gtgacataaa agtagtg                                         147
```

<210> SEQ ID NO 132
<211> LENGTH: 204
<212> TYPE: DNA
<213> ORGANISM: Human immunodeficiency virus type 1

<400> SEQUENCE: 132

```
caaaattttc gggtttatta cagggacagc agaaatccac tttggaaagg accagcaaag     60

ctcctctgga aaggtgaagg ggcagtagta atacaagata atagtgacat aaaagtagtg    120

ccaagaagaa aagcaaagat cattagggat tatggaaaac agatggcagg tgatgattgt    180

gtggcaagta gacaggatga ggat                                            204
```

<210> SEQ ID NO 133
<211> LENGTH: 177
<212> TYPE: DNA

-continued

<213> ORGANISM: Human immunodeficiency virus type 1

<400> SEQUENCE: 133
agcagaaatc cactttggaa aggaccagca aagctcctct ggaaaggtga aggggcagta 60
gtaatacaag ataatagtga cataaaagta gtgccaagaa gaaaagcaaa gatcattagg 120
gattatggaa aacagatggc aggtgatgat tgtgtggcaa gtagacagga tgaggat 177

<210> SEQ ID NO 134
<211> LENGTH: 147
<212> TYPE: DNA
<213> ORGANISM: Human immunodeficiency virus type 1

<400> SEQUENCE: 134
aagctcctct ggaaaggtga aggggcagta gtaatacaag ataatagtga cataaaagta 60
gtgccaagaa gaaaagcaaa gatcattagg gattatggaa aacagatggc aggtgatgat 120
tgtgtggcaa gtagacagga tgaggat 147

<210> SEQ ID NO 135
<211> LENGTH: 117
<212> TYPE: DNA
<213> ORGANISM: Human immunodeficiency virus type 1

<400> SEQUENCE: 135
gtaatacaag ataatagtga cataaaagta gtgccaagaa gaaaagcaaa gatcattagg 60
gattatggaa aacagatggc aggtgatgat tgtgtggcaa gtagacagga tgaggat 117

<210> SEQ ID NO 136
<211> LENGTH: 87
<212> TYPE: DNA
<213> ORGANISM: Human immunodeficiency virus type 1

<400> SEQUENCE: 136
gtgccaagaa gaaaagcaaa gatcattagg gattatggaa aacagatggc aggtgatgat 60
tgtgtggcaa gtagacagga tgaggat 87

<210> SEQ ID NO 137
<211> LENGTH: 57
<212> TYPE: DNA
<213> ORGANISM: Human immunodeficiency virus type 1

<400> SEQUENCE: 137
gattatggaa aacagatggc aggtgatgat tgtgtggcaa gtagacagga tgaggat 57

<210> SEQ ID NO 138
<211> LENGTH: 150
<212> TYPE: DNA
<213> ORGANISM: Human immunodeficiency virus type 1

<400> SEQUENCE: 138
caaaattttc gggtttatta cagggacagc agaaatccac tttggaaagg accagcaaag 60
ctcctctgga aaggtgaagg ggcagtagta atacaagata atagtgacat aaaagtagtg 120
ccaagaagaa aagcaaagat cattagggat 150

<210> SEQ ID NO 139
<211> LENGTH: 59
<212> TYPE: PRT
<213> ORGANISM: Human immunodeficiency virus type 1

<400> SEQUENCE: 139

-continued

```
Glu Leu Gln Lys Gln Ile Thr Lys Ile Gln Asn Phe Arg Val Tyr Tyr
1               5                   10                  15

Arg Asp Ser Arg Asn Pro Leu Trp Lys Gly Pro Ala Lys Leu Leu Trp
            20                  25                  30

Lys Gly Glu Gly Ala Val Val Ile Gln Asp Asn Ser Asp Ile Lys Val
        35                  40                  45

Val Pro Arg Arg Lys Ala Lys Ile Ile Arg Asp
    50                  55


<210> SEQ ID NO 140
<211> LENGTH: 49
<212> TYPE: PRT
<213> ORGANISM: Human immunodeficiency virus type 1

<400> SEQUENCE: 140

Glu Leu Gln Lys Gln Ile Thr Lys Ile Gln Asn Phe Arg Val Tyr Tyr
1               5                   10                  15

Arg Asp Ser Arg Asn Pro Leu Trp Lys Gly Pro Ala Lys Leu Leu Trp
            20                  25                  30

Lys Gly Glu Gly Ala Val Val Ile Gln Asp Asn Ser Asp Ile Lys Val
        35                  40                  45

Val


<210> SEQ ID NO 141
<211> LENGTH: 69
<212> TYPE: PRT
<213> ORGANISM: Human immunodeficiency virus type 1

<400> SEQUENCE: 141

Ile Gln Asn Phe Arg Val Tyr Tyr Arg Asp Ser Arg Asn Pro Leu Trp
1               5                   10                  15

Lys Gly Pro Ala Lys Leu Leu Trp Lys Gly Glu Gly Ala Val Val Ile
            20                  25                  30

Gln Asp Asn Ser Asp Ile Lys Val Val Pro Arg Arg Lys Ala Lys Ile
        35                  40                  45

Ile Arg Asp Tyr Gly Lys Gln Met Ala Gly Asp Asp Cys Val Ala Ser
    50                  55                  60

Arg Gln Asp Glu Asp
65


<210> SEQ ID NO 142
<211> LENGTH: 59
<212> TYPE: PRT
<213> ORGANISM: Human immunodeficiency virus type 1

<400> SEQUENCE: 142

Ser Arg Asn Pro Leu Trp Lys Gly Pro Ala Lys Leu Leu Trp Lys Gly
1               5                   10                  15

Glu Gly Ala Val Val Ile Gln Asp Asn Ser Asp Ile Lys Val Val Pro
            20                  25                  30

Arg Arg Lys Ala Lys Ile Ile Arg Asp Tyr Gly Lys Gln Met Ala Gly
        35                  40                  45

Asp Asp Cys Val Ala Ser Arg Gln Asp Glu Asp
    50                  55


<210> SEQ ID NO 143
<211> LENGTH: 49
<212> TYPE: PRT
```

<213> ORGANISM: Human immunodeficiency virus type 1

<400> SEQUENCE: 143

```
Lys Leu Leu Trp Lys Gly Glu Gly Ala Val Val Ile Gln Asp Asn Ser
1               5                   10                  15

Asp Ile Lys Val Val Pro Arg Arg Lys Ala Lys Ile Ile Arg Asp Tyr
            20                  25                  30

Gly Lys Gln Met Ala Gly Asp Asp Cys Val Ala Ser Arg Gln Asp Glu
        35                  40                  45

Asp
```

<210> SEQ ID NO 144
<211> LENGTH: 39
<212> TYPE: PRT
<213> ORGANISM: Human immunodeficiency virus type 1

<400> SEQUENCE: 144

```
Val Ile Gln Asp Asn Ser Asp Ile Lys Val Val Pro Arg Arg Lys Ala
1               5                   10                  15

Lys Ile Ile Arg Asp Tyr Gly Lys Gln Met Ala Gly Asp Asp Cys Val
            20                  25                  30

Ala Ser Arg Gln Asp Glu Asp
        35
```

<210> SEQ ID NO 145
<211> LENGTH: 29
<212> TYPE: PRT
<213> ORGANISM: Human immunodeficiency virus type 1

<400> SEQUENCE: 145

```
Val Pro Arg Arg Lys Ala Lys Ile Ile Arg Asp Tyr Gly Lys Gln Met
1               5                   10                  15

Ala Gly Asp Asp Cys Val Ala Ser Arg Gln Asp Glu Asp
            20                  25
```

<210> SEQ ID NO 146
<211> LENGTH: 19
<212> TYPE: PRT
<213> ORGANISM: Human immunodeficiency virus type 1

<400> SEQUENCE: 146

```
Asp Tyr Gly Lys Gln Met Ala Gly Asp Asp Cys Val Ala Ser Arg Gln
1               5                   10                  15

Asp Glu Asp
```

<210> SEQ ID NO 147
<211> LENGTH: 51
<212> TYPE: PRT
<213> ORGANISM: Human immunodeficiency virus type 1

<400> SEQUENCE: 147

```
Ile Gln Asn Phe Arg Val Tyr Tyr Arg Asp Ser Arg Asn Pro Leu Trp
1               5                   10                  15

Lys Gly Pro Ala Lys Leu Leu Trp Lys Gly Glu Gly Ala Val Val Ile
            20                  25                  30

Gln Asp Asn Ser Asp Ile Lys Val Val Pro Arg Arg Lys Ala Lys Ile
        35                  40                  45

Ile Arg Asp
    50
```

-continued

<210> SEQ ID NO 148
<211> LENGTH: 234
<212> TYPE: DNA
<213> ORGANISM: Human immunodeficiency virus type 1

<400> SEQUENCE: 148
gaattacaaa aacaaattac aaaaattcaa aattttcggg tttattacag ggacagcaga 60
aatccacttt ggaaaggacc agcaaagctc ctctggaaag gtgaaggggc agtagtaata 120
caagataata gtgacataaa agtagtgcca agaagaaaag caaagatcat tagggattat 180
ggaaaacaga tggcaggtga tgattgtgtg gcaagtagac aggatgagga ttag 234

<210> SEQ ID NO 149
<211> LENGTH: 77
<212> TYPE: PRT
<213> ORGANISM: Human immunodeficiency virus type 1

<400> SEQUENCE: 149

Glu Leu Gln Lys Gln Ile Thr Lys Ile Gln Asn Phe Arg Val Tyr Tyr
1 5 10 15

Arg Asp Ser Arg Asn Pro Leu Trp Lys Gly Pro Ala Lys Leu Leu Trp
20 25 30

Lys Gly Glu Gly Ala Val Val Ile Gln Asp Asn Ser Asp Ile Lys Val
35 40 45

Val Pro Arg Arg Lys Ala Lys Ile Ile Arg Asp Tyr Gly Lys Gln Met
50 55 60

Ala Gly Asp Asp Cys Val Ala Ser Arg Gln Asp Glu Asp
65 70 75